US008618252B2

(12) United States Patent
Farrington et al.

(10) Patent No.: US 8,618,252 B2
(45) Date of Patent: Dec. 31, 2013

(54) NEONATAL FC RECEPTOR (FCRN)-BINDING POLYPEPTIDE VARIANTS, DIMERIC FC BINDING PROTEINS AND METHODS RELATED THERETO

(75) Inventors: Graham K. Farrington, Acton, MA (US); Alexey Alexandrovich Lugovskoy, Woburn, MA (US); Werner Meier, Burlington, MA (US); John K. Eldredge, South Chatham, MA (US); Ellen Garber, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 12/966,541

(22) Filed: Dec. 13, 2010

(65) Prior Publication Data

US 2012/0003210 A1    Jan. 5, 2012

Related U.S. Application Data

(63) Continuation of application No. 11/432,872, filed on May 12, 2006, now abandoned, which is a continuation of application No. PCT/US2004/037929, filed on Nov. 12, 2004.

(60) Provisional application No. 60/519,743, filed on Nov. 12, 2003, provisional application No. 60/519,733, filed on Nov. 12, 2003, provisional application No. 60/519,744, filed on Nov. 12, 2003.

(51) Int. Cl.
*C07K 1/00*    (2006.01)
*C07K 16/00*   (2006.01)
*C12P 21/08*   (2006.01)
*A61K 39/395*  (2006.01)
*A61K 39/40*   (2006.01)
*A61K 39/00*   (2006.01)

(52) U.S. Cl.
USPC .................. 530/350; 530/387.1; 530/387.3; 530/388.1; 530/388.15; 424/130.1; 424/132.1; 424/133.1; 424/134.1; 424/141.1; 424/142.1

(58) Field of Classification Search
None
See application file for complete search history.

(56) References Cited

U.S. PATENT DOCUMENTS

| 5,648,260 | A | 7/1997 | Winter et al. |
| 5,739,277 | A | 4/1998 | Presta et al. |
| 5,834,250 | A | 11/1998 | Wells et al. |
| 5,869,046 | A | 2/1999 | Presta et al. |
| 6,121,022 | A | 9/2000 | Presta et al. |
| 6,737,056 | B1 | 5/2004 | Presta |
| 7,662,925 | B2 | 2/2010 | Lazar et al. |
| 2002/0142374 | A1 | 10/2002 | Gallo et al. |
| 2003/0078385 | A1 | 4/2003 | Arathoon et al. |
| 2003/0190614 | A1 | 10/2003 | Presta et al. |
| 2003/0204346 | A1 | 10/2003 | Kennedy et al. |
| 2004/0002587 | A1 | 1/2004 | Watkins et al. |
| 2004/0132101 | A1 | 7/2004 | Lazar et al. |
| 2004/0142374 | A1 | 7/2004 | Reed et al. |
| 2004/0185045 | A1 | 9/2004 | Koenig et al. |
| 2005/0024298 | A1 | 2/2005 | Tam |
| 2005/0037000 | A1 | 2/2005 | Stavenhagen et al. |
| 2005/0054832 | A1 | 3/2005 | Lazar et al. |
| 2005/0244403 | A1 | 11/2005 | Lazar et al. |
| 2005/0249723 | A1 | 11/2005 | Lazar |

FOREIGN PATENT DOCUMENTS

| WO | 88/07089 A1 | 9/1988 |
| WO | 96/14339 A1 | 5/1996 |
| WO | 98/05787 A1 | 2/1998 |
| WO | 98/23289 A1 | 6/1998 |
| WO | 99/51642 A1 | 10/1999 |
| WO | 99/58572 A1 | 11/1999 |
| WO | 00/09560 A2 | 2/2000 |
| WO | 00/32767 A1 | 6/2000 |
| WO | 00/42072 A2 | 7/2000 |
| WO | 02/44215 A2 | 6/2002 |
| WO | 02/060919 A2 | 8/2002 |
| WO | 03/074569 A2 | 9/2003 |
| WO | 03/074679 A2 | 9/2003 |
| WO | WO 03/074679 | * 9/2003 |
| WO | 2004/016750 A2 | 2/2004 |
| WO | 2004/029207 A2 | 4/2004 |
| WO | 2004/035752 A2 | 4/2004 |
| WO | 2004/063351 A2 | 7/2004 |
| WO | 2004/074455 A2 | 9/2004 |
| WO | 2004/099249 A2 | 11/2004 |
| WO | 2005/040217 A2 | 5/2005 |
| WO | 2005/070963 A1 | 8/2005 |
| WO | 2005/077981 A2 | 8/2005 |

(Continued)

OTHER PUBLICATIONS

Martin et al. Molecular Cell, vol. 7, 867-877, Apr. 2001.*
Angal, S. et al, "A Single Amino Acid Substitution Abolishes the Hetergeneity of Chimeric Mouse/Human (IgG4) Antibody," Molecular Immunology, vol. 30(1):105-108 (1993).
Bertolotti-Ciarlet, Andrea et al., "Impact of methionine oxidation on the binding of human IgG1 to FcRn and Fcg receptors," Molecular Immunology, doi:10.1016/j.molimm.2009.02.002 (2009).
Brekke, Ole Henrik et al, "Human IgG isotype-specific amino acid residues affecting complement-mediated cell lysis and phagocytosis," Eur. J. Immunol., vol. 24:2542-2547 (1994).
Caron, Philip C. et al, "Engineered Humanized Dimeric Forms of IgG Are More Effective Antibodies," J. Exp. Med., vol. 176:1191-1195 (1992).

(Continued)

*Primary Examiner* — Chun Dahle
(74) *Attorney, Agent, or Firm* — Nelson Mullins Riley & Scarborough LLP; Debra J. Milasinic, Esq.

(57) ABSTRACT

The compositions and methods of the present invention are based, in part, on our discovery that an effector function mediated by an Fc-containing polypeptide can be altered by modifying one or more amino acid residues within the polypeptide (by, for example, electrostatic optimization). The polypeptides that can be generated according to the methods of the invention are highly variable, and they can include antibodies and fusion proteins that contain an Fc region or a biologically active portion thereof.

17 Claims, 10 Drawing Sheets

(56) References Cited

FOREIGN PATENT DOCUMENTS

| WO | 2005/092925 A2 | 10/2005 |
|---|---|---|
| WO | 2005/123780 A2 | 12/2005 |
| WO | 2006/019447 A1 | 2/2006 |
| WO | 2006/047350 A2 | 5/2006 |
| WO | 2006/085967 A2 | 8/2006 |

OTHER PUBLICATIONS

Canfield, Stephen M. et al, "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).
Chappel, M. Suzanne et al, "Identification of a Secondary FcgRI Binding Site within a Genetically Engineered Human IgG Antibody," The Journal of Biological Chemistry, vol. 268(33):25124-25131 (1993).
Chappel M. Suzanne et al, "Identification of the Fcg receptor class I binding site in human IgG through the use of recombinant IgG1/IgG2 hybrid and point-mutated antibodies," Proc. Natl. Acad. Sci. USA, vol. 88:9036-9040 (1991).
Coloma, M. Josefina et al, "The Hinge as a Spacer Contributes to Covalent Assembly and Is Required for Function of IgG," The Journal of Immunology, vol. 458:733-740 (1997).
Dall'acqua, William F. et al., "Increasing the Affinity of a Human IgG1 for the Neonatal Fc Receptor: Biological Consequences," The Journal of Immunology, vol. 169:5171-5180 (2002).
Ghetie, Victor et al., "Increasing the serum persistence of an IgG fragment by random mutagenesis," Nature Biotechnology, vol. 15:637-640 (1997).
Kim, Jin-Kyoo et al., "Identifying amino acid residues that influence plasma clearance of murine IgG1 fragments by site-directed mutagenesis," Eur. J. Immunol., vol. 24:542-548 (1994).
Kusuhara, Hiroyuki et al., "Brain Efflux Index Method, Characterization of Efflux Transport Across the Blood-Brain Barrier," Methods in Molecular Medicine, vol. 89:219-231 (2003).
Lund, John et al, "Multiple Interactions of IgG with Its Core Oligosaccharide Can Modulate Recognition by Complement and Human Fcg Receptor I and Influence the Synthesis of Its Oligosaccharide Chains," The Journal of Immunology, vol. 157:4963-4969 (1996).
Lund, John et al, "Oligosaccharide-protein interactions in IgG can modulate recognition by Fcg receptors," FASEB J., vol. 9:115-119 (1995).
Lund John et al, "Human FcgRI and FcgRII Interact with Distinct but Overlapping Sites on Human IgG," The Journal of Immunology, vol. 147(6):2657-2662 (1991).
Martin, W. Lance et al., "Crystal Structure at 2.8 Å of an FcRn/Heterodimeric Fc Complex: Mechanism of pH-Dependent Binding," Molecular Cell, vol. 7:867-877 (2001).
Schlachetzki, Felix et al., "Expression of the neonatal Fc receptor (FcRn) at the blood-brain barrier," J. Neurochem., vol. 81:203-206 (2002).
Schuurman, Janine et al, "The inter-heavy chain disulfide bonds of IgG4 are in equilibrium with intra-chain disulfide bonds," Molecular Immunology, vol. 38:1-8 (2001).
Shields, Robert L. et al, "High Resolution Mapping of the Binding Site on Human IgG1 for FcgRI, FcgRIII, and FcRn and Design of IgG1 Variants with Improved Binding to the FcgR," The Journal of Biological Chemistry, vol. 276 (9):6591-6604 (2001).
Smith, Richard I.F. et al, "Recombinant Polymeric IgG: An Approach to Engineering More Potent Antibodies," Bio/Technology, vol. 12:683-688 (1994).
Sondermann, Peter et al, "The 3.2-Å crystal structure of the human IgG1 Fc fragment-FcgRIII complex," Nature, vol. 406:267-273 (2000).
Thommesen, John E. et al, "Lysine 322 in the human IgG3 CH2 domain is crucial for antibody dependent complement activation," Molecular Immunology, vol. 37:995-1004 (2000).
Vitetta, Ellen S. et al., "Considering Therapeutic Antibodies," Science, vol. 313:308-309 (2006).
Zhang, Yun et al., "Rapid transferrin efflux from blood to brain across the blood-brain barrier," Journal of Neurochemistry, vol. 76:1597-1600 (2001).
European Office Action for Application No. 04810909.4, dated Nov. 3, 2008.
Chaudhury, Chaity et al., "The Major Histocompatibility Complex-related Fc Receptor for IgG (FcRn) Binds Albumin and Prolongs Its Lifespan," J. Exp. Med., vol. 197(3):315-322 (2003).
Dall'acqua, William F. et al., "Properties of Human IgG1s Engineered for Enhanced Binding to the Neonatal Fc Receptor (FcRn)," The Journal of Biological Chemistry, vol. 281(33):23514-23524 (2006).
Hinton, Paul R. et al., "Engineered Human IgG Antibodies with Longer Serum Half-lives in Primates," The Journal of Biological Chemistry, vol. 279(8):6213-6216 (2004).
Scheerens, Heleen et al., "Clinical Pharmacology of an Anti-CD4 Monoclonal Antibody with Enhanced FcRn Binding Affinity in a Phase I Study for Rheumatoid Arthritis," Clinical Immunology, vol. 135:S85, F.33 (2010).
Stone, Giancarlo C. et al., "The Fc Binding Site for Streptococcal Protein G is in the Cgamma2-Cgamma3 Interface Region of IgG and is Related to the Sites that Bind Staphylococcal Protein A and Human Rheumatoid Factors," The Journal of Immunology, vol. 143(2):565-570 (1989).
Canadian Office Action for Application No. 2,545,603, 3 pages, dated Jul. 26, 2012.
European Office Action for Application No. 10189703.1, 10 pages, dated May 4, 2012.
European Office Action for Application No. 04810909.4, 7 pages, dated Dec. 7, 2012.
European Partial European Search Report for Application No. 10189703.1, 7 pages, dated Oct. 7, 2011.
Japanese Office Action for Application No. 2006-539936, 11 pages, dated Dec. 7, 2012.
Popov, Sergei et al., "The Stoichiometry and Affinity of the Interaction of Murine Fc Fragments with the MHC Class I-Related Receptor, FcRn," Molecular Immunology, vol. 33(6):521-530 (1996).
Canadian Office Action for Application No. 2,545,603, 3 pages, dated Jul. 8, 2013.

\* cited by examiner

Figure 1A

DNA sequence of mature huCBE11 heavy chain encoded by pEAG1787
(SEQ ID NO. 3)

```
   1  GAGGTACAAC TGGTGGAGTC TGGGGGAGGC TTAGTGAAGC CTGGAGGGTC
  51  CCTGAGGCTC TCCTGTGCAG CCTCTGGATT CACTTTCAGT GACTATTACA
 101  TGTATTGGTT TCGCCAGGCC CCGGGAAAGG GGCTGGAGTG GGTCGCAACC
 151  ATTAGTGATG GTGGTAGTTA CACCTACTAT CCAGACAGTG TGAAGGGGCG
 201  ATTCACCATC TCCAGAGACA ATGCCAAGAA CAGCCTCTAC CTGCAGATGA
 251  GCAGCCTGAG GGCTGAGGAC ACAGCTGTGT ATTACTGCGC AAGAGAGGAG
 301  AATGGTAACT TTTACTACTT TGACTACTGG GGCCAAGGGA CCACGGTCAC
 351  CGTCTCCTCA GCCTCCACCA AGGGCCCATC GGTCTTCCCC CTGGCACCCT
 401  CCTCCAAGAG CACCTCTGGG GGCACAGCGG CCCTGGGCTG CCTGGTCAAG
 451  GACTACTTCC CCGAACCGGT GACGGTGTCG TGGAACTCAG GCGCCCTGAC
 501  CAGCGGCGTG CACACCTTCC CGGCTGTCCT ACAGTCCTCA GGACTCTACT
 551  CCCTCAGCAG CGTGGTGACC GTGCCCTCCA GCAGCTTGGG CACCCAGACC
 601  TACATCTGCA ACGTGAATCA CAAGCCCAGC AACACCAAGG TGGACAAGAA
 651  AGTTGAGCCC AAATCTTGTG ACAAGACTCA CACATGCCCA CCGTGCCCAG
 701  CACCTGAACT CCTGGGGGGA CCGTCAGTCT TCCTCTTCCC CCCAAAACCC
 751  AAGGACACCC TCATGATCTC CCGGACCCCT GAGGTCACAT GCGTGGTGGT
 801  GGACGTGAGC CACGAAGACC CTGAGGTCAA GTTCAACTGG TACGTGGACG
 851  GCGTGGAGGT GCATAATGCC AAGACAAAGC CGCGGGAGGA GCAGTACAAC
 901  AGCACGTACC GTGTGGTCAG CGTCCTCACC GTCCTGCACC AGGACTGGCT
 951  GAATGGCAAG GAGTACAAGT GCAAGGTCTC CAACAAAGCC CTCCCAGCCC
1001  CCATCGAGAA AACCATCTCC AAAGCCAAAG GGCAGCCCCG AGAACCACAG
1051  GTGTACACCC TGCCCCCATC CCGGGATGAG CTGACCAAGA ACCAGGTCAG
1101  CCTGACCTGC CTGGTCAAAG GCTTCTATCC CAGCGACATC GCCGTGGAGT
1151  GGGAGAGCAA TGGGCAGCCG GAGAACAACT ACAAGACCAC GCCTCCCGTG
1201  TTGGACTCCG ACGGCTCCTT CTTCCTCTAC AGCAAGCTCA CCGTGGACAA
1251  GAGCAGGTGG CAGCAGGGGA ACGTCTTCTC ATGCTCCGTG ATGCATGAGG
1301  CTCTGCACAA CCACTACACG CAGAAGAGCC TCTCCCTGTC TCCGGTTGA
```

Figure 1B

Predicted amino acid sequence of mature huCBE11 heavy chain
(SEQ ID NO. 4)

```
   1  EVQLVESGGG LVKPGGSLRL SCAASGFTFS DYYMYWFRQA PGKGLEWVAT
  51  ISDGGSYTYY PDSVKGRFTI SRDNAKNSLY LQMSSLRAED TAVYYCAREE
 101  NGNFYYFDYW GQGTTVTVSS ASTKGPSVFP LAPSSKSTSG GTAALGCLVK
 151  DYFPEPVTVS WNSGALTSGV HTFPAVLQSS GLYSLSSVVT VPSSSLGTQT
 201  YICNVNHKPS NTKVDKKVEP KSCDKTHTCP PCPAPELLGG PSVFLFPPKP
 251  KDTLMISRTP EVTCVVVDVS HEDPEVKFNW YVDGVEVHNA KTKPREEQYN
 301  STYRVVSVLT VLHQDWLNGK EYKCKVSNKA LPAPIEKTIS KAKGQPREPQ
 351  VYTLPPSRDE LTKNQVSLTC LVKGFYPSDI AVEWESNGQP ENNYKTTPPV
 401  LDSDGSFFLY SKLTVDKSRW QQGNVFSCSV MHEALHNHYT QKSLSLSPG*
```

Figure 2

CH2 domain (EU Position 231-340)

| | |
|---|---|
| 231 | APELLGG |
| 238 | PSVFLFPPKP |
| 248 | KDTLMISRTP |
| 258 | EVTCVVVDVS |
| 268 | HEDPEVKFNW |
| 278 | YVDGVEVHNA |
| 288 | KTKPREEQYN |
| 298 | STYRVVSVLT |
| 308 | VLHQDWLNGK |
| 318 | EYKCKVSNKA |
| 328 | LPAPIEKTIS |
| 338 | KAK |

CH3 domain (EU position 341-446)

| | |
|---|---|
| 341 | GQPREPQ |
| 348 | VYTLPPSRDE |
| 358 | LTKNQVSLTC |
| 368 | LVKGFYPSDI |
| 378 | AVEWESNGQP |
| 388 | ENNYKTTPPV |
| 398 | LDSDGSFFLY |
| 408 | SKLTVDKSRW |
| 418 | QQGNVFSCSV |
| 428 | MHEALHNHYT |
| 438 | QKSLSLSPG* |

Figure 3A

DNA sequence of mature huCBE11 light chain encoded by pEAG1754
(SEQ ID NO. 5)

```
  1  GATATCCAGA TGACCCAGTC TCCATCATCC TTGTCTGCAT CGGTGGGAGA
 51  CAGGGTCACT ATCACTTGCA AGGCGGGTCA GGACATTAAA AGCTATTTAA
101  GCTGGTACCA GCAGAAACCA GGGAAAGCGC CTAAGCTTCT GATCTATTAT
151  GCAACAAGGT TGGCAGATGG GGTCCCATCA AGATTCAGTG GCAGTGGATC
201  TGGTACAGAT TATACTCTAA CCATCAGCAG CCTGCAGCCT GAGGATTTCG
251  CAACTTATTA CTGTCTACAG CATGGTGAGA GCCCGTGGAC GTTCGGTGGA
301  GGCACCAAGC TGGAGATCAA ACGAACTGTG GCTGCACCAT CTGTCTTCAT
351  CTTCCCGCCA TCTGATGAGC AGTTGAAATC TGGAACTGCC TCTGTTGTGT
401  GCCTGCTGAA TAACTTCTAT CCCAGAGAGG CCAAAGTACA GTGGAAGGTG
451  GATAACGCCC TCCAATCGGG TAACTCCCAG GAGAGTGTCA CAGAGCAGGA
501  CAGCAAGGAC AGCACCTACA GCCTCAGCAG CACCCTGACG CTGAGCAAAG
551  CAGACTACGA GAAACACAAA GTCTACGCCT GCGAAGTCAC CCATCAGGGC
601  CTGAGCTCGC CCGTCACAAA GAGCTTCAAC AGGGGAGAGT GTTAG
```

Figure 3B

Predicted amino acid sequence of mature huCBE11 light chain
(SEQ ID NO. 6)

```
  1  DIQMTQSPSS LSASVGDRVT ITCKAGQDIK SYLSWYQQKP GKAPKLLIYY
 51  ATRLADGVPS RFSGSGSGTD YTLTISSLQP EDFATYYCLQ HGESPWTFGG
101  GTKLEIKRTV AAPSVFIFPP SDEQLKSGTA SVVCLLNNFY PREAKVQWKV
151  DNALQSGNSQ ESVTEQDSKD STYSLSSTLT LSKADYEKHK VYACEVTHQG
     LSSPVTKSFN RGEC*
```

Figure 4A

DNA sequence of human beta-2-microglobulin
(SEQ ID NO. 7)

```
  1  ATGTCTCGCT CCGTGGCCTT AGCTGTGCTC GCGCTACTCT CTCTTTCTGG
 51  CCTGGAGGCT ATCCAGCGTA CTCCAAAGAT TCAGGTTTAC TCACGTCATC
101  CAGCAGAGAA TGGAAAGTCA AATTTCCTGA ATTGCTATGT GTCTGGGTTT
151  CATCCATCCG ACATTGAAGT TGACTTACTG AAGAATGGAG AGAGAATTGA
201  AAAAGTGGAG CATTCAGACT TGTCTTTCAG CAAGGACTGG TCTTTCTATC
251  TCTTGTACTA CACTGAATTC ACCCCCACTG AAAAAGATGA GTATGCCTGC
301  CGTGTGAACC ATGTGACTTT GTCACAGCCC AAGATAGTTA AGTGGGATCG
351  AGACATGTAA
```

Figure 4B

Predicted amino acid sequence of human beta-2-microglobulin
(SEQ ID NO. 8)

```
  1  MSRSVALAVL ALLSLSGLEA IQRTPKIQVY SRHPAENGKS NFLNCYVSGF
 51  HPSDIEVDLL KNGERIEKVE HSDLSFSKDW SFYLLYYTEF TPTEKDEYAC
101  RVNHVTLSQP KIVKWDRDM*
```

Figure 5A

DNA sequence of human FcRn alpha-Fc fusion encoded by pEAG1761
(SEQ ID NO. 9)

```
   1  ATGGGGGTCC CGCGGCCTCA GCCCTGGGCG CTGGGGCTCC TGCTCTTTCT
  51  CCTTCCTGGG AGCCTGGGCG CAGAAAGCCA CCTCTCCCTC CTGTACCACC
 101  TTACCGCGGT GTCCTCGCCT GCCCCGGGGA CTCCTGCCTT CTGGGTGTCC
 151  GGCTGGCTGG GCCCGCAGCA GTACCTGAGC TACAATAGCC TGCGGGGCGA
 201  GGCGGAGCCC TGTGGAGCTT GGGTCTGGGA AAACCAGGTG TCCTGGTATT
 251  GGGAGAAAGA GACCACAGAT CTGAGGATCA AGGAGAAGCT CTTTCTGGAA
 301  GCTTTCAAAG CTTTGGGGGG AAAAGGTCCC TACACTCTGC AGGGCCTGCT
 351  GGGCTGTGAA CTGGGCCCTG ACAACACCTC GGTGCCCACC GCCAAGTTCG
 401  CCCTGAACGG CGAGGAGTTC ATGAATTTCG ACCTCAAGCA GGGCACCTGG
 451  GGTGGGGACT GGCCCGAGGC CCTGGCTATC AGTCAGCGGT GGCAGCAGCA
 501  GGACAAGGCG GCCAACAAGG AGCTCACCTT CCTGCTATTC TCCTGCCCGC
 551  ACCGCCTGCG GGAGCACCTG GAGAGGGCC GCGGAAACCT GGAGTGGAAG
 601  GAGCCCCCCT CCATGCGCCT GAAGGCCCGA CCCAGCAGCC TGGCTTTTC
 651  CGTGCTTACC TGCAGCGCCT CTCCTTCTA CCCTCCGGAG CTGCAACTTC
 701  GGTTCCTGCG GAATGGGCTG GCCGCTGGCA CCGGCCAGGG TGACTTCGGC
 751  CCCAACAGTG ACGGATCCTT CCACGCCTCG TCGTCACTAA CAGTCAAAAG
 801  TGGCGATGAG CACCACTACT GCTGCATTGT GCAGCACGCG GGGCTGGCGC
 851  AGCCCCTCAG GGTGGAGCTG AATCTCCAG CCAAGTCCTC CGTCGACAAA
 901  ACTCACACAT GCCCACCGTG CCCAGCACCT GAACTCCTGG GGGGACCGTC
 951  AGTCTTCCTC TTCCCCCCAA AACCCAAGGA CACCCTCATG ATCTCCCGGA
1001  CCCCTGAGGT CACATGCGTG GTGGTGGACG TGAGCCACGA AGACCCTGAG
1051  GTCAAGTTCA ACTGGTACGT GGACGGCGTG GAGGTGCATA ATGCCAAGAC
1101  AAAGCCGCGG GAGGAGCAGT ACAACAGCAC GTACCGTGTG GTCAGCGTCC
1151  TCACCGTCCT GGCTAACGAC TGGCTGAATG GCAAGGAGTA CAAGTGCAAG
1201  GTCTCCAACA AAGCCCTCCC AGCCCCATC GAGAAAACCA TCTCCAAAGC
1251  CAAAGGGCAG CCCCGAGAAC CACAGGTGTA CACCCTGCCC CCATCCCGGG
1301  ATGAGCTGAC CAAGAACCAG GTCAGCCTGA CCTGCCTGGT CAAAGGCTTC
1351  TATCCCAGCG ACATCGCCGT GGAGTGGGAG AGCAATGGGC AGCCGGAGAA
1401  CAACTACAAG ACCACGCCTC CCGTGTTGGA CTCCGACGGC TCCTTCTTCC
1451  TCTACAGCAA GCTCACCGTG GACAAGAGCA GGTGGCAGCA GGGGAACGTC
1501  TTCTCATGCT CCGTGATGCA TGAGGCTCTG CGCAGCACT ACACGCAGAA
1551  GAGCCTCTCC CTGTCTCCGG GTTGA
```

Figure 5B

Predicted amino acid sequence of human FcRn alpha-Fc fusion
protein (SEQ ID NO. 10)

```
  1  MGVPRPQPWA LGLLLFLLPG SLGAESHLSL LYHLTAVSSP APGTPAFWVS
 51  GWLGPQQYLS YNSLRGEAEP CGAWVWENQV SWYWEKETTD LRIKEKLFLE
101  AFKALGGKGP YTLQGLLGCE LGPDNTSVPT AKFALNGEEF MNFDLKQGTW
151  GGDWPEALAI SQRWQQQDKA ANKELTFLLF SCPHRLREHL ERGRGNLEWK
201  EPPSMRLKAR PSSPGFSVLT CSAFSFYPPE LQLRFLRNGL AAGTGQGDFG
251  PNSDGSFHAS SSLTVKSGDE HHYCCIVQHA GLAQPLRVEL ESPAKSSVDK
301  THTCPPCPAP ELLGGPSVFL FPPKPKDTLM ISRTPEVTCV VVDVSHEDPE
351  VKFNWYVDGV EVHNAKTKPR EEQYNSTYRV VSVLTVLAND WLNGKEYKCK
401  VSNKALPAPI EKTISKAKGQ PREPQVYTLP PSRDELTKNQ VSLTCLVKGF
451  YPSDIAVEWE SNGQPENNYK TTPPVLDSDG SFFLYSKLTV DKSRWQQGNV
501  FSCSVMHEAL AQHYTQKSLS LSPG*
```

Figure 9
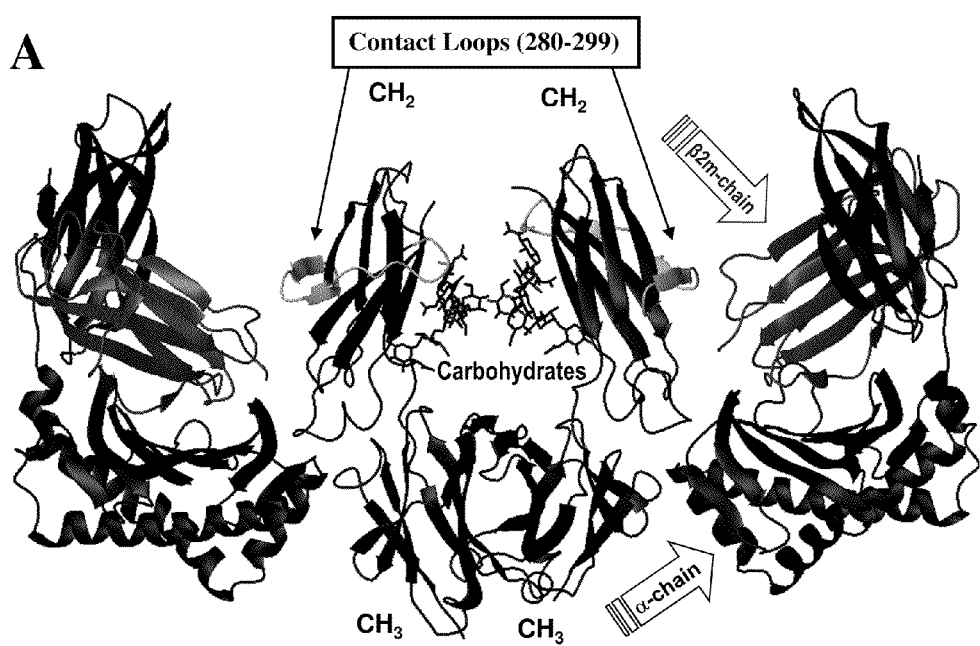
A
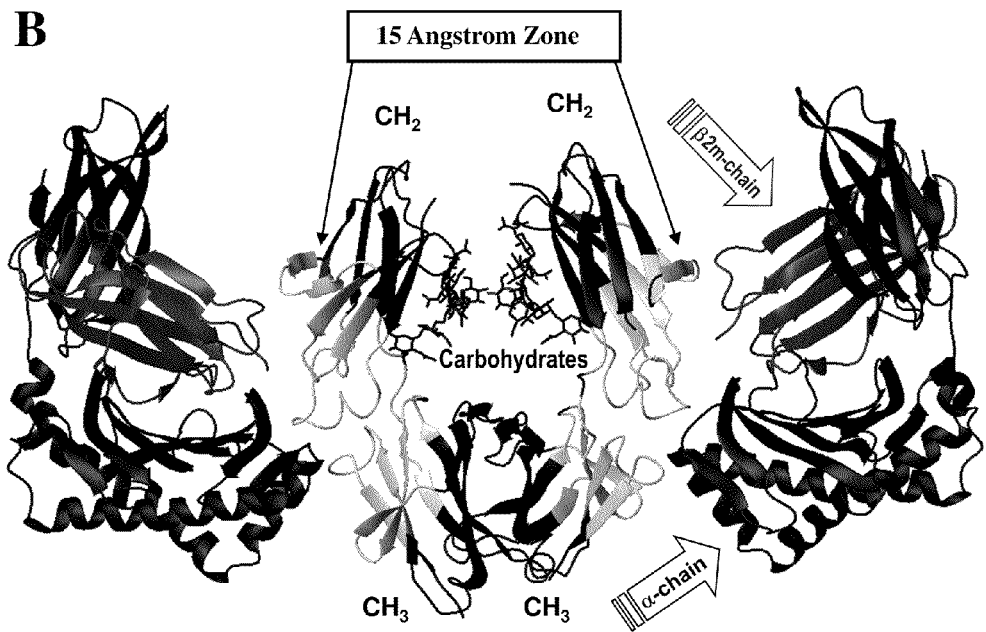
B

US 8,618,252 B2

NEONATAL FC RECEPTOR (FCRN)-BINDING POLYPEPTIDE VARIANTS, DIMERIC FC BINDING PROTEINS AND METHODS RELATED THERETO

RELATED APPLICATIONS

This application is a continuation of U.S. application Ser. No. 11/432,872, filed May 12, 2006, (Abandoned), which is a continuation application of International Patent Application No. PCT/US2004/037929, filed Nov. 12, 2004, which claims the benefit of U.S. Provisional application Ser. No. 60/519,744, filed on Nov. 12, 2003 and U.S. Application Ser. No. 60/519,743, filed on Nov. 12, 2003. This application also claims the benefit of U.S. Application Ser. No. 60/519,733, filed on Nov. 12, 2003. This application is also related to PCT application PCT/US2004/037948, filed on Nov. 12, 2004. The contents of any patents, patent applications, and references cited throughout this specification are hereby incorporated by reference in their entireties.

BACKGROUND OF THE INVENTION

Many biological processes are mediated by the specific interaction of one protein with another. For example, enzymes are proteins that specifically bind their substrates, and substantial information is transmitted from cell to cell when ligands (such as neurotransmitters and hormones) bind their cognate receptors. Among the most fascinating interactions are those that occur in the context of an immune response in which antibodies (also known as immunoglobulins) are produced to defend the body against foreign substances that can cause infection or disease. Antibodies contain distinct domains that specifically interact with antigens and with receptors on "effector" cells, such as phagocytes. While binding the antigen is useful (in that it can prevent the antigen from interacting with its endogenous target), the most effective immune responses destroy antigens. Thus, the most effective antibodies are those with a domain that mediates high affinity antigen-binding and a domain that mediates efficient effector functions.

Naturally occurring antibodies are usually heterotetrameric; they contain two identical light (L) chains and two identical heavy (H) chains, linked together by disulfide bonds. Each heavy chain has a variable domain ($V_H$) followed by a number of constant domains ($CH_1$, $CH_2$, and $CH_3$), while each light chain has a variable domain ($V_L$) followed by a single constant domain. The constant domain of the light chain is aligned with the first constant domain of the heavy chain, and $V_L$ is aligned with $V_H$. The variable domains are so named because certain amino acids within them differ extensively among antibodies. These variable regions, also called complementarity determining regions (CDRs) are responsible for the binding specificity of each particular antibody for its particular antigen. Each variable domain contains three CDRs separated by highly conserved regions called framework regions (FRs). The CDRs in each chain are held together in close proximity by the FR regions and, with the CDRs from the other chain, contribute to the formation of the antigen binding site of antibodies.

The constant domains are not involved directly in binding an antibody to an antigen, but mediate various effector functions based on their binding to cellular receptor or complement molecules. Depending on the amino acid sequence of the constant region of their heavy chains, antibodies or immunoglobulins can be assigned to different classes (A, D, E, G, and M). The most commonly used therapeutic antibodies are of the "G" class (i.e., they are IgGs). These classes can be further divided. For example, IgG antibodies are further divided into the isotypes IgG1, IgG2, IgG3, and IgG4. The crystal structure of the human IgG Fc region has been determined (Deisenhofer, *Biochemistry* 20:2361-2370, 1981; for an illustration of the Fc region see FIG. 1 of U.S. Pat. No. 6,242,195).

The Fc region mediates effector functions that have been divided into two categories. In the first are the functions that occur independently of antigen binding; these functions confer persistence in the circulation and the ability to be transferred across cellular barriers by transcytosis (see Ward and Ghetie, *Therapeutic Immunology* 2:77-94, 1995). In the second are the functions that operate after an antibody binds an antigen; these functions involve the participation of the complement cascade or Fc receptor (FcR)-bearing cells. FcRs are specialized cell surface receptors on hematopoietic cells that mediate both the removal of antibody-coated pathogens by phagocytosis of immune complexes, and the lysis of erythrocytes and various other cellular targets (e.g. tumor cells) coated with the corresponding antibody. Lysis occurs via antibody dependent cell mediated cytotoxicity (ADCC; see Van de Winkel and Anderson, *J. Leuk. Biol.* 49:511-24, 1991). FcRs are defined by their specificity for immunoglobulin isotypes. For example, Fc receptors for IgG antibodies are referred to as FcγR.

Another Fc receptor, FcRn, regulates the serum half-lives of IgGs. Enhancement or diminishment of the half-life of the Fc (or Fc-containing polypeptide) is reflected, respectively, in the increase or decrease of the Fc region affinity for FcRn (neonatal Fc receptor) (Ghetic et al., *Nature Biotechnol.* 15:637-640, 1997; Kim et. al., *Eur. J. Immunol.* 24:542-548, 1994; Della'Acqua et al. (*J. Immunol.* 169:5171-5180, 2002). The correlation of FcRn binding affinity and serum half-life is consistent with its proposed biological role in salvaging an antibody from lysosomal degradation. In addition, FcRn transfers IgGs from mother to fetus.

These apparently diverse roles are mediated by the ability of FcRn to transport bound IgG within and across cells. It is thought that antibodies are normally internalized from circulation by endothelial cells and are targeted to the acidic endosomes and lysosomes of the cells for degradation. FcRn is capable of binding the Fc region of an antibody at the acidic pH of an endosome (<6.5), fusing with the endothelial cell membrane, and releasing the antibody at the neutral pH of the bloodstream (>7.4), thereby salvaging the antibody from destruction. When serum antibody levels decrease, more FcRn molecules are available for IgG binding so that an increased amount of IgG is salvaged. Conversely, if serum IgG levels rise, FcRn becomes saturated, thereby increasing the proportion of antibody that is internalized and degraded (Ghetie and Ward, Annu. Rev. Immunol., (2000), 18: 739-66). Consistent with the above model, an altered polypeptide is predicted to have a longer half-life if its binding affinity for a neonatal Fc receptor is increased. Conversely, the altered polypeptide is predicted to have a shorter half-life it its binding affinity for a neonatal Fc receptor is decreased.

Monoclonal antibodies (mAbs) have now been used to treat disease in human patients (King and Adair, *Curr. Opin. Drug Discovery Dev.* 2:110-117, 1999; Vaswani and Hamilton, *Ann. Allergy Asthma Immunol.* 81:105-119, 1998; and Hollinger and Hoogenboom, *Nature Biotechnol.* 16:1015-1016, 1998). This is not to say that present antibody-based therapies have been entirely successful; in some instances, the limited circulation time and/or low bioavailability of a therapeutic results in a relatively low percentage of patients that exhibit a complete response to an antibody-based therapeutics, or in other cases toxicity due to prolonged circulatory half-life or exposure of non-target tissue may preclude use of the antibody as a therapy.

Accordingly, there is a need for antibodies (and other Fc-containing polypeptides such as fusion proteins) where the antigen-independent effector functions are tailored for the intended use of the antibody. Similarly, there is a need for methods that would allow for prediction of changes in antibody sequence which will alter the antigen-independent effector functions (thus obviating the need to rely on laborious trial-and-error processes). In some cases, it may be desirable to increase the half-life of the antibody. For example, protein therapeutics with an increased half-life in the blood have the advantage of concurrently decreasing the periodic dosing of the drug or alternatively to decrease the dose of the drug. Such antibodies also have the advantage of increased exposure to a disease site, e.g. a tumor. Conversely, protein therapeutics with a decreased half-life would be expected to have lower toxicity, while maintaining the efficacy that, is observed with a higher and less tolerable dose of the unaltered drug. Such therapeutics and methods or making them would be of great benefit.

SUMMARY OF THE INVENTION

The present invention features altered polypeptides having specific amino acid substitutions within, for example, an Fc region or an FcRn binding fragment thereof (e.g. polypeptides having amino acid substitutions within an IgG constant domain), that confer alterations in antigen-independent effector function (e.g. circulating half-life). Methods for producing the altered polypeptides and utilizing them as protein-based therapeutics are also provided. The invention further provides novel forms of FcRn and methods of their use.

The present invention is based, at least in part, on the identification of particular amino acid residues within the constant domain (Fc) of human Fc region (specifically, Fc region derived from the IgG antibodies) that, when altered by one or more amino acid mutations, alter the antigen-independent effector functions of the antibody, in particular the circulating half-life of the antibody. Accordingly, the invention features polypeptides, e.g., antibodies and fusion proteins that contain all or part of an Fc region, that have been mutated at one or more amino acid residues to increase or decrease the antigen-independent effector functions of the polypeptide.

The instant invention further provides techniques for identifying desirable amino acid mutations and methods for producing the polypeptides comprising such mutations. The methods include molecular modeling, which can be used to predict amino acid alterations in an amino acid sequence to alter (e.g., enhance or reduce) binding to an Fc receptor, e.g. a human neonatal Fc receptor. Generally, the methods begin with a "starting" or "target" polypeptide, or a complex (e.g. crystal structure or homology model) containing the first polypeptide bound to FcRn, and modification of the first polypeptide results in a "second" or "altered" polypeptide, which differs from the first polypeptide in a way that allows the altered polypeptide to perform better in a particular therapeutic or diagnostic application. For example, the second polypeptide may more efficiently carry out one or more antigen-independent effector functions (e.g. altered half-life). The modeling can be carried out in silico.

In one aspect, the invention pertains to an altered polypeptide comprising at least an FcRn binding portion of an Fc region wherein said polypeptide comprises at least one mutation compared to a starting polypeptide and wherein the at least one mutation is selected from the group consisting of:

a substitution at EU amino acid position 248 with a charged amino acid;
a substitution at EU amino acid position 249 with a positively charged amino acid;
a substitution at EU amino acid position 251 with a polar amino acid or lysine;
a substitution at EU amino acid position 252 with a polar amino acid;
a substitution at EU amino acid position 255 with a polar amino acid;
a substitution at EU amino acid position 256 with lysine;
a substitution at EU amino acid position 257 with a charged amino acid;
a substitution at EU amino acid position 258 with a polar amino acid or a charged amino acid;
a substitution at EU amino acid position 277;
a substitution at EU amino acid position 279 with a charged amino acid;
a substitution at EU amino acid position 280 with a charged amino acid;
a substitution at EU amino acid position 281 with a charged amino acid or glutamine;
a substitution at EU amino acid position 282 with a charged amino acid;
a substitution at EU amino acid position 284 with a polar amino acid or a charged amino acid;
a substitution at EU amino acid position 285 with a positively charged amino acid, a polar amino acid, or aspartate;
a substitution at EU amino acid position 286 with glutamate, threonine, or methionine;
a substitution at EU amino acid position 287 with a polar amino acid or a charged amino acid;
a substitution at EU amino acid position 288 with a charged amino acid;
a substitution at EU amino acid position 289;
a substitution at EU amino acid position 304 with a polar amino acid or a charged amino acid;
a substitution at EU amino acid position 305 with a polar amino acid or a charged amino acid;
a substitution at EU amino acid position 306;
a substitution at EU amino acid position 307 with a polar or charged amino acid;
a substitution at EU amino acid position 308 with a charged amino acid;
a substitution at EU amino acid position 309 with a charged amino acid;
a substitution at EU amino acid position 310 with a charged amino acid or a polar amino acid;
a substitution at EU amino acid position 311 with a positively charged amino acid;
a substitution at EU amino acid position 312 with a positively charged amino acid or a polar amino acid;
a substitution at EU amino acid position 313 with a charged amino acid;
a substitution at EU amino acid position 315 with a charged amino acid;
a substitution at EU amino acid position 316 with a positively charged amino acid;
a substitution at EU amino acid position 317 with a charged amino acid or a polar amino acid;
a substitution at EU amino acid position 340 with a charged amino acid;
a substitution at EU amino acid position 343 with a polar amino acid or a charged amino acid;
a substitution at EU amino acid position 344 with leucine;
a substitution at EU amino acid position 345 with a polar amino acid or a charged amino acid;

a substitution at EU amino acid position 376 with a polar amino acid or a charged amino acid;

a substitution at EU amino acid position 378 with serine;

a substitution at EU amino acid position 383 with a charged amino acid;

a substitution at EU amino acid position 385 with a charged amino acid;

a substitution at EU amino acid position 389 with a negatively charged amino acid;

a substitution at EU amino acid position 424 with a charged amino acid;

a substitution at EU amino acid position 426 with a charged amino acid;

a substitution at EU amino acid position 430 with a polar amino acid or a charged amino acid;

a substitution at EU amino acid position 431 with a charged amino acid;

a substitution at EU amino acid position 432 with a polar amino acid;

a substitution at EU amino acid position 434 with lysine, arginine, or leucine;

a substitution at EU amino acid position 436 with a negatively charged amino acid; and a substitution at EU amino acid position 438 with a charged amino acid.

In another aspect, the invention pertains to altered polypeptide comprising at least an FcRn binding portion of an Fc region wherein said polypeptide comprises at least one mutation compared to a starting polypeptide and wherein the at least one mutation is selected from the group consisting of:

a substitution of lysine at EU amino acid position 248 with a charged amino acid;

a substitution of aspartate at EU amino acid position 249 with a positively charged amino acid;

a substitution at leucine at EU amino acid position 251 with a polar amino acid or lysine;

a substitution of methionine at EU amino acid position 252 a substitution of arginine at EU amino acid position 255 with a polar amino acid;

a substitution of threonine at EU amino acid position 256 with lysine;

a substitution of proline at EU amino acid position 257 with a charged amino acid;

a substitution of glutamate at EU amino acid position 258 with a polar amino acid or a charged amino acid;

a substitution of tryptophan at EU amino acid position 277;

a substitution of valine at EU amino acid position 279 with a charged amino acid;

a substitution of aspartate at EU amino acid position 280 with a charged amino acid;

a substitution of glycine at EU amino acid position 281 with a charged amino acid or glutamine;

a substitution of valine at EU amino acid position 282 with a charged amino acid;

a substitution of valine at EU amino acid position 284 with a polar amino acid or a charged amino acid;

a substitution histidine or alanine at EU amino acid position 285 with a charged amino acid or a polar amino acid;

a substitution histidine or alanine at EU amino acid position 285 with a positively charged amino acid, a polar amino acid, or aspartate;

a substitution of asparagine or lysine at EU amino acid position 286 with glutamate, threonine, or methionine;

a substitution of alanine at EU amino acid position 287 with a polar amino acid or a charged amino acid;

a substitution of lysine at EU amino acid position 288 with a charged amino acid;

a substitution of threonine at EU amino acid position 289;

a substitution of serine at EU amino acid position 304 with a polar amino acid or a charged amino acid;

a substitution of valine at EU amino acid position 305 with a polar amino acid or a charged amino acid;

a substitution of leucine or valine at EU amino acid position 306;

a substitution of threonine or valine at EU amino acid position 307 with a polar or charged amino acid;

a substitution of valine at EU amino acid position 308 with a charged amino acid;

a substitution of leucine at EU amino acid position 309 with a charged amino acid;

a substitution of histidine at EU amino acid position 310 with a charged amino acid or a polar amino acid;

a substitution of glutamine at EU amino acid position 311 with a positively charged amino acid;

a substitution of aspartate or leucine at EU amino acid position 312 with a positively charged amino acid or a polar amino acid;

a substitution of asparagine at EU amino acid position 313 with a charged amino acid;

a substitution of asparagine at EU amino acid position 315 with a charged amino acid;

a substitution of asparagine at EU amino acid position 316 with a positively charged amino acid;

a substitution of lysine at EU amino acid position 317 with a charged amino acid or a polar amino acid;

a substitution of lysine at EU amino acid position 340 with a charged amino acid;

a substitution of proline at EU amino acid position 343 with a polar amino acid or a charged amino acid;

a substitution of arginine at EU amino acid position 344 with leucine;

a substitution of glutamate at EU amino acid position 345 with a polar amino acid or a charged amino acid;

a substitution of aspartate at EU amino acid position 376 with a polar amino acid or a charged amino acid;

a substitution of alanine at EU amino acid position 378 with serine;

a substitution of serine at EU amino acid position 383 with a charged amino acid;

a substitution of glycine at EU amino acid position 385 with a charged amino acid;

a substitution of asparagine at EU amino acid position 389 with a negatively charged amino acid;

a substitution of serine at EU amino acid position 424 with a charged amino acid;

a substitution of serine at EU amino acid position 426 with a charged amino acid;

a substitution of glutamate at EU amino acid position 430 with a polar amino acid or a charged amino acid;

a substitution of leucine at EU amino acid position 431 with a charged amino acid;

a substitution of histidine at EU amino acid position 432 with a polar amino acid;

a substitution of asparagine at EU amino acid position 434 with lysine, arginine, or leucine;

a substitution of tyrosine at EU amino acid position 436 with a negatively charged amino acid; and a substitution of glutamine at EU amino acid position 438 with a charged amino acid.

In another aspect, the invention pertains to an altered polypeptide wherein the amino acid at least one of EU amino acid positions 277, 289, 306, 344, or 378 is replaced with a charged amino acid, a polar amino acid, or a nonpolar amino acid.

In one embodiment, the charged amino acid is a negatively charged amino acid.

In one embodiment, the negatively charged amino acid is selected from the group consisting of aspartate and glutamate.

In one embodiment, the charged amino acid is a positively charged amino acid.

In one embodiment, the positively charged amino acid is selected from the group consisting of arginine, histidine, and lysine.

In one embodiment, the positively charged amino acid is lysine.

In one embodiment, the polar amino acid is selected from the group consisting of methionine, phenylalanine, tryptophan, serine, threonine, tyrosine, asparagine, glutamine, and cysteine.

In one embodiment, the nonpolar amino acid is selected from the group consisting of alanine, leucine, isoleucine, valine, glycine, and proline.

In one embodiment, the altered polypeptide is an antibody or fragment thereof.

In one embodiment, the altered polypeptide is a fusion protein.

In one embodiment, the Fc region or the FcRn binding portion thereof is derived from a human antibody.

In one embodiment, the polypeptide comprises a complete Fc region.

In one embodiment, the starting polypeptide comprises the amino acid sequence of SEQ ID NO:2.

In one embodiment, the Fc region or Fc binding portion thereof is of the IgG isotype.

In one embodiment, the IgG isotype is of the IgG1 subclass.

In one embodiment, the polypeptide comprises one or more non-human amino acids residues in a complementarity determining region (CDR) of $V_L$ or $V_H$.

In one embodiment, the polypeptide binds (a) an antigen and (b) an FcR.

In one embodiment, the antigen is a tumor-associated antigen.

In one embodiment, the polypeptide binds (a) a ligand and (b) an FcR.

In one embodiment, the FcR is FcRn.

In one embodiment, the polypeptide binds the FcR with different binding affinity compared to the starting polypeptide that does not contain the mutation.

In one embodiment, the binding affinity of the altered polypeptide is about 1.5-fold to about 100-fold greater than the starting polypeptide.

In one embodiment, the binding affinity of the altered polypeptide is about 1.5-fold to about 100-fold lower than the starting polypeptide.

In one embodiment, the altered polypeptide exhibits one binding affinity for the FcR at a first pH, and exhibits a different binding affinity for the FcR at a second pH.

In one embodiment, the binding affinity of the altered polypeptide is about 1.5-fold to about 100-fold greater at the first pH than the second pH.

In one embodiment, the binding affinity of the altered antibody is about 1.5-fold to about 100-fold lower at the first pH than the second pH.

In one embodiment, the altered polypeptide, when administered to a patient, exhibits a circulatory half-life that is different from the starting polypeptide that does not contain the mutation.

In one embodiment, the half-life of the altered polypeptide is about 1 hour to about 1 week longer than the starting polypeptide that does not contain the mutation.

In one embodiment, the half-life of the altered polypeptide is about 1 hour to about 1 week shorter than the starting polypeptide that does not contain the mutation.

In one embodiment, the altered polypeptide binds to Protein A or G

In one embodiment, the invention pertains to a nucleotide sequence encoding a polypeptide of the invention.

In one embodiment, the nucleic acid is in an expression vector.

In one embodiment, the expression vector is in a host cell.

In one embodiment, the invention pertains to a method for treating a patient suffering from a disorder, the method comprising administering to the patient an altered polypeptide comprising at least an FcRn binding portion of an Fc region comprising at least one mutation selected from the group consisting of:

a substitution at EU amino acid position 284 with glutamate;

a substitution at EU amino acid position 285 with glutamate;

a substitution at EU amino acid position 286 with aspartate;

a substitution at EU amino acid position 288 with glutamate or aspartate;

a substitution at EU amino acid position 290 with glutamate; and a substitution at EU amino acid position 304 with aspartate, wherein the altered polypeptide exhibits a circulatory half-life than is longer than the starting polypeptide that does not contain the mutation.

In one embodiment, the invention pertains to a method for treating a patient suffering from a disorder, the method comprising administering to the patient an altered polypeptide comprising at least an FcRn binding portion of an Fc region comprising at least one mutation selected from the group consisting of:

a substitution of valine at EU amino acid position 284 with glutamate;

a substitution of histidine at EU amino acid position 285 with glutamate;

a substitution of asparagine at EU amino acid position 286 with aspartate;

a substitution of lysine at EU amino acid position 288 with glutamate or aspartate;

a substitution of lysine at EU amino acid position 290 with glutamate; and a substitution of serine at EU amino acid position 304 with aspartate, wherein the altered polypeptide exhibits a circulatory half-life than is longer than the starting polypeptide that does not contain the mutation.

In one embodiment, the invention pertains to a method for treating a patient suffering from a disorder, the method comprising administering to the patient an altered polypeptide comprising at least an FcRn binding portion of an Fc region comprising at least one mutation selected from the group consisting of:

a substitution at EU amino acid position 248 with aspartate;

a substitution at EU amino acid position 249 with arginine or lysine;

a substitution at EU amino acid position 250 with arginine or lysine;

a substitution at EU amino acid position 251 with arginine, lysine, or asparagine;

a substitution at EU amino acid position 252 with serine or threonine;

a substitution at EU amino acid position 254 with serine or threonine;
a substitution at EU amino acid position 256 with arginine, glutamate, or lysine;
a substitution at EU amino acid position 255 with leucine, aspartate or methionine;
a substitution at EU amino acid position 260 with lysine;
a substitution at EU amino acid position 257 with arginine, aspartate, glutamate, or lysine;
a substitution at EU amino acid position 277 with arginine, aspartate, glutamine, or lysine;
a substitution at EU amino acid position 279 with glutamate;
a substitution at EU amino acid position 281 with glutamine;
a substitution at EU amino acid position 282 with arginine, aspartate, glutamate, or lysine;
a substitution at EU amino acid position 287 with aspartate, glutamate, lysine, proline, or threonine;
a substitution at EU amino acid position 284 with aspartate;
a substitution at EU amino acid position 285 with aspartate or phenylalanine;
a substitution at EU amino acid position 286 with glutamate or methionine;
a substitution at EU amino acid position 288 with aspartate;
a substitution at EU amino acid position 290 with aspartate;
a substitution at EU amino acid position 304 with aspartate or glutamate;
a substitution at EU amino acid position 305 with arginine;
a substitution at EU amino acid position 306 with arginine, aspartate, glutamate, or lysine;
a substitution at EU amino acid position 307 with arginine, aspartate, or glutamate;
a substitution at EU amino acid position 309 with arginine, aspartate, lysine or glutamate;
a substitution at EU amino acid position 310 with arginine, leucine, lysine or asparagine;
a substitution at EU amino acid position 312 with arginine, asparagine, or lysine;
a substitution at EU amino acid position 313 with aspartate, arginine, or lysine;
a substitution at EU amino acid position 315 with aspartate or glutamate;
a substitution at EU amino acid position 343 with glutamine or lysine;
a substitution at EU amino acid position 345 with arginine or glutamine;
a substitution at EU amino acid position 374 with arginine, lysine, or leucine;
a substitution at EU amino acid position 376 with asparagine;
a substitution at EU amino acid position 426 with arginine, aspartate, or glutamate;
a substitution at EU amino acid position 428 with arginine, glutamine, or lysine;
a substitution at EU amino acid position 430 with lysine;
a substitution at EU amino acid position 431 with proline;
a substitution at EU amino acid position 432 with arginine;
a substitution at EU amino acid position 434 with lecuine or lysine; and
a substitution at EU amino acid position 438 with glutamate wherein the altered polypeptide exhibits a circulatory half-life than is shorter than the starting polypeptide that does not contain the mutation.

In another aspect, the invention pertains to a method for treating a patient suffering from a disorder, the method comprising administering to the patient an altered polypeptide comprising at least an FcRn binding portion of an Fc region comprising at least one mutation selected from the group consisting of:
a substitution of lysine at EU amino acid position 248 with aspartate;
a substitution of aspartate at EU amino acid position 249 with arginine or lysine;
a substitution of threonine at EU amino acid position 250 with arginine or lysine;
a substitution of leucine at EU amino acid position 251 with arginine, lysine, or asparagine;
a substitution of methionine at EU amino acid position 252 with serine or threonine;
a substitution of methionine at EU amino acid position 254 with serine or threonine;
a substitution of threonine at EU amino acid position 256 with arginine, glutamate, or lysine;
a substitution of arginine at EU amino acid position 255 with leucine, aspartate or methionine;
a substitution of threonine at EU amino acid position 260 with lysine;
a substitution of proline at EU amino acid position 257 with arginine, aspartate, glutamate, or lysine;
a substitution of tryptophan at EU amino acid position 277 with arginine, aspartate, glutamine, or lysine;
a substitution of valine at EU amino acid position 279 with glutamate;
a substitution of glycine at EU amino acid position 281 with glutamine;
a substitution of valine at EU amino acid position 282 with arginine, aspartate, glutamate, or lysine;
a substitution of alanine at EU amino acid position 287 with aspartate, glutamate, lysine, proline, or threonine;
a substitution of valine at EU amino acid position 284 with aspartate;
a substitution of histidine at EU amino acid position 285 with aspartate or phenylalanine;
a substitution of asparagine at EU amino acid position 286 with glutamate or methionine;
a substitution of lysine at EU amino acid position 288 with aspartate;
a substitution of lysine at EU amino acid position 290 with aspartate;
a substitution of serine at EU amino acid position 304 with aspartate or glutamate;
a substitution of valine at EU amino acid position 305 with arginine;
a substitution of leucine at EU amino acid position 306 with arginine, aspartate, glutamate, or lysine;
a substitution of threonine at EU amino acid position 307 with arginine, aspartate, or glutamate;
a substitution of leucine at EU amino acid position 309 with arginine, aspartate, lysine or glutamate;
a substitution of histidine at EU amino acid position 310 with arginine, leucine, lysine or asparagine;
a substitution of aspartate at EU amino acid position 312 with arginine, asparagine, or lysine;
a substitution of tryptophan at EU amino acid position 313 with aspartate, arginine, or lysine;
a substitution of asparagine at EU amino acid position 315 with aspartate or glutamate;

a substitution of proline at EU amino acid position 343 with glutamine or lysine;

a substitution of glutamate at EU amino acid position 345 with arginine or glutamine;

a substitution of proline at EU amino acid position 374 with arginine, lysine, or leucine;

a substitution of aspartate at EU amino acid position 376 with asparagine;

a substitution of serine at EU amino acid position 426 with arginine, aspartate, or glutamate;

a substitution of methionine at EU amino acid position 428 with arginine, glutamine, or lysine;

a substitution of glutamate at EU amino acid position 430 with lysine;

a substitution of alanine at EU amino acid position 431 with proline;

a substitution of leucine at EU amino acid position 432 with arginine;

a substitution of asparagine at EU amino acid position 434 with leucine or lysine; and a substitution of glutamine at EU amino acid position 438 with glutamate wherein the altered polypeptide exhibits a circulatory half-life than is shorter than the starting polypeptide that does not contain the mutation.

In one embodiment, the invention pertains to a method of producing an altered polypeptide of the invention method comprising:

(a) transfecting a cell with the nucleic acid molecule comprising a nucleotide sequence that encodes the altered polypeptide; and (b) purifying the altered polypeptide from the cell or cell supernatant.

In one embodiment, the invention pertains to a method of producing an antibody of the invention, the method comprising:

(a) providing a first nucleic acid molecule comprising a nucleotide sequence that encodes the variable ($V_L$) and constant regions ($C_L$) of the antibody's light chain;

(b) providing a second nucleic acid molecule comprising a nucleotide sequence that encodes the variable ($V_H$) and constant regions ($CH_1$, $CH_2$, and $CH_3$) of the antibody's heavy chain;

(c) transfecting a cell with the first and second nucleic acid molecules under conditions that permit expression of the altered antibody comprising the encoded light and heavy chains; and (d) purifying the antibody from the cell or cell supernatant.

In one embodiment, the cell is a 293 cell.

In one embodiment, the invention pertains to a dimeric Fc binding protein comprising a first and second polypeptide chains, wherein the first and the second polypeptide chains each comprise at least one Fc region domain operably linked to an Fc binding domain.

In one embodiment, said Fc domain is mutated to reduce or eliminate binding to FcRn.

In one embodiment, said first and second polypeptide chains are covalently linked.

In one embodiment, the Fc binding domain comprises the extracellular domain of FcRn.

In one embodiment, the Fc binding domain is bound to beta-2-microglobulin.

In one embodiment, the Fc binding domain is derived from human FcRn.

In one embodiment, the binding protein comprises the amino acid sequence shown in SEQ ED NO:10.

In one embodiment, the invention pertains to a method for measuring binding affinity of polypeptide comprising at least an FcRn binding portion of an Fc region for an FcR, the method comprising contacting a polypeptide comprising at least an FcRn binding portion of an Fc region with a dimeric Fc binding protein of the invention and determining the affinity of the interaction.

In one embodiment, the invention pertains to a method for screening a library of polypeptides which comprise at least an FcRn binding portion of an Fc region for those polypeptides having an altered binding affinity for FcRn, the method comprising (a) contacting members of the library with a dimeric Fc binding protein of the invention; and (b) measuring the binding affinity of the polypeptides for the dimeric Fc binding protein; and (c) selecting those polypeptides which have altered binding affinity or FcRn.

In one embodiment, the invention pertains to a method for purifying a polypeptide at least an FcRn binding portion of an Fc region from a mixture of polypeptides, the method comprising applying the mixture to an affinity column containing a dimeric Fc binding protein of the invention, eluting the polypeptide comprising at least an FcRn binding portion of an Fc region such that the polypeptide is purified.

In one embodiment, the mixture is applied to the affinity column at a first pH and the polypeptide is eluted from the affinity column at a second pH.

In one embodiment the polypeptide is not denatured during the purification process.

In one embodiment, the invention pertains to a method for identifying a polypeptide with an altered binding affinity for FcRn compared to a starting polypeptide, the method comprising:

(a) determining a spatial representation of an optimal charge distribution of the amino acids of the starting polypeptide and an associated change in binding free energy of the starting polypeptide when bound to FcRn in a solvent;

(b) identifying at least one candidate amino acid residue position of the starting polypeptide to be modified to alter the binding free energy of the starting polypeptide when bound to FcRn; and (c) identifying an elected amino acid at the amino acid position, such that incorporation of the mutation in the starting polypeptide results in an altered polypeptide with an altered binding affinity for FcRn.

In one embodiment the method further comprises incorporating the elected amino acid in the starting polypeptide.

In one embodiment the method further comprises urther comprising calculating the change in the free energy of binding of the altered Fc-containing polypeptide when bound to the FcRn, as compared to the starting polypeptide when bound to the FcRn.

In one embodiment, the calculating step first comprises modeling the mutation in the starting polypeptide in silico, and then calculating the change in free energy of binding.

In one embodiment, the calculating step uses at least one determination selected from the group consisting of a determination of the electrostatic binding energy using a method based on the Poisson-Boltzmann equation, a determination of the van der Waals binding energy, and a determination of the binding energy using a method based on solvent accessible surface area.

In one embodiment, the mutation is an amino acid substitution.

In one embodiment, the amino acid substitution results in incorporation of an elected amino acid with a different charge than the candidate amino acid.

In one embodiment, the mutation increases the free energy of binding between altered Fc-containing polypeptide and FcRn when bound in a solvent, thereby decreasing binding affinity of the altered Fc-containing polypeptide for FcRn.

In one embodiment, the mutation decreases the free energy of binding between altered Fc-containing polypeptide and FcRn when bound in a solvent, thereby increasing binding affinity of the altered Fc-containing polypeptide for FcRn.

In one aspect, the invention pertains to a method for identifying an altered Fc-containing polypeptide with an altered binding affinity for FcRn at two different pH levels, the method comprising:

(a) determining a spatial representation of an optimal charge distribution of the amino acids of the starting polypeptide and an associated change in binding free energy of the starting polypeptide when bound to FcRn in a solvent at a first pH level;

(b) determining a spatial representation of an optimal charge distribution of the amino acids of the starting polypeptide and an associated change in binding free energy of the starting polypeptide when bound to FcRn in a solvent at a second pH level;

(c) identifying, based on a comparison of the charge distributions, residues that exhibit different charge distributions at the first and second pH levels, at least one candidate amino acid residue position of the starting polypeptide to be modified to alter the binding free energy of the starting polypeptide when bound to FcRn; and (d) selecting an elected amino acid at said amino acid position, such that incorporation of the elected amino acid in the starting polypeptide results in an altered Fc-containing polypeptide with an altered binding affinity for FcRn.

In one embodiment, the first pH is about 7.4.

In one embodiment, the affinity of a polypeptide is about 1.5-fold to about 100-fold greater at the first pH than at the second pH.

The details of one or more embodiments of the invention are set forth in the accompanying drawings and the description below. Other features, objects, and advantages of the invention will be apparent from the description and drawings, and from the claims. The contents of any patents, patent applications, and other references cited in our specification are hereby incorporated by reference in their entirety.

BRIEF DESCRIPTION OF THE FIGURES

FIG. 1A shows the DNA sequence of mature huCBE11 heavy chain utilized as a starting polypeptide in the methods of the invention. The DNA sequence was encoded in a pEAG1787 expression vector. FIG. 1B shows the predicted amino acid sequence of mature huCBE11 heavy chain.

FIG. 2 shows the amino acid sequence of the Fc region of the huCBE11 heavy chain used as a starting polypeptide in the methods of the invention. Amino acid positions are indicated by EU numbering as in Kabat.

FIG. 3A shows the DNA sequence of the huCBE11 light chain. The DNA sequence was encoded in a pEAG1754 expression vector. FIG. 3B shows the predicted amino acid sequence of huCBE11 light chain.

FIG. 4A shows the DNA sequence of human Beta microglobulin. The DNA sequence was encoded in a pEAG1761 expression vector. FIG. 4B shows the predicted amino acid sequence of human Beta microglobulin.

FIG. 5A shows the nucleotide sequence of cDNA encoding a human FcRn/Fc/fusion protein. The DNA sequence was encoded in a pEAG 1761 expression vector.

FIG. 5B shows the predicted amino acid sequence of the FcRn/Fc/fusion protein.

FIG. 9 Panel A shows the location of the FcRn binding loop that extend from aspartate 280 to threonine 299 is shown in FIG. 9 with relations to FcRn domains. Panel B shows the location of residues in 15 angstrom FcRn contact zone (e.g. 243 F; 244 P; 245 P; 246 K; 247 P; 248 K; 249 D; 250 T; 251 L; 252 M; 253 I; 254 S; 255 R; 256 T; 257 P; 258 E; 259 V; 260 T; 261 C; 275 F; 276 N; 277 W; 278 Y; 279 V; 280 D; 282 V; 283 E; 284 V; 285 H; 286 N; 287 A; 288 K; 289 T; 290 K; 291 P; 292 R; 293 E; 302 V; 303 V; 304 S; 305 V; 306 L; 307 T; 308 V; 309 L; 310 H; 311 Q; 312 D; 313 W; 314 L; 315N; 316 G; 317 K; 318 E; 319 Y; 336 I; 337 S; 338 K; 339 A; 340 K; 341 G; 342 Q; 343 P; 344 R; 345 E; 346 P; 347 Q; 348 V; 367 C; 369 V; 372 F; 373 Y; 374 P; 375 S; 376 D; 377 I; 378 A; 379 V; 380 E; 381 W; 382 E; 383 S; 384 N; 385 G; 386 Q; 387 P; 388 E; 389 N; 391 Y; 393 T; 408 S; 424 S; 425 C; 426 S; 427 V; 428 M; 429 H; 430 E; 431 A; 432 L; 433 H; 434 N; 435 H; 436 Y; 437 T; 438 Q; 439 K; and 440 S) with relations to FcRn domains.

DETAILED DESCRIPTION

Figure 6:
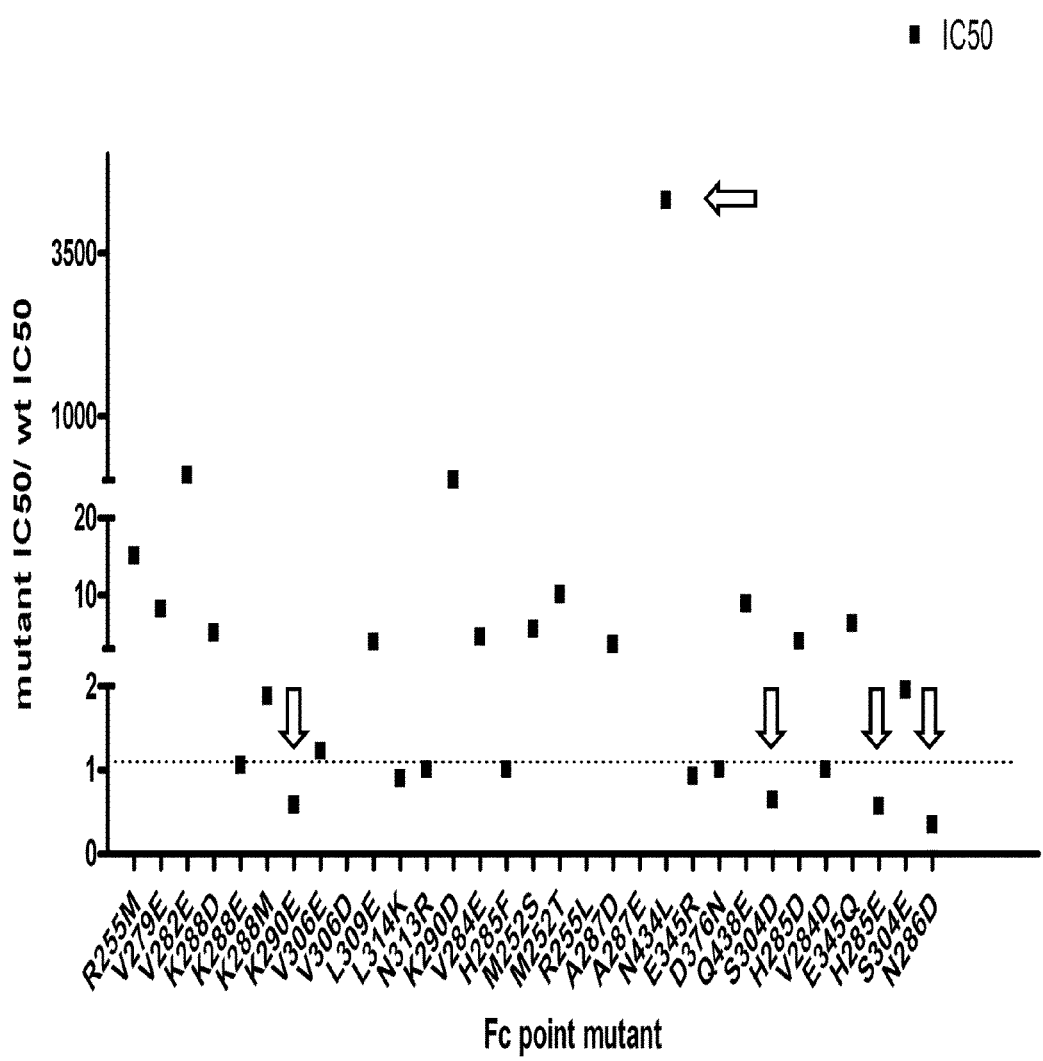
FIG. 6 shows the results obtained using a FRET-based assay for evaluation of the FcRn binding affinity of the altered polypeptides of the invention. Mutations with a measurable increase in binding affinity (H285E, N286D, K290E, and S304D) are indicated with downward pointing arrows. A mutation (N434L) with a pronounced decrease in binding affinity is indicated by a leftward pointing arrow.

The instant invention is based, at least in part, on the identification of polypeptides (such as antibodies and fusion proteins) that include at least a portion of a Fc region (e.g., a constant domain of an immunoglobulin such as IgG1) which exhibit altered binding to the neonatal Fc receptor (FcRn). Such altered polypeptides exhibit either increased or decreased binding to FcRn when compared to wild-type polypeptides and, therefore, have an increased or decreased half-life in serum, respectively. Fc region variants with improved affinity for FcRn are anticipated to have longer serum half-lives, and such molecules have useful applications in methods of treating mammals where long half-life of the administered polypeptide is desired, e.g., to treat a chronic disease or disorder. In contrast, Fc region variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc region variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered polypeptides of the invention exhibit reduced transport across the epithelium of kidney glomeruli from the vasculature. In another embodiment, the altered polypeptides of the invention exhibit reduced transport across the blood brain barrier (BBB) from the brain, into the vascular space.

The invention also pertains to methods of making such altered polypeptides and to methods of using such polypeptides. The invention also pertains to novel forms of FcRn and methods of their use.

Various aspects of the invention are described in further detail in the following subsections:

I. Definitions

The terms "protein," "polypeptide," and "peptide" are used interchangeably herein. A protein may comprise one or more of the natural amino acids or non-natural amino acids.

A "starting polypeptide" or "first polypeptide" is a polypeptide comprising an amino acid sequence which lacks one or more of the Fc region modifications disclosed herein and which differs in effector function compared to an altered or modified polypeptide. A starting polypeptide is a naturally occurring or artificially-derived polypeptide containing an Fc region, or FcRn binding portion thereof. The starting polypeptide may comprise a naturally occurring Fc region sequence or an Fc region with pre-existing amino acid sequence modifications (such as additions, deletions and/or substitutions). The starting polypeptides of the invention are modified as disclosed herein to modulate (either to increase or decrease) binding affinity to FcRn.

As used herein, the term "altered polypeptide" or "second polypeptide" refers to a polypeptide comprising a non-naturally occurring Fc binding portion which comprises at least one mutation in the Fc region. When we say that an altered polypeptide exhibits an "altered effector function", we mean that the altered polypeptide facilitates one or more (and possibly, but not necessarily, all) of its effector functions to a greater or lesser extent than the starting polypeptide.

As used herein, the term "Fc region" includes amino acid sequences derived from the constant region of an antibody heavy chain. The Fc region is the portion of a heavy chain constant region of an antibody beginning N-terminal of the hinge region at the papain cleavage site, at about position 216 according to the EU index and including the hinge, CH2, and CH3 domains.

The starting polypeptide can comprise at least a portion of an Fc region that mediates binding to FcRn. For example, in one embodiment, a starting polypeptide is an antibody or an Fc fusion protein. As used herein, the term "fusion protein" refers to a chimeric polypeptide which comprises a first amino acid sequence linked to a second amino acid sequence with which it is not naturally linked in nature. For example, a fusion protein may comprise an amino acid sequence encoding least a portion of an Fc region (e.g., the portion of the Fc region that confers binding to FcRn) and an amino acid sequence encoding a non-immunoglobulin polypeptide, e.g., a ligand binding domain of a receptor or a receptor binding domain of a ligand. The amino acid sequences may normally exist in separate proteins that are brought together in the fusion polypeptide or they may normally exist in the same protein but are placed in a new arrangement in the fusion polypeptide. A fusion protein may be created, for example, by chemical synthesis, or by creating and translating a polynucleotide in which the peptide regions are encoded in the desired relationship.

As used herein, the terms "linked," "fused" or "fusion" are used interchangeably. These terms refer to the joining together of two more elements or components, by whatever means including chemical conjugation or recombinant means. An "in-frame fusion" or "operably linked" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, an in-frame linker sequence.

In one embodiment, a polypeptide of the invention comprises an immunoglobulin antigen binding site or the portion of a receptor molecule responsible for ligand binding or the portion of a ligand molecule that is responsible for receptor binding.

As used herein, the term "effector function" refers to the functional ability of the Fc region or portion thereof to bind proteins and/or cells of the immune system and mediate various biological effects. Effector functions may be antigen-dependent or antigen-independent.

As used herein, the term "antigen-dependent effector function" refers to an effector function which is normally induced following the binding of an antibody to a corresponding antigen. Typical antigen-dependent effector functions include the ability to bind a complement protein (e.g. C1q). For example, binding of the C1 component of complement to the Fc region can activate the classical complement system leading to the opsonisation and lysis of cell pathogens, a process referred to as complement-dependent cytotoxicity (CDCC). The activation of complement also stimulates the inflammatory response and may also be involved in autoimmune hypersensitivity.

Other antigen-dependent effector functions are mediated by the binding of antibodies, via their Fc region, to certain Fc receptors ("FcRs") on cells. There are a number of Fc receptors which are specific for different classes of antibody, including IgG (gamma receptors, or IgγRs), IgE (epsilon receptors, or Ig∈Rs), IgA (alpha receptors, or IgαRs) and IgM (mu receptors, or IgμRs). Binding of antibody to Fc receptors on cell surfaces triggers a number of important and diverse biological responses including endocytosis of immune complexes, engulfment and destruction of antibody-coated particles or microorganisms (also called antibody-dependent phagocytosis, or ADCP), clearance of immune complexes, lysis of antibody-coated target cells by killer cells (called antibody-dependent cell-mediated cytotoxicity, or ADCC), release of inflammatory mediators, regulation of immune system cell activation, placental transfer and control of immunoglobulin production.

Certain Fc receptors, the Fc gamma receptors (FcγRs), play a critical role in either abrogating or enhancing immune recruitment. FcγRs are expressed on leukocytes and are composed of three distinct classes: FcγRI, FcγRII, and FcγRIII. the Fc region of the IgG immunoglobulin isotype (Gessner et al., Ann. Hematol., (1998), 76: 231-48). Structurally, the FcγRs are all members of the immunoglobulin superfamily, having an IgG-binding α-chain with an extracellular portion composed of either two or three Ig-like domains. Human FcγRI (CD64) is expressed on human monocytes, exhibits high affinity binding ($Ka=10^8-10^9 M^{-1}$) to monomeric IgG1, IgG3, and IgG4. Human FcγRII (CD32) and FcγRIII (CD16) have low affinity for IgG1 and IgG3 ($Ka<10^7 M^{-1}$), and can bind only complexed or polymeric forms of these IgG isotypes. Furthermore, the FcγRII and FcγRIII classes comprise both "A" and "B" forms. FcγRIIa (CD32a) and FcγRIIIa (CD16a) are bound to the surface of macrophages, NK cells and some T cells by a transmembrane domain while FcγRIIb (CD32b) and FcγRIIIb (CD 16b) are selectively bound to cell surface of granulocytes (e.g. neutrophils) via a phosphatidyl inositol glycan (GPI) anchor. The respective murine homologs of human FcγRI, FcγRII, and FcγRIII are FcγRIIa, FcγRIIb/1, and FcγRIo.

As used herein, the term "antigen-independent effector function" refers to an effector function which may be induced by an antibody, regardless of whether it has bound its corresponding antigen. Typical antigen-dependent effector functions include cellular transport, circulating half-life and clearance rates of immunoglobulins. A structurally unique Fc receptor, the "neonatal Fc receptor" or "FcRn", also known as the salvage receptor, plays a critical role in regulating these functions. Preferably an FcRn to which a polypeptide of the invention binds is a human FcRn.

Unlike FcγRs which belong to the Immunoglobulin superfamily, human FcRns structurally resemble polypeptides of Major Histoincompatibility, Complex (MHC) Class I (Ghetie and Ward, Immunology Today, (1997), 18(12): 592-8). FcRn is typically expressed as a heterodimer consisting of a transmembrane a or heavy chain in complex with a soluble β or light chain (β2 microglobulin). FcRn shares 22-29% sequence identity with Class I MHC molecules has a non-functional version of the MHC peptide binding groove (Simister and Mostov, Nature, (1989), 337: 184-7. Like MHC, the a chain of FcRn consists of three extracellular domains (α1, α2, α3) and a short cytoplasmic tail anchors the protein to the cell surface. The α1 and α2 domains interact with FcR binding sites in the Fc region of antibodies (Raghavan et al., Immunity, (1994), 1: 303-15).

FcRn is expressed in the maternal placenta or yolk sac of mammals and it is involved in transfer of IgGs from mother to fetus. FcRn is also expressed in the small intestine of rodent neonates, where it is involved in the transfer across the brush border epithelia of maternal IgG from ingested colostrum or milk FcRn is also expressed in numerous other tissues across numerous species, as well as in various endothelial cell lines. It is also expressed in human adult vascular endothelium, muscle vasculature, and hepatic sinusoids. FcRn is thought to play an additional role in maintaining the circulatory half-life or serum levels of IgG by binding it and recycling it to the serum. The binding of FcRn to IgG molecules is strictly pH-dependent with an optimum binding at a pH of less than 7.0.

As used herein, the term "half-life" refers to a biological half-life of a particular Fc-containing polypeptide in vivo. Half-life may be represented by the time required for half the quantity administered to a subject to be cleared from the circulation and/or other tissues in the animal. When a clearance curve of a given Fc-containing polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the Fc polypeptide in the intravascular space. Therefore, in a preferred embodiment, the term half-life as used herein refers to the half-life of the Fc polypeptide in the β-phase. The typical β phase half-life of a human antibody is 21 days.

As used herein, the term "mutation" includes substitutions, additions, or deletions of amino acids made in a starting polypeptide to obtain an altered polypeptide.

An "amino acid substitution" refers to the replacement of at least one existing amino acid residue in a predetermined amino acid sequence (an amino acid sequence of a starting polypeptide) with another different "replacement" amino acid residue. The replacement residue or residues may be "naturally occurring amino acid residues" (i.e. encoded by the genetic code) and selected from the group consisting of: alanine (A); arginine (R); asparagine (N); aspartic acid (D); cysteine (C); glutamine (Q); glutamic acid (E); glycine (G); histidine (H); Isoleucine (I): leucine (L); lysine (K); methionine (M); phenylalanine (F); proline (P): serine (S); threonine (T); tryptophan (W); tyrosine (Y); and valine (V). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of, e.g., Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

As used herein, the term "non-polar" includes amino acids that have uncharged side chains (e.g. A, L, I, V, G, P). These amino acids are usually implicated in hydrophobic interactions As used herein, the term "polar" includes amino acids that have net zero charge, but have non-zero partial charges in different portions of their side chains (e.g. M, F, W, S, Y, N, Q, C). These amino acids can participate in hydrophobic interactions and electrostatic interactions.

As used herein, the term "charged" amino acids that can have non-zero net charge on their side chains (e.g. R, K, H, E, D). These amino acids can participate in hydrophobic interactions and electrostatic interactions.

An "amino acid insertion" refers to the incorporation of at least one amino acid into a predetermined amino acid sequence. While the insertion will usually consist of the insertion of one or two amino acid residues, the present larger "peptide insertions", can be made, e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

As used herein the term "sufficient steric bulk" includes those amino acids having side chains which occupy larger 3 dimensional space. Exemplary amino acid having side chain chemistry of sufficient steric bulk include tyrosine, tryptophan, arginine, lysine, histidine, glutamic acid, glutamine, and methionine, or analogs or mimetics thereof.

As used herein the term "solvent accessible surface area" means the surface area of atoms in contact with solvent molecules. Solvent accessible surface area can be calculated using methods well known in the art. Briefly, an atom or group of atoms is defined as accessible if a solvent (water) molecule of specified size can be brought into van der Waals' contact. van der Waals' contact is the locus of the center of a solvent molecule as it rolls along the protein making the maximum permitted contact.

The term "binding affinity", as used herein, includes the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction.

The term "binding free energy" or "free energy of binding", as used herein, includes its art-recognized meaning, and, in particular, as applied to Fc-Fc receptor interactions in a solvent. Reductions in binding free energy enhance affinities, whereas increases in binding free energy reduce affinities.

The term "binding domain" or "binding site" as used herein refers to the one or more regions of the polypeptide that mediate specific binding with a target molecule (e.g. an antigen, ligand, receptor, substrate or inhibitor). Exemplary binding domains include an antibody variable domain, a receptor binding domain of a ligand, a ligand binding domain of a receptor or an enzymatic domain. The term "ligand binding domain" as used herein refers to any native receptor (e.g., cell surface receptor) or any region or derivative thereof retaining at least a qualitative ligand binding ability, and preferably the biological activity of a corresponding native receptor. The term "receptor binding domain" as used herein refers to any native ligand or any region or derivative thereof retaining at least a qualitative receptor binding ability, and preferably the biological activity of a corresponding native ligand. In one embodiment, the polypeptides have at least one binding domain specific for a molecule targeted for reduction or elimination, e.g., a cell surface antigen or a soluble antigen. In preferred embodiments, the binding domain is an antigen binding site.

In a preferred embodiment, the polypeptides of the invention comprise at least one binding site (e.g., antigen binding site, receptor binding site, or ligand binding site). In one embodiment, the polypeptides of the invention comprise at least two binding sites. In one embodiment, the polypeptides comprise three binding sites. In another embodiment, the polypeptides comprise four binding sites.

The polypeptides of the invention may be either monomers or multimers. For example, in one embodiment, the polypeptides of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

The term "exposed" amino acid residue, as used herein, includes one in which at least part of its surface is exposed, to some extent, to solvent when present in a polypeptide in solution. Preferably, the exposed amino acid residue is one in which at least about one third of its side chain surface area is exposed to solvent. Various methods are available for determining whether a residue is exposed or not, including an analysis of a molecular model or structure of the polypeptide.

The terms "variant", "altered polypeptide," "modified polypeptide", "polypeptide containing a modified amino acid" and the like, as used herein, include polypeptides which have an amino acid sequence which differs from the amino acid sequence of a starting polypeptide. Typically such polypeptides have one or more mutations, e.g., one or more amino acid residues which have been substituted with another amino acid residue or which has one or more amino acid residue insertions or deletions. Preferably, the polypeptide comprises an amino acid sequence comprising at least a portion of an Fc region which is not naturally occurring. Such variants necessarily have less than 100% sequence identity or similarity with the starting antibody. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100%, and most preferably from about 95% to less than 100%. In one embodiment, there is one amino acid difference between a starting antibody and a modified antibody of the invention. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity. The modified polypeptides of the present invention may either be expressed, or alternatively, may be modeled in silico.

The phrase "candidate amino acid residue position", as used herein, includes an amino acid position(s) identified within a polypeptide of the present invention, wherein the substitution of the candidate amino acid is modeled, predicted, or empirically found to modulate FcRn binding affinity of the polypeptide upon alteration, deletion, insertion, or substitution with another amino acid.

The term "elected amino acid", as used herein, refers to an amino acid residue(s) that has been selected by the methods of the present invention for incorporation as a replacement amino acid at a candidate amino acid position within a polypeptide. In one embodiment, substitution of a candidate amino acid residue position with an elected amino acid residue either reduces or increases the electrostatic contribution to binding free energy of the Fc-FcRn complex.

The term "antibody" as used herein includes a naturally occurring antibody obtained from, or produced by, animals that generate antibodies. For example, the antibody can be an antibody produced by, or obtained from, a rodent such as a mouse, rat, gerbil, hamster or guinea pig; from a larger animal such as a rabbit, cat or dog; from an animal commonly kept as livestock (e.g., a pig, a cow, a horse, a sheep, or a goat); or from a primate (including human and non-human primates).

The term "antibody" also includes immunoglobulin molecules and modified immunoglobulin molecules, e.g., molecules that contain an antigen binding site which binds (immunoreacts with) an antigen and at least a portion of the Fc region that mediates binding to FcRn. As used herein, the term "antibody" also includes modified or synthetic antibody molecules which comprise at least a portion of a Fc region.

As used herein, the term "hinge region" includes the portion of a heavy chain molecule that joins the CH1 domain to the CH2 domain, e.g. from about position 216-230 according to the EU number system. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

As used herein, the term "CH2 domain" includes the portion of a heavy chain molecule that extends, e.g., from about EU positions 231-340. The CH2 domain is unique in that it is not closely paired with another domain. Rather, two N-linked branched carbohydrate chains are interposed between the two CH2 domains of an intact native IgG molecule.

As used herein, the term "CH3 domain" includes the portion of a heavy chain molecule that extends approximately 110 residues from N-terminus of the CH2 domain, e.g., from about residue 341-446, EU numbering system). The CH3 domain typically forms the C-terminal portion of the antibody. In some immunoglobulins, however, additional domains may extend from CH3 domain to form the C-terminal portion of the molecule (e.g. the CH4 domain in the chain of IgM and the E chain of IgE).

In one embodiment, one or more mutations are made in an "FcRn binding loop" of an Fc region. The FcRn binding loop is comprised of amino acid residues 280, 281, 282, 283, 284, 285, 286, 287, 288, 289, 290, 291, 292, 293, 294, 295, 296, 297, 298 and 299 (according to EU numbering). This loop is illustrated in FIG. 9.

In another embodiment, one or more mutations are made in a 15 Å FcRn "contact zone." As used herein, the term 15 Å FcRn "contact zone" includes residues at the following positions (exemplary amino acids for those positions are also listed) 243 F; 244 P; 245 P; 246 K; 247 P; 248 K; 249 D; 250 T; 251 L; 252 M; 253 I; 254 S; 255 R; 256 T; 257 P; 258 E; 259 V; 260 T; 261 C; 275 F; 276 N; 277 W; 278 Y; 279 V; 280 D; 282 V; 283 E; 284 V; 285 H; 286 N; 287 A; 288 K; 289 T; 290 K; 291 P; 292 R; 293 E; 302 V; 303 V; 304 S; 305 V; 306 L; 307 T; 308 V; 309 L; 310 H; 311 Q; 312 D; 313 W; 314 L; 315 N; 316 G; 317 K; 318 E; 319 Y; 336 I; 337 S; 338 K; 339 A; 340 K; 341 G; 342 Q; 343 P; 344 R; 345 E; 346 P; 347 Q; 348 V; 367 C; 369 V; 372 F; 373 Y; 374 P; 375 S; 376 D; 377 I; 378 A; 379 V; 380 E; 381 W; 382 E; 383 S; 384 N; 385 G; 386 Q; 387 P; 388 E; 389 N; 391 Y; 393 T; 408 S; 424 S; 425 C; 426 S; 427 V; 428 M; 429 H; 430 E; 431 A; 432 L; 433 H; 434 N; 435 H; 436 Y; 437 T; 438 Q; 439 K; and 440 S (EU numbering).

"Computational analysis" as referred to herein, refers to a computer implemented process which performs all or some the operations described herein. Such a process will include an output device that displays information to a user (e.g., a CRT display, an LCD, a printer, a communication device such as a modem, audio output, and the like). The computer-implemented process is not limited to a particular computer platform, particular processor, or particular high-level programming language.

The term "structure", or "structural data", as used herein, includes the known, predicted and/or modeled position(s) in three-dimensional space that are occupied by the atoms, molecules, compounds, amino acid residues and portions thereof, and macromolecules and portions thereof, of the invention, and, in particular, a polypeptide bound to an antigen in a solvent. A number of methods for identifying and/or predicting structure at the molecular/atomic level can be used such as X-ray crystallography, NMR structural modeling, and the like.

The phrase "spatial representation of an optimal charge distribution", as used herein, includes modeling the charge distribution for an Fc region or Fc-FcRn complex, wherein the electrostatic contribution to free energy of the polypeptide when bound to FcRn is optimized (minimized), as compared to the known and/or modeled representation of charge distribution of the starting polypeptide and/or starting polypeptide when bound to FcRn. The modeling of optimal charge distribution can be arrived at by an in silico process that incorporates the known and/or modeled structure(s) of an Fc region or Fc-FcRn complex as an input. Response continuum modeling (e.g., the linearized Poisson-Boltzmann equation) can be employed to express the electrostatic binding free energy of the complex in a solvent as a sum of Fc desolvation, Fc-FcRn interaction, and FcRn desolvation terms. This in silico process is characterized by the ability to incorporate monopole, dipolar, and quadrupolar terms in representing charge distributions within the modeled charge distributions of the invention, and allows for extensive assessment of solvation/desolvation energies for amino acid residues of a polypeptide during transition of the Fc region or portion thereof between unbound and bound states. The process of modeling the spatial representation of an optimal charge distribution for a polypeptide-FcRn complex may additionally incorporate modeling of van der Waals forces, solvent accessible surface area forces, etc.

The term "solvent", as used herein, includes its broadest art-recognized meaning, referring to any liquid in which a polypeptide of the instant invention is dissolved and/or resides. Preferably, the solvent is a biologically compatable solvent. Preferred solvents include PBS, serum, and the like.

Preferred starting polypeptides comprise an amino acid sequence derived from a human antibody. A polypeptide or amino acid sequence "derived from" a designated polypeptide or source species refers to the origin of the polypeptide. Preferably, the polypeptide or amino acid sequence which is derived from a particular starting polypeptide or amino acid sequence has an amino acid sequence that is essentially identical to that of the starting sequence, or a portion thereof wherein the portion consists of at least 10-20 amino acids, preferably at least 20-30 amino acids, more preferably at least 30-50 amino acids, or which is otherwise identifiable to one of ordinary skill in the art as having its origin in the starting sequence. For example, polypeptides derived from human polypeptides may comprise one or more amino acids from another mammalian species. For example, a primate heavy chain portion, hinge portion, or binding site may be included in the subject polypeptides. Alternatively, one or more murine amino acids may be present in a starting polypeptide, e.g., in an antigen binding site (CDR) of an antibody. Preferred starting polypeptides of the invention are not immunogenic.

The term "PEGylation moiety", "polyethylene glycol moiety", or "PEG moiety" includes a polyalkylene glycol compound or a derivative thereof, with or without coupling agents or derviatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin derivatives.

The term "functional moiety" includes moieties which, preferably, add a desirable function to the variant polypeptide. Preferably, the function is added without significantly altering an intrinsic desirable activity of the polypeptide, e.g., in the case of an antibody, the antigen-binding activity of the molecule. A variant polypeptide of the invention may comprise one or more functional moieties, which may be the same or different. Examples of useful functional moieties include, but are not limited to, a PEGylation moiety, a blocking moiety, detectable moiety, a diagnostic moiety, and a therapeutic moiety. Exemplary detectable moieties include fluorescent moieties, radioisotopic moieties, radiopaque moieties, and the like. Exemplary diagnostic moieties include moieties suitable for revealing the presence of an indicator of a disease or disorder. Exemplary therapeutic moieties include, for example, anti-inflammatory agents, anti-cancer agents, anti-neurodegenerative agents, and anti-infective agents. The functional moiety may also have one or more of the above-mentioned functions. Other useful functional moieties are known in the art and described, below.

As used herein, the terms "anti-cancer agent" or "chemotherapeutic agent" includes agents which are detrimental to the growth and/or proliferation of neoplastic or tumor cells and may act to reduce, inhibit or destroy malignancy. Examples of such agents include, but are not limited to, cytostatic agents, alkylating agents, antibiotics, cytotoxic nucleosides, tubulin binding agents, hormones and hormone antagonists, and the like. Any agent that acts to retard or slow the growth of immunoreactive cells or malignant cells is within the scope of the present invention.

The term "vector" or "expression vector" is used herein for the purposes of the specification and claims, to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells.

As used herein, "tumor-associated antigens" means any antigen which is generally associated with tumor cells, i.e., occurring at the same or to a greater extent as compared with normal cells. Such antigens may be relatively tumor specific and limited in their expression to the surface of malignant cells, although they may also be found on non-malignant cells. In one embodiment, the altered polypeptides of the present invention bind to a tumor-associated antigen. Accordingly, the starting polypeptides of the present invention may be derived, generated or fabricated from any one of a number of antibodies that react with tumor associated molecules.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the phrase "subject that would benefit from administration of a polypeptide" includes subjects, such as mammalian subjects, that would receive a positive therapeutic or prophylactic outcome from administration of a polypeptide of the invention. Exemplary beneficial uses of the polypeptides disclosed herein include, e.g., detection of an antigen recognized by a polypeptide (e.g., for a diagnostic procedure) or treatment with a polypeptide to reduce or eliminate the target recognized by the polypeptide. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the polypeptide can be used in unconjugated form or can be conjugated, e.g., to a drug, prodrug, tag, or an isotope.

II. Fc Containing Polypeptides for Modification

In one embodiment, a starting polypeptide of the invention comprises at least a portion of an Fc region sufficient to confer FcRn binding. The portion of the Fc region that binds to FcRn comprises from about amino acids 282-438 of IgG1, EU numbering. Amino acid positions in the Fc region are numbered herein according to the EU index numbering system (see Kabat at al., in "Sequences of Proteins of Immunological Interest", U.S. Dept. Health and Human Services, 5$^{th}$ edition, 1991). The "EU index as in Kabat" refers to the residue numbering of the human IgG1 EU antibody.

Fc regions of the invention are preferably human in origin. An amino acid sequence of an exemplary Fc region (a human IgG1 region) is shown in SEQ ID NO:1 and in SEQ ID NO: 2 (SEQ ID NO:1=CH2 domain, SEQ ID NO:2=CH3 domain). The amino acid sequence of the Fc Region is also presented below in Table 1 to illustrate the EU numbering of the amino acids.

TABLE 1

| Human IgG1 CH2 and CH3 domains. | |
|---|---|
| CH2 domain (EU Positions 231-340) | |
| 231 | APELLGG |
| 238 | PSVFLFPPKP |
| 248 | KDTLMISRTP |
| 258 | EVTCVVVDVS |
| 268 | HEDPEVKFNW |
| 278 | YVDGVEVHNA |
| 288 | KTKPREEQYN |
| 298 | STYRVVSVLT |
| 308 | VLHQDWLNGK |
| 318 | EYKCKVSNKA |
| 328 | LPAPIEKTIS |
| 338 | KAK |
| CH3 domain (EU positions 341-446) | |
| 341 | GQPREPQ |
| 348 | VYTLPPSRDE |
| 358 | LTKNQVSLTC |
| 368 | LVKGFYPSDI |

TABLE 1-continued

Human IgG1 CH2 and CH3 domains.

| | |
|---|---|
| 378 | AVEWESNGQP |
| 388 | ENNYKTTPPV |
| 398 | LDSDGSFFLY |
| 408 | SKLTVDKSRW |
| 418 | QQGNVFSCSV |
| 428 | MHEALHNHYT |
| 438 | QKSLSLSPG |

In one embodiment, a starting polypeptide of the invention comprises at least amino acids 282-340 of a CH2 domain. In another embodiment, a starting polypeptide of the invention comprises a complete CH2 domain (about amino acids 231-340 of an antibody Fc region according to EU numbering). In another embodiment, a starting polypeptide of the invention comprises at least a CH2 domain and at least one of a hinge region (about amino acids 216-230 of an antibody Fc region according to EU numbering), and a CH3 domain (about amino acids 341-446 of an antibody Fc region according to EU numbering). In one embodiment, a starting polypeptide of the invention comprises a CH2 and a CH3 domain. In another embodiment, a starting polypeptide of the invention comprises a hinge, a $CH_2$, and a $CH_3$ domain. In one embodiment, a starting polypeptide of the invention comprises the sequence shown in SEQ ID NO:2. Fc regions or FcRn binding portions thereof may be derived from heavy chains of any isotype, including IgG1, IgG2, IgG3 and IgG4. In one embodiment, the human isotype IgG1 is used.

The domains making up the Fc region of a starting polypeptide may be derived from different immunoglobulin molecules. For example, a polypeptide may comprise a CH2 domain derived from an IgG1 molecule and a hinge region derived from an IgG3 molecule. In another example, a starting polypeptide can comprise a hinge region derived, in part, from an IgG1 molecule and, in part, from an IgG3 molecule. In another example, a starting polypeptide can comprise a chimeric hinge derived, in part, from an IgG1 molecule and, in part, from an IgG4 molecule. As set forth above, it will be understood by one of ordinary skill in the art that the starting Fc domains may be modified (e.g., in a non-FcRn binding portion of the molecule) such that they vary in amino acid sequence from a naturally occurring antibody molecule.

The starting polypeptides of the invention may comprise at least one Fc region or FcRn binding portion thereof. Preferred starting polypeptides of the invention additionally comprise at least one binding domain, e.g., an antigen binding domain, receptor binding domain, or ligand binding domain. In one embodiment, the starting polypeptides comprise at least one binding domain and at least one Fc portion. In one embodiment, the starting polypeptide is comprised of two binding domains and two Fc portions.

In one embodiment, the starting polypeptides of the invention have at least one binding domain specific for a target molecule which mediates a biological effect (e.g., a ligand capable of binding to a cell surface receptor or a cell surface receptor capable of binding a ligand) and mediating transmission of a negative or positive signal to a cell together with at least one Fc portion. In one embodiment, starting polypeptides have at least one binding domain specific for an antigen targeted for reduction or elimination, e.g., a cell surface antigen or a soluble antigen, together with at least one Fc region or FcRn binding portion thereof.

A. Antibodies

In one embodiment, a starting polypeptide of the invention is an antibody. Using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

In embodiments in which the Fc containing polypeptide is an antibody, the antibody can be a monoclonal or polyclonal antibody. Methods for producing monoclonal antibodies have been known for some time (see, e.g., Kohler and Milstein, *Nature* 256:495-497, 1975), as have techniques for stably introducing immunoglobulin-encoding DNA into myeloma cells (see, e.g., Oi et al., *Proc. Natl. Acad. Sci. USA* 80:6351-6355, 1983). These techniques, which include in vitro mutagenesis and DNA transfection, allow the construction of recombinant immunoglobulins and can be used to produce the polypeptide used in the methods of the invention or those that result therefrom (e.g., therapeutic and diagnostic antibodies). Production methods, vectors, and hosts are described further below.

The starting antibodies used in the invention may be produced in a non-human mammal, e.g., murine, guinea pig, primate, rabbit or rat, by immunizing the animal with the antigen or a fragment thereof. See Harlow & Lane, supra, incorporated by reference for all purposes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature,* 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Prin-*

*ciples and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

Optionally, antibodies may be screened for binding to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

In another embodiment, DNA encoding the desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments (e.g., antigen binding sites) may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated by reference herein. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or synthetic to provide obtain polypeptides of the present invention.

Variable and constant domains can be separately cloned, e.g., using the polymerase chain reaction and primers which are selected to amplify the domain of interest. In addition, the sequences of many antibody variable and constant domains are known and such domains can be synthesized using methods well known in the art. For example, constant region domains can be selected having a particular effector function (or lacking a particular effector function) or with a particular modification to reduce immunogenicity. Alternatively, variable domains can be obtained from libraries of variable gene sequences from an animal of choice. Libraries expressing random combinations of domains, e.g., $V_H$ and $V_L$ domains, can be screened with a desired antigen to identify elements which have desired binding characteristics. Methods of such screening are well known in the art. For example, antibody gene repertoires can be cloned into a λ bacteriophage expression vector (Huse, W D et al. (1989). Science, 2476:1275). In addition, cells (Francisco et al. (1994), PNAS, 90:10444; Georgiou et al. (1997), Nat. Biotech., 15:29; Boder and Wittrup (1997) Nat. Biotechnol. 15:553; Boder et al., (2000), PNAS, 97:10701; Daugtherty, P. et al. (2000) J. Immunol. Methods. 243:211) or viruses (e.g., Hoogenboom, H R. (1998), Immunotechnology 4:1; Winter et al. (1994). Annu. Rev. Immunol. 12:433; Griffiths, AD. (1998). Curr. Opin. Biotechnol. 9:102) expressing antibodies on their surface can be screened. Those skilled in the art will also appreciate that DNA encoding antibody domains may also be derived from antibody phage libraries, e.g., using pd phage or Fd phagemid technology. Exemplary methods are set forth, for example, in EP 368 684 B1; U.S. Pat. No. 5,969,108; Hoogenboom et al., (2000) Immunol. Today 21:371; Nagy et al. (2002) Nat. Med. 8:801; Huie et al. (2001), PNAS, 98:2682; Lui et al. (2002), J. Mol. Biol. 315:1063, each of which is incorporated herein by reference. Several publications (e.g., Marks et al. (1992), Bio/Technology 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), PNAS 95:14130; Hanes and Pluckthun. (1999), Curr. Top. Microbiol. Immunol. 243:107; He and Taussig. (1997), Nuc. Acids Res., 25:5132; Hanes et al. (2000), Nat. Biotechnol. 18:1287; Wilson et al. (2001), PNAS, 98:3750; or Irving et al. (2001) J. Immunol. Methods 248:31).

Preferred libraries for screening are human variable gene libraries. $V_L$ and $V_H$ domains from a non-human source may also be used. Libraries can be naïve, from immunized subjects, or semi-synthetic (Hoogenboom and Winter. (1992). J. Mol. Biol. 227:381; Griffiths et al., (1995) EMBO J 13:3245; de Kruif et al. (1995). J. Mol. Biol. 248:97; Barbas et al. (1992), PNAS, 89:4457). In one embodiment, mutations can be made to immunoglobulin domains to create a library of nucleic acid molecules having greater heterogeneity (Thompson et al. (1996), J. Mol. Biol. 256:77; Lamminmaki et al. (1999), J. Mol. Biol. 291:589; Caldwell and Joyce. (1992), PCR Methods Appl. 2:28; Caldwell and Joyce. (1994), PCR Methods Appl. 3:S136). Standard screening procedures can be used to select high affinity variants. In another embodiment, changes to $V_H$ and $V_L$ sequences can be made to increase antibody avidity, e.g., using information obtained from crystal structures using techniques known in the art.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis. In many cases immunoreative antibodies for each of these antigens have been reported in the literature.

In another embodiment, binding of the starting polypeptide to an antigen results in the reduction or elimination of the antigen, e.g., from a tissue or from the circulation. In another embodiment, the starting polypeptide has at least one binding domain specific for an antigen that can be used to detect the presence of a target molecule (e.g., to detect a contaminant or diagnose a condition or disorder). In yet another embodiment, a starting polypeptide of the invention comprises at least one binding site that targets the molecule to a specific site in a subject (e.g., to a tumor cell or blood clot).

In one embodiment, the starting polypeptides of the present invention may be immunoreactive with one or more tumor-associated antigens. For example, for treating a cancer or neoplasia an antigen binding domain of a polypeptide preferably binds to a selected tumor associated antigen. Given the number of reported antigens associated with neoplasias, and the number of related antibodies, those skilled in the art will appreciate that a polypeptide of the invention may be derived from any one of a number of whole antibodies. More generally, starting antibodies useful in the present invention may be obtained or derived from any antibody (including those previously reported in the literature) that reacts with an antigen or marker associated with the selected condition. Further, a starting antibody, or fragment thereof, used to generate the disclosed polypeptides may be murine, human, chimeric, humanized, non-human primate or primatized. Exemplary tumor-associated antigens bound by the starting polypeptides used in the invention include for example, pan B antigens (e.g. CD20 found on the surface of both malignant and non-malignant B cells such as those in non-Hodgkin's lymphoma) and pan T cell antigens (e.g. CD2, CD3, CD5, CD6, CD7). Other exemplary tumor associated antigens comprise but are not limited to MAGE-1, MAGE-3, MUC-1, HPV 16, HPV E6 & E7, TAG-72, CEA, α-Lewis$^y$, L6-Antigen, CD19, CD22, CD25, CD30, CD33, CD37, CD44, CD52, CD56, mesothelin, PSMA, HLA-DR, EGF Receptor, VEGF Receptor, and HER2Receptor.

Previously reported antibodies that react with tumor-associated antigens may be altered as described herein to provide the altered antibodies of the present invention. Exemplary target antibodies capable of reacting with tumor-associated antigens include: 2B8, Lym 1, Lym 2, LL2, Her2, B1, BR96, MB1, BH3, B4, B72.3, 5E8, B3F6, 5E10, α-CD33, α-CanAg, α-CD56, α-CD44v6, α-Lewis, and α-CD30.

More specifically, exemplary target antibodies include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), Trastuzumab (Herceptin®, Genentech Inc., South San Francisco), Tositumomab (Bexxar®, Coulter Pharm., San Francisco), Alemtzumab (Campath®, Millennium Pharmaceuticals, Cambridge), Gemtuzurnab ozogamicin (Mylotarg®, Wyeth-Ayerst, Philadelphia), Cetuximab (Erbitux®, Imclone Systems, New York), Bevacizumab (Avastin®, Genentech Inc., South San Francisco), BR96, BL22, LMB9, LMB2, MB1, BH3, B4, B72.3 (Cytogen Corp.), SS1 (NeoPharm), CC49 (National Cancer Institute), Cantuzumab mertansine (ImmunoGen, Cambridge), MNL 2704 (Milleneum Pharmaceuticals, Cambridge), Bivatuzumab mertansine (Boehringer Ingelheim, Germany), Trastuzumab-DM1 (Genentech, South San Francisco), My9-6-DM1 (ImmunoGen, Cabridge), SGN-10, -15, -25, and -35 (Seattle Genetics, Seattle), and 5E10 (University of Iowa). In preferred embodiments, the starting antibodies of the present invention will bind to the same tumor-associated antigens as the antibodies enumerated immediately above. In particularly preferred embodiments, the polypeptides will be derived from or bind the same antigens as Y2B8, C2B8, CC49 and C5E10 and, even more preferably, will comprise domain deleted antibodies (i.e., ΔCH2 antibodies).

In a first preferred embodiment, the starting antibody will bind to the same tumor-associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine starting of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., *Blood* 83: 435-445 (1994)). Those skilled in the art will appreciate that dimeric variants (homodimers or heterodirners) of C2B8 or 2B8, synthetic according to the instant disclosure, may be conjugated with effector moieties according to the methods of the invention, in order to provide modified antibodies with even more effective in treating patients presenting with CD20+ malignancies.

In other preferred embodiments of the present invention, the starting polypeptide of the invention will be derived from, or bind to, the same tumor-associated antigen as CC49. CC49 binds human tumor-associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC 11 (ATCC No. 9455); and CC15 (ATCC No. HB 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be synthetic and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. *Cancer Biotherapy*, 8(1):95-109 (1993), Slavin-Chiorini et al. *Int. Cancer* 53:97-103 (1993) and Slavin-Chiorini et al. *Cancer. Res.* 55:5957-5967 (1995).

In one embodiment, a starting polypeptide of the invention binds to the CD23 (U.S. Pat. No. 6,011,138). In a preferred embodiment, a starting polypeptide of the invention binds to the same epitope as the 5E8 antibody. In another embodiment, a starting polypeptide of the invention comprises at least one CDR from an anti-CD23 antibody, e.g., the 5E8 antibody.

In a preferred embodiment, a starting polypeptide of the invention binds to the CRIPTO-I antigen (WO02/088170A2 or WO03/083041A2). In a more preferred embodiment, a polypeptide of the invention binds to the same epitope as the B3F6 antibody. In still another embodiment, a polypeptide of the invention comprises at least one CDR from an anti-CRIPTO-I antibody, e.g., the B3F6 antibody.

Still other embodiments of the present invention comprise modified antibodies that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, polypeptides that specifically bind to the same tumor-associated antigen recognized by C5E10 antibodies could be used alone or conjugated with an effector moiety by the methods of the invention, thereby providing a modified polypeptide that is useful for the improved treatment of neoplastic disorders. In particularly preferred embodiments, the starting polypeptide will be derived or comprise all or part of the antigen binding region of the C5E10 antibody as secreted from the hybridoma cell line having ATCC accession No. PTA-865. The resulting polypeptide could then be conjugated to a therapeutic effector moiety as described below and administered to a patient suffering from prostate cancer in accordance with the methods herein.

B. Antibody Variants

In addition to naturally-occurring antibodies, the starting antibodies of the invention may include immunoreactive fragments or portions which are not naturally occurring.

In another embodiment, a heavy chain variable portion and a light chain variable portion of an antigen binding domain of a target antibody of the invention are present in the same polypeptide, e.g., as in a single chain antibody (ScFv) or a minibody (see e.g., U.S. Pat. No. 5,837,821 or WO 94/09817A1). Minibodies are dimeric molecules made up of two polypeptide chains each comprising an ScFv molecule (a single polypeptide comprising one or more antigen binding sites, e.g., a $V_L$ domain linked by a flexible linker to a $V_H$ domain fused to a CH3 domain via a connecting peptide). ScFv molecules can be constructed in a $V_H$-linker-$V_L$ orientation or $V_L$-linker-$V_H$ orientation. The flexible hinge that links the $V_L$ and $V_H$ domains that make up the antigen binding site preferably comprises from about 10 to about 50 amino acid residues. An exemplary connecting peptide for this purpose is (Gly4Ser)3 (Huston et al. (1988). *PNAS*, 85:5879). Other connecting peptides are known in the art.

Methods of making single chain antibodies are well known in the art, e.g., Ho et al. (1989), *Gene,* 77:51; Bird et al. (1988), *Science* 242:423; Pantoliano et al. (1991), *Biochemistry* 30:10117; Milenic et al. (1991), *Cancer Research,* 51:6363; Takkinen et al. (1991), *Protein Engineering* 4:837. Minibodies can be made by constructing an ScFv component and connecting peptide-$CH_3$ component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis. In one embodiment, a minibody of the invention comprises a connecting peptide. In one embodiment, the connecting peptide comprises a Gly/Ser linker, e.g., GGGSSGGGSGG.

In another embodiment, a tetravalent minibody can be constructed. Tetravalent minibodies can be constructed in the same manner as minibodies, except that two ScFv molecules are linked using a flexible linker, e.g., having an amino acid sequence $(G4S)_4G3AS$.

In another embodiment, a starting antibody of the invention comprises a diabody. Diabodies are similar to scFv molecules, but usually have a short (less than 10 and preferably 1-5) amino acid residue linker connecting both variable domains, such that the $V_L$ and $V_H$ domains on the same polypeptide chain can not interact. Instead, the $V_L$ and $V_H$ domain of one polypeptide chain interact with the $V_H$ and $V_L$ domain (respectively) on a second polypeptide chain (WO 02/02781).

In another embodiment, a starting antibody of the invention comprises an immunoreactive fragment or portion thereof (e.g. an scFv molecule, a minibody, a tetravalent minibody, or a diabody) operably linked to an FcR binding portion. In an exemplary embodiment, the FcR binding portion is a complete Fc region.

In another embodiment, at least one antigen binding domain of a starting antibody is catalytic (Shokat and Schultz. (1990). *Annu. Rev. Immunol.* 8:335). Antigen binding domains with catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht et al., (1968), *J. Am. Chem. Soc.* 90:5833) and thereby greatly reduce the entropy of a chemical reaction. Finally, catalytic antibodies can convert the energy obtained upon substrate binding to distort the reaction towards a structure resembling the transition state.

Acid or base residues can be brought into the antigen binding site by using a complementary charged molecule as an immunogen. This technique has proved successful for elicitation of antibodies with a hapten containing a positively-charged ammonium ion (Shokat, et al., (1988), *Chem. Int. Ed. Engl.* 27:269-271). In another approach, antibodies can be elicited to stable compounds that resemble the size, shape, and charge of the transition state of a desired reaction (i.e., transition state analogs). See U.S. Pat. No. 4,792,446 and U.S. Pat. No. 4,963,355 which describe the use of transition state analogues to immunize animals and the production of catalytic antibodies. Both of these patents are hereby incorporated by reference. Such molecules can be administered as part of an immunoconjugate, e.g., with an immunogenic carrier molecule, such as KLH.

In one embodiment, a starting antibody of the invention is bispecific. Bispecific molecules can bind to two different target sites, e.g., on the same target molecule or on different target molecules. For example, in the case of antibodies, bispecific molecules can bind to two different epitopes, e.g., on the same antigen or on two different antigens. Bispecific molecules can be used, e.g., in diagnostic and therapeutic applications. For example, they can be used to immobilize enzymes for use in immunoassays. They can also be used in diagnosis and treatment of cancer, e.g., by binding both to a tumor associated molecule and a detectable marker (e.g., a chelator which tightly binds a radionuclide. Bispecific molecules can also be used for human therapy, e.g., by directing cytotoxicity to a specific target (for example by binding to a pathogen or tumor cell and to a cytotoxic trigger molecule, such as the T cell receptor. Bispecific antibodies can also be used, e.g., as fibrinolytic agents or vaccine adjuvants.

Examples of bispecific binding molecules include those with at least two arms directed against tumor cell antigens; bispecific binding molecules with at least one arm directed against a tumor cell antigen and the at least one arm directed against a cytotoxic trigger molecule (such as anti-CD3/anti-malignant B-cell (1D10), anti-CD3/anti-p185.sup.HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3); bispecific binding molecules with at least one which binds specifically to a tumor antigen and at least one which binds to a toxin (such as anti-saporin/anti-Id-1, anti-CD22/anti-saporin, anti-CD7/anti-saporin, anti-CD38/anti-saporin, anti-CEA/anti-ricin A chain, anti-interferon-.alpha.(IFN-.alpha.)/anti-hybridoma idiotype, anti-CEA/anti-vinca alkaloid); bispecific binding molecules for converting enzyme activated prodrugs (such as anti- CD30/anti-alkaline phosphatase (which catalyzes conversion of mitomycin phosphate prodrug to mitomycin alcohol)); bispecific binding molecules which can be used as fibrinolytic agents (such as anti-fibrin/anti-tissue plasminogen activator (tPA), anti-fibrin/anti-urokinase-type plasminogen activator (uPA)); bispecific binding molecules for targeting immune complexes to cell surface receptors (such as anti-low density lipoprotein (LDL); bispecific binding molecules for use in therapy of infectious diseases (such as anti-CD3/anti-herpes simplex virus (HSV), anti-T-cell receptor:CD3 complex/anti-influenza, anti-Fc.gamma.R/anti-HIV; bispecific binding molecules for tumor detection in vitro or in vivo such as anti-CEA/anti-EOTUBE, anti-CEA/anti-DPTA, anti-p185HER2/anti-1-hapten); bispecific binding molecules as vaccine adjuvants (see Fanger et al., supra); and bispecific binding molecules as diagnostic tools (such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase (see Nolan et al., supra)). Examples of trispecific antibodies include anti-CD3/anti-CD4/anti-CD37, anti-CD3/anti-CD5/anti-CD37 and anti-CD3/anti-CD8/anti-CD37.

In a preferred embodiment, a bispecific molecule of the invention binds to CRIPTO-I.

Bispecific molecules may be monovalent for each specificity or be multivalent for each specificity. For example, an antibody molecule or fusion protein may comprise one binding site that reacts with a first target molecule and one binding site that reacts with a second target molecule or it may comprise two binding sites that react with a first target molecule and two binding sites that react with a second target molecule. Methods of producing bispecific molecules are well known in the art. For example, recombinant technology can be used to produce bispecific molecules. Exemplary techniques for producing bispecific molecules are known in the art (e.g., Kontermann et al. Methods in Molecular Biology Vol. 248: Antibody Engineering: Methods and Protocols. Pp 227-242 US 2003/0207346 A1 and the references cited therein). In one embodiment, a multimeric bispecific molecules are prepared using methods such as those described e.g., in US 2003/0207346 A1 or U.S. Pat. No. 5,821,333, or US2004/0058400.

As used herein the phrase "multispecific fusion protein" designates fusion proteins (as hereinabove defined) having at least two binding specificities (i.e. combining two or more binding domains of a ligand or receptor). Multispecific fusion proteins can be assembled as heterodimers, heterotrimers or heterotetramers, essentially as disclosed in WO 89/02922 (published Apr. 6, 1989), in EP 314, 317 (published May 3, 1989), and in U.S. Pat. No. 5,116,964 issued May 2, 1992. Preferred multispecific fusion proteins are bispecific. Examples of bispecific fusion proteins include CD4-IgG/TNFreceptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

Target binding sites for the multispecific binding molecules of the invention can readily be selected by one of ordinary skill in the art. While not limiting in any way, exemplary binding sites include one or more epitopes of a tumor antigen. Other exemplary target molecules include one or more epitopes of, e.g., heparin sulfate, growth factors or their receptors (e.g., epidermal growth factor receptor, insulin-like growth factor receptor, hepatocyte growth factor (HGF/SF) receptor (See, e.g., Cao et al. Proc. Natl. Acad. Sci. 2001. 98:7443; Lu et al. 2004. J. Biol. Chem. 279:2856).

In another embodiment, an antigen binding domain of a starting antibody consists of a $V_H$ domain, e.g., derived from camelids, which is stable in the absence of a $V_L$ chain (Hamers-Casterman et al. (1993). Nature, 363:446; Desmyter et al. (1996). Nat. Struct. Biol. 3: 803; Decanniere et al. (1999). Structure, 7:361; Davies et al. (1996). Protein Eng., 9:531; Kortt et al. (1995). J. Protein Chem., 14:167).

Non-human starting antibodies, or fragments or domains thereof, can be altered to reduce their immunogenicity using art recognized techniques. Humanized starting polypeptides are starting polypeptides derived from a non-human protein, that retains or substantially retains the properties of the starting antibody, but which is less immunogenic in humans. In the case of humanized starting antibodies, this may be achieved by various methods, including (a) grafting the entire non-human variable domains onto human constant regions to generate chimeric target antibodies; (b) grafting at least a part of one or more of the non-human complementarity determining regions (CDRs) into a human framework and constant regions with or without retention of critical framework residues; (c) transplanting the entire non-human variable domains, but "cloaking" them with a human-like section by replacement of surface residues. Such methods are disclosed in Morrison et al., (1984), PNAS. 81: 6851-5; Morrison et al., (1988), Adv. Immunol. 44: 65-92; Verhoeyen et al., (1988), Science 239: 1534-1536; Padlan, (1991), Molec. Immun. 28: 489-498; Padlan, (1994), Molec. Immun. 31: 169-217; and U.S. Pat. Nos. 5,585,089, 5,693,761 and 5,693,762 all of which are hereby incorporated by reference in their entirety.

De-immunization can also be used to decrease the immunogenicity of a starting antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence Individual T cell epitopes from the T cell epitope map are analyzed in order to identify alternative amino acid substitutions with a low risk of altering activity of the antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

In one embodiment, the starting polypeptide comprises a chimeric antibody. In the context of the present application the term "chimeric antibodies" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse) and the constant region is human. Preferably, the variable domains in both the heavy and light chains of a target antibody are altered by at least partial replacement of one or more CDRs and, if necessary, by partial framework region replacement and sequence changing. Although the CDRs may be derived from an antibody of the same class or even subclass as the target antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

In preferred embodiments, a starting polypeptide of the invention will not elicit a deleterious immune response in a human. Those skilled in the art will appreciate that chimeric starting polypeptides can also be produced. In the context of the present application the term "chimeric starting antibody" will be held to mean any starting antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse) and the constant region is human. While the immunogenic specificity of the variable region is not generally affected by its source, a human constant region is less likely to elicit an immune response from a human subject than would the constant region from a non-human source.

C. Fusion Proteins

The starting polypeptides of the invention can also be a fusion protein which comprise at least an FcRn binding portion of an Fc region. Preferably, the fusion proteins of the invention comprise a binding domain (which comprises at least one binding site). The subject fusion proteins may be bispecific (with one binding site for a first target and a second binding site for a second target) or may be multivalent (with two binding sites for the same target).

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349: 164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

Ordinarily, the binding domain is fused C-terminally to the N-terminus of the Fc portion and in place of a cell anchoring region. For example, any transmembrane regions or lipid or phospholipids anchor recognition sequences of ligand binding receptor are preferably inactivated or deleted prior to fusion. DNA encoding the ligand or ligand binding partner is cleaved by a restriction enzyme at or proximal to the 5' and 3' ends of the DNA encoding the desired ORF segment. The resultant DNA fragment is then readily inserted into DNA encoding a heavy chain constant region. The precise site at which the fusion is made may be selected empirically to optimize the secretion or binding characteristics of the soluble fusion protein. DNA encoding the fusion protein is then transfected into a host cell for expression.

In one embodiment, a fusion protein combines the binding domain(s) of the ligand or receptor (e.g. the extracellular domain (ECD) of a receptor) with at least one Fc portion and, optionally, a synthetic connecting peptide. In one embodiment, when preparing the fusion proteins of the present invention, nucleic acid encoding the binding domain of the ligand or receptor domain will be fused C-terminally to nucleic acid encoding the N-terminus of an Fc region. N-terminal fusions are also possible. Fusions may also be made to the C-terminus of the Fc portion of a constant domain, or immediately N-terminal to the CH1 of the heavy chain or the corresponding region of the light chain.

In one embodiment, the Fc region of the fusion protein includes substantially the entire Fc region of an antibody, beginning in the hinge region just upstream of the papain cleavage site which defines IgG Fc chemically (about residue 216 EU numbering, taking the first residue of heavy chain constant region to be 114) and ending at its C-terminus. The precise site at which the fusion is made is not critical; particular sites are well known and may be selected in order to optimize the biological activity, secretion, or binding characteristics of the molecule. Methods for making fusion proteins are known in the art.

For bispecific fusion proteins, the fusion proteins may be assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Additional exemplary ligands and their receptors that may be included in the subject fusion proteins include the following:

i) Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

ii) Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a fusion protein of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

iii) Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

iv) Growth Factors and Growth Factor Receptors

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stem-cell factor (SCF), thrombopoietin (c-Mpl ligand), and the Wnt polypeptides (U.S. Pat. No. 6,159,462).

Exemplary growth factor receptors which may be used as targeting receptor domains of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as $p75^{NTR}$ or p75, which binds NGF, BNDF, and NT-3, and high affinity receptors that are members of the trk family of the receptor tyrosine kinases (e.g. trkA, trkB (EP 455,460), trkC (EP 522,530)).

v) Hormones

Exemplary growth hormones for use as targeting agents in the fusion proteins of the invention include rennin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, lutenizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

vi) Clotting Factors

Exemplary blood coagulation factors for use as targeting agents in the fusion proteins of the invention include the clotting factors (e.g., factors V, VII, VIII, X, IX, XI, XII and XIII, von Willebrand factor); tissue factor (U.S. Pat. Nos. 5,346,991, 5,349,991, 5,726,147); thrombin and prothrombin; fibrin and fibrinogen; plasmin and plasminogen; plasminogen activators, such as urokinase or human urine or tissue-type plasminogen activator (t-PA).

Other exemplary fusion proteins are taught, e.g., in WO0069913A1 and WO0040615A2. Another exemplary molecule that may be included in a fusion protein of the invention is IGSF9. Fusion proteins can be prepared using methods that are well known in the art (see for example U.S. Pat. Nos. 5,116,964 and 5,225,538).

III. Methods of Identifying Candidate Amino Acids for Modification

The present invention provides methods for identifying particular amino acid residues in the Fc region (or FcRn binding portion thereof) of a starting Fc-containing polypeptide, that when altered by a mutation (e.g, by amino acid substitution), are predicted to result in the modulation of binding affinity to FcRn and modulation of the half-life of the polypeptide in serum.

The methods include molecular or computational modeling, which can be used to predict amino acid alterations in the Fc region to modulate (e.g., enhance or reduce) binding to an FcRn. Generally, the methods begin with a "first" or "starting" polypeptide, or a complex (e.g. crystal structure or homology model) containing it, and result in a "second" or "altered" or "modified" polypeptide, which differs from the first polypeptide in that binding affinity to FcRn is modulated and the modified polypeptide performs better in a particular therapeutic or diagnostic application. The modeling can be carried out in silico.

The methods may comprise one or more steps. For example, the method may comprise providing a structure of a complex, or data corresponding thereto, between the target Fc polypeptide and an FcRn. In another or subsequent step, the methods may comprise identifying a defined residue or set of residues (ie. candidate amino acids) within the Fc region of a starting polypeptide that can be modified (e.g., mutated) and are predicted to affect the binding affinity of the polypeptide for FcRn.

Preferred mutations that are introduced in the Fc region of a starting polypeptide include those mutations that alter an antigen-independent effector function (e.g. half-life) of the starting polypeptide. In one embodiment, the mutation does not compromise any other existing effector functions of the starting polypeptide (e.g, antigen, ligand, or receptor binding or an Fc mediated effector function (other than FcRn binding) or diminish from its intended use. Introduced mutations, therefore, preferably maintain many of the other advantages that the Fc region provides. For example, Fc-containing polypeptides often have ADCC functionality. This important cell killing activity would be partially or wholly lost in antibody constructs having truncated Fc regions. Maintaining Fc-dependent ADCC functionality can be important in certain applications because it can elicit a cell killing affect serving to enhance the efficacy of the anti-cancer drug or other drug that works by a ADCC dependent depletion mechanism.

In preferred embodiments, the altered polypeptides of the invention contain mutations that do not abolish, or more preferably, do not modulate, other desirable immune effector or receptor binding functions of the starting polypeptide. In particularly preferred embodiments, the altered polypeptides contain mutations that do not alter binding of the altered polypeptide to an Fc-binding protein that is capable of facilitating purification of the altered polypeptide, in particular Staphylococcal Protein A or G. The site on Fc responsible for binding to Protein A is known in the art (Deisenhofer J. 1981 Biochemistry. April 28; 20(9):2361-70)

A. Sequence Based Analysis

In one embodiment, potential alternation sites are predicted based on a sequence comparison with the Fc region of the starting polypeptide and a mammalian Fc region with a dissimilar binding affinity for FcRn. The sequences of the Fc regions are aligned and one or more corresponding amino acids from the sequence with dissimilar binding is substituted into the Fc region of the starting polypeptide.

In one embodiment, where shorter half life is desired, a corresponding amino acid is chosen from an immunoglobulin of an unrelated mammalian species, wherein the immunoglobulin displays a lower affinity for the FcRn receptor. In an alternative embodiment, where longer half life is desired, a homologous amino acid is chosen from an immunoglobulin of an unrelated mammalian species, wherein the immunoglobulin displays a higher affinity for the FcRn receptor.

For example, the rabbit Fc region shows a high level of homology to the human Fc region, particularly within the regions that contact hFcRn. In addition, rabbit IgG binds hFcRn more tightly than does the human IgG (Ober et al., *Int. Immunol.* 13:1551-1559, 2001). Therefore, in one exemplary embodiment, potential alteration sites are identified as those residues in the Fc region of the polypeptide to be modified (e.g., in the human Fc region) which differ from the polypeptide with the desired biological properties (e.g. the rabbit Fc region) and one or more of the amino acid residues of a human IgG1 Fc region are replaced by one or more of the corresponding amino acid residues from the rabbit IgG1 Fc region.

For example, the chimeric proteins will represent specific amino acids or a combination of amino acids in the human Fc that have been substituted by rabbit Fc amino acids. The rabbit Fc amino acids are defined from contact areas between the human Fc and neonatal Fc receptor (hFcRn) shown in a homology model of developed from the ratIgG2a ratFcRn crystal structure. Specific amino acids defined to be within the contact domains of human Fc:human FcRn can then be changed from the human sequence to the rabbit sequence. Alternatively, one or more of the residues within a human Fc can be replaced with the corresponding amino acid residue(s) from a guinea pig immunoglobulin of the same class.

Exemplary alteration sites include EU positions 280, 281, 282, 283, 284, 285, 288, 289, 290, 305, 307, 308, 309, 315, 340, 344, and 378.

More specifically, a polypeptide of the invention may contain at least one amino acid mutations selected from the group consisting of Asp280Asn (where D indicates amino acid position to be mutated (by substitution) at the recited EU position (278) and where N indicates the amino acid to be substituted into that position to arrive at the altered polypeptide), Gly281Glu, Val282Glu, Glu283Gln, His285Arg, Asn286Thr, Lys288Arg, Thr289Pro, Lys290Pro, Val305Thr, Thr307Pro, Val308Ile, Leu309Thr, Asn315Arg, Lys340Arg, Arg344Leu, Ala378Ser, Ser383Lys, Glu386Lys, Pro387Ala, and Asn389Asp, according to the EU numbering system.

B. Conformational Analysis

In another embodiment, the methods for identifying the target amino acid(s) comprise an analysis (e.g. visual inspection or computational analysis) of a starting polypeptide (e.g., an Fc-containing polypeptide) and/or a starting polypeptide bound to an Fc receptor (e.g., FcRn).

The three-dimensional structure of a protein influences its biological activity and stability, and that structure can be determined or predicted in a number of ways. Generally, empirical methods use physical biochemical analysis. Alternatively, tertiary structure can be predicted using model building of three-dimensional structures of one or more homologous proteins (or protein complexes) that have a known three-dimensional structure. X-ray crystallography is perhaps the best-known way of determining protein structure (accordingly, the term "crystal structure" may be used in place of the term "structure") (for example, the crystal structure of the human IgG1 Fc region has been determined (Disenhofer et al., Biochemistry, (1981), 20: 2361-70)), but estimates can also be made using circular dichroism, light scattering, or by measuring the absorption and emission of radiant energy. Other useful techniques include neutron diffraction, nuclear magnetic resonance (NMR), and homology modeling. All of these methods are known to those of ordinary skill in the art, and they have been well described in standard textbooks (see, e.g., *Physical Chemistry*, 4th Ed., W. J. Moore, Prentiss-Hall, N.J., 1972, or *Physical Biochemistry*, K. E. Van Holde, Prentiss-Hall, N.J., 1971)) and numerous publications. Any of these techniques can be carried out to determine the structure of an Fc region, a polypeptide comprising an Fc region (or FcRn binding portion thereof), or a complex of the polypeptide and FcRn, which can then be analyzed according to predict amino acids for substitution and/or used to inform one or more steps of a procedure (e.g., such as those described infra).

Methods for forming crystals of an antibody, an antibody fragment, or scFv-antigen complex have been reported by, for example, van den Elsen et al. (*Proc. Natl. Acad. Sci. USA* 96:13679-13684, 1999, which is expressly incorporated by reference herein). Such art-recognized techniques can be carried out to determine the structure of a complex containing an Fc-containing polypeptide and FcRn for analysis according to the methods of the present invention. Alternatively, published structures of the complex, or data corresponding thereto, may be readily available from a commercial or public database, e.g. the Protein Data Bank. In addition, the co-crystal structure (2.8 Å) of rat FcRn and a heterodimeric rat Fc containing a single FcRn binding site has recently been obtained (e.g. Martin et al., Molecular Cell, (2001), 7: 867-77). Where the structure of a complex (e.g. an X-ray structure) or data corresponding thereto is not known or available, a homology model using a related complex (e.g. from another species or a homologous ligand/receptor complex) may be utilized. For example, the crystal structure of the rat Fc-FcRn complex can be used to model the interaction of human Fc with FcRn.

Data corresponding to the Fc/FcRn complex can be evaluated to determine a potential alteration site. In another embodiment, the methods comprise an analysis (e.g. structural or computational analysis) of conformational differences between a free (ie. unbound) Fc-containing polypeptide and an Fc-containing polypeptide bound to FcRn.

C. Electrostatic Optimization

The basic computational formulae used in carrying out the methods of the invention are provided in, e.g., U.S. Pat. No. 6,230,102, the contents of which are hereby incorporated by reference in the present application in their entirety. In one embodiment, polypeptides are altered (or "modified") according to the results of a computational analysis of electrostatic forces between the polypeptide and FcRn, preferably, in accordance to the discrete criteria or rules of the invention described herein. The computational analysis allows one to predict the optimal charge distribution within the polypeptide receptor complex, and one way to represent the charge distribution in a computer system is as a set of multipoles. Alternatively, the charge distribution can be represented by a set of point charges located at the positions of the atoms of the polypeptide. Once a charge distribution is determined (preferably, an optimal charge distribution), one can modify the polypeptide to match, or better match, that charge distribution.

The computational analysis can be mediated by a computer-implemented process that carries out the calculations described in U.S. Pat. No. 6,230,102 (or as described in Tidor and Lee, J. Chem. Phys. 106:8681, 1997; Kangas and Tidor, J. Chem. Phys. 109:7522, 1998). The computer program may be adapted to consider the real world context of polypeptide-FcRn binding (and unlike other methods, this methods of the invention take into account, e.g., solvent, long-range electrostatics, and dielectric effects in the binding between a polypeptide and FcRn in a solvent (e.g., an aqueous solvent such as water, phosphate-buffered saline (PBS), plasma, or blood)). The process is used to identify modifications to the polypeptide structure that will achieve a charge distribution on the modified polyeptide that minimizes the electrostatic contribution to binding free energy between the modified polypeptide and FcRn (compared to that of the unmodified ("starting") polypeptide. As is typical, the computer system (or device(s)) that performs the operations described here (and in more detail in U.S. Pat. No. 6,230,102) will include an output device that displays information to a user (e.g., a CRT display, an LCD, a printer, a communication device such as a modem, audio output, and the like). In addition, instructions for carrying out the method, in part or in whole, can be conferred to a medium suitable for use in an electronic device for carrying out the instructions. Thus, the methods of the invention are amendable to a high throughput approach comprising software (e.g., computer-readable instructions) and hardware (e.g., computers, robotics, and chips). The computer-implemented process is not limited to a particular computer platform, particular processor, or particular high-level programming language. A useful process is set forth in U.S. Pat. No. 6,230,102 and a more detailed exposition is provided in Lee and Tidor (*J Chem. Phys.* 106:8681-8690, 1997); each of which is expressly incorporated herein by reference.

The rules of the invention can be applied as follows. To modulate the FcRn-binding affinity of a polypeptide, for example, to reduce, improve, or restore such binding, basic sequence and/or structural data is first acquired.

In one embodiment, the candidate amino acid residue(s) may be selected from those residues which are determined to have sub-optimal or optimal binding affinity. Alternatively or additionally, a target amino acid residue(s) may be may be selected from residues within the Fc region that are adjacent to the residue with optimal or sub-optimal binding affinity. Typically, an electrostatic charge optimization is first used to determine the position(s) of the Fc region that are sub-optimal for binding (Lee and Tidor, *J. Chem. Phys.* 106:8681-8690, 1997; Kangas and Tidor, *J. Chem. Phys.* 109:7522-7545, 1998).

Then, one or more mutations (i.e., modifications) is subjected to further computational analysis. Based on these calculations, the binding affinity is then determined for a subset of modified polypeptides having one or more modifications according to the rules of the invention.

Using a continuum electrostatics model, an electrostatic charge optimization can be performed on each side chain of the amino acids in the Fc of the polypeptide. A charge optimization gives charges at atom centers but does not always yield actual mutation(s). Accordingly, a round of charge optimizations can be performed with various constraints imposed to represent natural side chain characteristics at the positions of interest. For example, an optimization can be performed for a net side chain charge of −1, 0, and +1 with the additional constraint that no atom's charge exceeded a particular value, e.g., 0.85 electron charge units. Candidate amino acid side chain positions, and residue modifications at these positions, are then determined based on the potential gain in electrostatic binding free energy observed in the optimizations.

Binding free energy difference (in kcal/mol) in going from the native residue to a completely uncharged sidechain isostere, i.e., a residue with the same shape but no charges or partial charges on the atoms can be calculated. Negative numbers indicate a predicted increase of binding affinity.

In those instances in which binding free energy difference is favorable ($\Delta G<-0.3$ kcal/mol) and associated with a transition from the native residue to a completely uncharged side chain isostere, i.e., a residue with the same shape but no charges or partial charges on the atoms, modifications from the set of amino acids with nonpolar sidechains, e.g., A, C, I, L, M, F, P, V are selected.

Where the binding free energy difference that can be obtained with an optimal charge distribution in the side chain and a net side chain charge of −1 is favorable ($\Delta G<-0.3$ kcal/mol), modifications from the set of amino acids with negatively charged side chains, e.g., D, E are selected.

Similarly, where the binding free energy difference that can be obtained with an optimal charge distribution in the side chain and a net side chain charge of +1 is favorable ($\Delta G<-0.3$ kcal/mol), modifications from the set of amino acids with positively charged sidechains, e.g., R, H, K are selected.

Finally, in those cases where the binding free energy difference that can be obtained with an optimal charge distribution in the side chain and a net side chain charge of 0 is favorable ($\Delta G<-0.3$ kcal/mol), modifications from the set of amino acids with uncharged polar sidechains, e.g., N, C, Q, G, H, M, F, S, T, W, Y, to which are added C, G, M and F are selected.

As described herein, the designed modified polypeptides can be built in silico and the binding energy recalculated. Modified side chains can be built by performing a rotamer dihedral scan in CHARMM, using dihedral angle increments of 60 degrees, to determine the most desirable position for each side chain. Binding energies are then calculated for the wild type (starting) and mutant (modified) complexes using the Poisson-Boltzmann electrostatic energy and additional terms for the van der Waals energy and buried surface area.

Results from these computational modification calculations are then reevaluated as needed, for example, after subsequent reiterations of the method either in silico or informed by additional experimental structural/functional data. The rules allow for several predictions to be made which can be categorized as follows:

1) modifications at the interaction interface involving residues on the polypeptide that become partially buried upon binding FcRn (interactions are improved by making hydrogen bonds);

2) modifications of polar residues on the polypeptide that become buried upon binding and thus pay a desolvation penalty but do not make any direct electrostatic interactions with the receptor (improvements are usually made by modifying to a hydrophobic residue with similar shape to the wild-type residue or by adding a residue that can make favorable electrostatic interactions); and 3) modifications of surface residues on the polypeptide that are in regions of uncomplementary potentials. These modifications are believed to improve long-range electrostatic interactions between the polypeptide and FcRn without perturbing packing interactions at the binding interface.

Thus practiced, the rules of the invention allow for the successful prediction of affinity altering, (e.g., reducing or enhancing), side chain modifications. These findings can be classified into three general classes of modifications. The first type of modification involves residues at the interface across from a charged group on the antigen capable of making a hydrogen bond; the second type involves buried polar residues that pay a desolvation penalty upon binding but do not make back electrostatic interactions; and the third type involves long-range electrostatic interactions.

The first type of modification is determined by inspection of basic physical/chemical considerations, as these residues essentially make hydrogen bonds with unsatisfied hydrogen partners of the antigen. Unlike other methods, the rules of the invention allowed for surprising residue modifications in which the cost of desolvation is allowed to outweigh the beneficial interaction energy.

The second type of modification represents still another set of modifications, as the energy gained is primarily a result of eliminating an unfavorable desolvation while maintaining non-polar interactions.

The third type of modification concerns long-range interactions that show potential for significant gain in affinity. These types of modifications are particularly interesting because they do not make direct contacts with the antigen and, therefore, pose less of a perturbation in the delicate interactions at the polypeptide-FcRn interface.

Accordingly, when the desired side chain chemistries are determined for the candidate amino acid position(s) according to the rules, the residue position(s) is then modified or altered, e.g., by substitution, insertion, or deletion, as further described herein.

In addition to the above rules for polypeptide modification, it is noted that certain determinations, e.g., solvent effects can be factored into initial (and subsequent) calculations of optimal charge distributions.

In one embodiment, preferred mutations (e.g. amino acid substitutions) that alter the effector function of a target antibody are selected on the basis of charge optimization data can be identified by predicting amino acid alteration (e.g. substitutions) in the Fc region that alter (e.g., enhance or reduce) binding to an Fc receptor at various pH levels (e.g., neutral pH of about 7.2-7.4; acidic pH of about 3.0-5.0 (e.g., 4.0); or basic pH of about 8.0-10.9 (e.g., 9.0).

A charge optimization results in a set of optimal charges at atom centers but does not yield actual mutation suggestions. Once a charge optimization is determined using the methods recited above, one or more of the target amino acid residues, or any adjacent amino acid residues in the polypeptide (e.g., residues in or around the $CH_2$ domain or the FcRn binding loop of the Fc region) can be altered (e.g. mutated) based on the results of the charge optimization. In this process the optimal charge distribution is analyzed and mutations are selected that are closer to optimal than the current residue. For example, amino acid substitutions may be selected that are a match for, a better match for, or are closer to optimal than the current residue. One, or more than one, mutation may be selected such that the optimal charge distribution is achieved. The preferred mutation may be selected by visual inspection of the data or by computation analysis of the data.

Presently, the software used to examine electrostatic forces models an optimal charge distribution and the user then determines what amino acid substitution(s) or alteration(s) would improve that distribution. Accordingly, such steps (e.g., examining the modeled, optimal charge distribution and determining a sequence modification to improve antigen binding) are, or can be, part of the methods now claimed. However, as it would not be difficult to modify the software so that the program includes the selection of amino acid substitutions (or alterations), in the future, one may need only examine that output and execute the suggested change (or some variation of it, if desired).

In one embodiment, an amino acid for substitution can be identified by predicting amino acid alteration (e.g. substitution) in the Fc region that alter (e.g., enhance or reduce) binding to an Fc receptor at various pH levels (e.g., neutral pH of about 7.2-7.4; acidic pH of about 3.0-5.0 (e.g., 4.0); or basic pH of about 8.0-10.9 (e.g., 9.0).

In one embodiment, the invention pertains to a method of modulating the binding affinity of an polypeptide comprising an FcRn binding portion of an Fc region to FcRn at two different pH levels comprising, determining a spatial representation of an optimal charge distribution of the amino acids of the polypeptide and associated change in binding free energy of the polypeptide when bound to FcRn in a solvent at a first pH level; determining a spatial representation of an optimal charge distribution of the amino acids of the antibody and associated change in binding free energy of the polypeptide when bound to FcRn in a solvent at a second pH level; identifying, based on a comparison of the charge distributions, residues that exhibit different charge distributions at the first and second pH levels, at least one candidate amino acid residue position of the polypeptide to be modified to alter the binding free energy of the polypeptide when bound to FcRn; and selecting an elected amino acid residue for substitution for said amino acid position, such that upon substitution of the elected amino acid residue, the affinity of the polypeptide for FcRn is modulated.

In one embodiment, the first pH is about 7.4. In one embodiment, the second pH is about 6.0.

In one embodiment, an amino acid of the starting polypeptide which is uncharged substituted with a charged amino acid. In another embodiment, an uncharged amino acid of the starting polypeptide is substituted with another uncharged amino acid. In another embodiment, an amino acid of the starting polypeptide (e.g., an uncharged or negatively charged amino acid) is substituted with a positively charged amino acid. Positively charged amino acids include histidine, lysine, and asparagine. In another embodiment, an amino acid of the starting polypeptide (e.g., an uncharged or positively charged amino acid) is substituted with a negatively charged amino acid. Negatively charged amino acids include aspartate (aspartic acid) and glutamate (glutamic acid). In another embodiment, an amino acid of the starting polypeptide (e.g., a negatively or positively charged amino acid) is substituted with a uncharged amino acid. In another embodiment, an amino acid of the starting polypeptide (e.g., ucharged amino acid) is substituted with a uncharged amino acid that has different charge distribution.

In certain embodiments, when introduced in the altered polypeptide, the amino acid which is substituted changes the charge of the polypeptide such that the altered polypeptide has a different net charge than the starting polypeptide. In certain other embodiments, when introduced in the altered polypeptide, the amino acid which is substituted does not change the charge of the polypeptide such that the altered polypeptide has the same net charge than the starting polypeptide but a different charge distribution.

In another embodiment, amino acids are grouped into the following three groups (1) non-polar amino acids that have uncharged side chains (e.g. A, L, I, V, G, P). These amino acids are usually implicated in hydrophobic interactions;

(2) amino acids having polar amino acids that have net zero charge, but have non-zero partial charges in different portions of their side chains (e.g. M, F, W, S, Y, N, Q, C). These amino acids can participate in hydrophobic interactions and electrostatic interactions.

(3) charged amino acids that can have non-zero net charge on their side chains (e.g. R, K, H, E, D). These amino acids can participate in hydrophobic interactions and electrostatic interactions.

In one embodiment, at least one mutation altering the affinity of polypeptide-Fc interaction is a mutation from one of the following three categories:

(1) mutations that change the charge distribution of the at the interaction interface or in the regions of uncomplimentary electrostatic potentials between FcRn and polypeptide away from the interface. These changes can include substitutions between the groups on polar, non-polar, and charged amino acids (they will always change the location of partial charges), as well as substitutions within the group of polar aminoacids and within the group of charged amino acids as long as they alter the charge distribution (for instance C has a partial negative charge on SG atom and partially positive on HG atom. Whereas N has a partial positive charge on SG, and HD atoms, and partial negative charge on ND and OD atoms; hence, substitution of C for N will ater charge distribution). For example, in one embodiment, a substitution of an amino acid that is non-polar (with zero charges at all atoms in a sidechain) with an amino acid that is polar (with a zero net charge, but having partial charges on atoms in a sidechain) or visa versa;

(2) mutations of polar or charged residues on the antibody that become buried upon binding, and thus pay a desolvation penalty (energetic cost of removal of solvent upon binding) but do not make any favorable electrostatic interactions with the FcRn. In this case improvements are made by mutation to non-polar amino acids that do not interact with solvent and, therefore, will not pay a desolvation penalty upon binding.

(3) mutations of surface residues that change the shape of the molecule, thus affecting the dielectric properties of the medium between polypeptide and FcRn. Since solvent has higher screening capacity (dielectric constant) than a protein, charges will interact stronger through protein than through solvent. Therefore, filling (or clearing) the space between charges on polypeptide and FcRn with protein side sidechains will modulate their interaction. These mutations include amino acid substitutions where substituent has a different shape of a sidechain than an original amino acid (all charges except for ones between isosteres: V to T, D to N, N to D, L to D, L to N, D to L, N to L, Q to E, and E to Q). For substitution with the group on non-polar amino acids, this phenomenon would be the only effect on electrostatic interaction between polypeptide and FcRn.

In a particular embodiment, the altered polypeptide comprises a substitution at an amino acid position corresponding to an EU position selected from the group consisting of 248, 249, 250, 251, 252, 254, 256, 255, 260, 257, 277, 281, 282, 287, 284, 285, 286, 288, 290; 304, 305, 306, 307, 309, 310, 312, 313, 315, 343, 374, 426, 428, 430, 431, 432, 434, or 438.

In more specific embodiment, the altered polypeptide can include any one or any combination (and up to all) of the following mutations: a substitution at EU position 248 with aspartate; a substitution at EU position 249 with arginine or lysine; a substitution at EU position 250 with arginine or lysine; a substitution at EU position 251 with arginine, lysine, or asparagine; a substitution at EU position 252 with serine or threonine; a substitution at EU position 254 with serine or threonine; a substitution at EU position 256 with arginine, glutamate, or lysine; a substitution at EU position 255 with leucine, aspartate or methionine; a substitution at EU position 260 with lysine; a substitution at EU position 257 arginine, aspartate, glutamate, or lysine; a substitution at EU position 277 with arginine, aspartate, glutamine, or lysine; a substitution at EU position 279 with glutamate; a substitution at EU position 281 with glutamine; a substitution at EU position 282 with arginine, aspartate, glutamate, or lysine; a substitution at EU position 287 with aspartate, glutamate, lysine, proline, or threonine; a substitution at EU position 284 with aspartate or glutamate; a substitution at EU position 285 with aspartate, glutamate or phenylalanine; a substitution at EU position 286 with aspartate, glutamate, or methionine; a substitution at EU position 288 with aspartate or glutamate; a substitution at EU position 290 with aspartate or glutamate; a substitution at EU position 304 with aspartate or glutamate; a substitution at EU position 305 with arginine; a substitution at EU position 306 with arginine, aspartate, glutamate, or lysine; a substitution at EU position 307 with arginine, aspartate, or glutamate; a substitution at position 309 with arginine, aspartate, lysine or glutamate; a substitution at EU position 310 with arginine, leucine, lysine or asparagine; a substitution at EU position 312 with arginine, asparagine, or lysine; a substitution at EU position 313 with aspartate, arginine, or lysine; a substitution at EU position 315 with aspartate or glutamate; a substitution at EU position 343 with glutamine or lysine; a substitution at EU position 345 with arginine or glutamine; a substitution at EU position 374 with arginine, lysine, or leucine; a substitution at EU position 376 with asparagine; a substitution at EU position 426 with arginine, aspartate, or glutamate; a substitution at EU position 428 with arginine, glutamine, or lysine; a substitution at EU position 430 with lysine; a substitution at EU position 431 with proline; a substitution at EU position 432 with arginine; a substitution at EU position 434 with lecuine or lysine; or a substitution at EU position 438 with glutamate.

In more specific embodiment, the substitution is introduced in the Fc region of IgG1 and is selected from one of the following mutations: K248D, D249R, D249K, T250R, T250K, L251R, L251K, L251N, M252S, M252T, M254S, M254T, T256R, T256E, T256K, R255D, R255L, R255M, T260K, T260R, T260K, T260Q, P257R, P257D, P257E, P257K, W277R, W277D, W277Q, W277K, V279E, G281Q, V282R, V282D, V282E, V282K, V282E, H287D, A287E, A287K, A287P, A287T, V284D, V284E, A287E, H287D, H285E, H285F, N286D, N286E, N286M, K288D, K288E, K290D, K290E, S304D, S304E, V305R, V306E, L306R, L306D, L306E, L306K, V307E, T307R, T307D, L309R, L309D, L309E, L309K, H310R, H310N, H310L, H310K, L312K, D312R, D312N, D312K, N313R, W313D, N313K, W313K, N315D, N315E, P343Q, P343K, E345R, P374R, P374L, P374K, D376N, S426R, S426D, S426E, E430K, A431P, L432R, N434K, N434L, or Q438E.

D. Side Chain Repacking

In another embodiment, the method for selecting a preferred amino acid substitution comprises the application of sidechain repacking techniques to a structure (e.g. the crystal structure or model) of a complex containing the Fc-containing polypeptide and the FcRn. In a sidechain repacking calculation, the target residues can be modified computationally, and the stability of the resulting Fc polypeptide mutants in the conformation bound to the FcRn's evaluated computationally. The sidechain repacking calculation generates a ranked list of the variants that have altered stability (i.e., altered intramolecular energy).

In another embodiment, the method for selecting a preferred amino acid substitution comprises the application of sidechain repacking techniques to a structure (e.g. a crystal structure or model) of a complex containing two polypeptides (e.g. an Fc-containing polypeptide and an FcRn. Mutants which result in a desired alteration (e.g. increase or decrease) of receptor binding affinity can then be selected for experimental expression.

The number of protein mutants that is evaluated computationally can be very large, since every variable amino acid position can be mutated into all 20 standard amino acids. Exemplary computational algorithms used to rank the results of the computational analysis include dead-end elimination and tree search algorithms (see for example, Lasters et al. (*Protein Eng.* 8:815-822, 1995), Looger and Helling a (*J. Mol. Biol.* 307:429-445, 2001), and Dahiyat and Mayo (*Protein Sci.* 5:895-903, 1996)).

E. 3-D Visualization

In one embodiment, a visual analysis (e.g. using a 3-D molecular visualizer) of a three-dimensional structure and/or model of polypetide-FcRn complex can be visually analysed to predict mutations that will favor or disfavor a particular molecular conformation.

In one embodiment the mutation results in an increase in affinity of an Fc-containing polypeptide for an Fc receptor by introducing additional contacts between amino acid residues of the mutated Fc-containing polypeptide and FcRn This can be achieved, for example, by substituting smaller amino acid side chains Fc-containing polypeptide (e.g. alanine, glycine, serine, aspartate, asparagine, valine, cysteine) with larger amino acid side chains (e.g. methionine, tryptophan, phenylalanine, tyrosine, leucine, isoleucine, lysine, arginine, glutamine, glutamate, proline, threonine, histidine). In another embodiment, the mutation results in a decrease in affinity of an Fc-containing polypeptide for an Fc receptor by altering amino acids of the Fc-containing polypeptide that are in contact with FcRn. This can be achieved, for example, by substituting larger amino acid side chains of the Fc-containing polypeptide (e.g. methionine, tryptophan, phenylalanine, tyrosine, leucine, isoleucine, lysine, arginine, glutamine, glutamate, proline, threonine, histidine) with smaller amino acid side chains (e.g. alanine, glycine, serine, aspartate, asparagine, valine, cysteine).

In one embodiment, one or more mutations are made in an FcRn binding loop of an Fc region. The FcRn binding loop is comprised of amino acid residues 280, 281, 282, 283, 284, 285, 286, 287, 288, 289, 290, 291, 292, 293, 294, 295, 296, 297, 298 and 299 according to EU numbering). This loop is illustrated in FIG. 1. In one embodiment, one or more mutations are made in an amino acid selected from the group consisting of: 280, 281, 282, 283, 284, 285, 286, 287, 288, 289, 291, 292, 293, 294, 295, 296, 297, 298 and 299 according to EU numbering. In one embodiment, a mutation made to one or more amino acids in the FcRn binding loop results in a reduction in binding affinity to FcRn. Preferably, a mutation made in one or more amino acids in the FcRn binding loop results in an increase in binding affinity to FcRn. In one embodiment, the invention pertains to a method of enhancing half-life of a polypeptide of the invention comprising mutating at least one amino acid residue in the FcRn binding loop. In another embodiment, the invention pertains to a composition for treating a subject that would benefit from treatment with an altered polypeptide of the invention having an increased half-life.

In another embodiment, one or more mutations are made in a 15 Å FcRn contact zone, for example at one or more at the following positions (exemplary amino acids for those positions are also listed) 243 F; 244 P; 245 P; 246 K; 247 P; 248 K; 249 D; 250 T; 251 L; 252 M; 253 I; 254 S; 255 R; 256 T; 257 P; 258 E; 259 V; 260 T; 261 C; 275 F; 276 N; 277 W; 278 Y; 279 V; 280 D; 282 V; 283 E; 284 V; 285 H; 286 N; 287 A; 288 K; 289 T; 290 K; 291 P; 292 R; 293 E; 302 V; 303 V; 304 S; 305 V; 306 L; 307 T; 308 V; 309 L; 310 H; 311 Q; 312 D; 313W; 314 L; 315 N; 316G; 317 K; 318 E; 319 Y; 336 I; 337 S; 338 K; 339 A; 340 K; 341 G; 342 Q; 343 P; 344 R; 345 E; 346 P; 347 Q; 348 V; 367 C; 369 V; 372 F; 373 Y; 374 P; 375 S; 376 D; 377 I; 378 A; 379 V; 380 E; 381 W; 382 E; 383 S; 384 N; 385 G; 386 Q; 387 P; 388 E; 389 N; 391 Y; 393 T; 408 S; 424 S; 425 C; 426 S; 427 V; 428 M; 429 H; 430 E; 431 A; 432 L; 433 H; 434 N; 435 H; 436 Y; 437 T; 438 Q; 439 K; and 440 S (EU numbering).

F. Panning Libraries of FcR Mutants

In another embodiment, a multimeric FcRn receptor of the invention (i.e., an FcRn—Fc fusion protein as described in further detail herein) may be employed to assay alterations in the effector function of the members of any available library of Fc polypeptides. For example, the multimeric Fc receptors of the invention may be used to screen or "pan" a phage library of mutated Fc-containing polypeptides. A phage display library typically comprises phage particles that express the mutated Fc-containing polypeptide or Fc regions or regions or portions thereof that contain the mutation from a polynucleotide sequence inserted in the phage genome. Therefore, phage libraries, may include within them a phage particle that expresses every member of a repertoire or combinatorial library of mutated Fc-polypeptides. Phage used in these methods are typically filamentous phage, including fd and M13. The mutated Fc portion is typically expressed on the surface of the phage as a fusion with a viral coat protein (e.g. phage gene III or VIE proteins). Methods for making phage libraries are known in the art (see Brinkman et al., J. Immunol. Methods, (1995), 182: 41-50; Ames et al., J. Immunol. Methods, (1995), 184: 177-86; Kettleborough et al., (1994), 24: 952-8; Persic et al., Gene, (1997), 187: 9-18; Burton et al., Advances in Immunol., (1994), 57: 191-280. Alternatively, an existing phage display library may be screened. Available libraries include the library of altered Fc polypeptides described in WO 02/060919.

Phage expressing an Fc region that binds the multimeric Fe receptors of the invention with either higher or lower affinity than the starting polypeptide can be selected or identified, e.g. using labeled multimeric FcRn that is bound or immobilized on a solid surface (e.g. a bead). It could also be used in FACS sorting to select cells expressing a higher affinity form of the Fc region.

Using such methods, altered forms of Fe molecules can be tested for alteration in their binding affinity for FcRn and those molecules with the desired increase or decrease in binding affinity selected.

G. Further Optimization of FcRn Binding Affinity

An altered polypeptide generated by the methods of the invention can be re-modeled and further altered to further modulate FcR binding (e.g., to further enhance or further decrease binding). Thus, the steps described above can be followed by additional steps, including, e.g.,: (a) obtaining data corresponding to the structure of a complex between the altered or "second" polypeptide and the receptor;
(b) determining, using the data (which we may refer to as "additional data" to distinguish it from the data obtained and used in the first "round"), a representation of an additional charge distribution with the constant region of the second polypeptide that minimizes electrostatic contribution to binding free energy between the second polypeptide and the receptor; and (c) expressing a third polypeptide that binds to the receptor, the third polypeptide having a sequence that differs from that of the second polypeptide by at least one amino acid residue. In addition, empirical binding data can be used to inform further optimization. Yet additional rounds of optimization can be carried out.

IV. Methods of Altering Polypeptides

Having arrived at a desired mutation to make in a starting polypeptide one can use any of a variety of available methods to produce an altered polypeptide comprising the mutation. Such polypeptides can, for example, be produced by recombinant methods. Moreover, because of the degeneracy of the genetic code, a variety of nucleic acid sequences can be used to encode each desired polypeptide.

Exemplary art recognized methods for making a nucleic acid molecule encoding an amino acid sequence variant of a starting polypeptide include, but are not limited to, preparation by site-directed (or oligonucleotide-mediated) mutagenesis, PCR mutagenesis, and cassette mutagenesis of an earlier prepared DNA encoding the polypeptide.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA.

PCR mutagenesis is also suitable for making amino acid sequence variants of the starting polypeptide. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the parent DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a polypeptide variant can be determined, and a nucleic acid sequence encoding such amino acid sequence variant can be generated synthetically.

It will be understood by one of ordinary skill in the art that the polypeptides of the invention having altered FcRn binding may further be modified such that they vary in amino acid sequence, but not in desired activity. For example, additional nucleotide substitutions leading to amino acid substitutions at "non-essential" amino acid residues may be made to the protein For example, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members, i.e., a conservative substitutions, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Aside from amino acid substitutions, the present invention contemplates other modifications of the starting Fc region amino acid sequence in order to generate an Fc region variant with altered effector function. One may, for example, delete one or more amino acid residues of the Fc region in order to reduce or enhance binding to an FcR. In one embodiment, one or more of the Fc region residues can be modified in order to generate such an Fc region variant. Generally, no more than one to about ten Fc region residues will be deleted according to this embodiment of the invention. The Fc region herein comprising one or more amino acid deletions will preferably retain at least about 80%, and preferably at least about 90%, and most preferably at least about 95%, of the starting Fc region or of a native sequence human Fc region.

One may also make amino acid insertion Fc region variants, which variants have altered effector function. For example, one may introduce at least one amino acid residue (e.g. one to two amino acid residues and generally no more than ten residues) adjacent to one or more of the Fc region positions identified herein as impacting FcR binding. By "adjacent" is meant within one to two amino acid residues of a Fc region residue identified herein. Such Fc region variants may display enhanced or diminished FcRn binding.

Such Fc region variants will generally comprise at least one amino acid modification in the Fc region. In one embodiment amino acid modifications may be combined. For example, the variant Fc region may include two, three, four, five, etc substitutions therein, e.g. of the specific Fc region positions identified herein. In another embodiment, an altered polypeptide may have altered binding to FcRn and to another Fc receptor.

The Fc region consists of two identical protein chains. Accordingly, in one embodiment, the mutations are applied to both protein chains. In another embodiment, the mutations are applied only in one protein chain.

V. Preferred Alterations

Altered polypeptides of the invention contain at least one mutation (e.g. an amino acid substitution) within their Fc region. In one embodiment, the substituted amino acid(s) are located within the CH2 domain of the Fc region. In another embodiment, the substituted amino acid(s) are located within the CH3 domain of the Fc region. In another embodiment, substituted amino acids are located within both the CH2 and CH3 domain of the Fc region.

In one embodiment, an altered polypeptide of the invention comprises at least one amino acid mutation in the Fc region that serve to enhance the half-life of molecules in the blood. Molecules with increased half-life have the advantage of concurrently decreasing the periodic dosing of the drug or alternatively decreasing the dose of the drug and maintain the same pharmoacokinetic profile.

In another embodiment, an altered polypeptide of the invention comprises at least one amino acid mutation in the Fc region that serves to decrease the half-life of the antibody in the blood. Molecules with decreased half-life have the advantage of decreased dosing and exposure time to the patient. This is especially important if the altered antibody conjugated to toxic or radioactive drugs (e.g. anti-cancer therapeutics) diagnostic labels, since a balance between the antibody's non-specific and specific binding must be achieved.

Alteration in half-life or other antigen-independent effector functions may be predicted from a difference between the starting antibody and the altered antibody with respect to their FcRn binding affinity.

In another exemplary embodiment, tissue distribution or bioavailability of the polypeptide is modulated by modulating FcRn binding affinity. In one embodiment an altered polypeptide of the invention comprises at least one amino acid mutation in the Fc region results in an enhanced localization of the polypeptide to a specific target tissue, such as a mucosal surface or a disease site, e.g. a tumor or other specific diseases characterized by pathology.

In another embodiment, an altered polypeptide of the invention comprises at least one amino acid mutation in the Fc region that results in a reduced localization of the altered polypeptide to tissues which are sensitive to the effects of the unaltered starting polypeptide. In an exemplary embodiment, the altered polypeptide exhibits reduced placental transfer from the circulatory system of the mother to the tissues of the fetus. Other sensitive tissues for which reduced (or enhanced) localization are likely to be beneficial include the brain, kidney, and liver. In one exemplary embodiment, the altered polypeptides of the invention exhibit reduced transport across the epithelium of kidney glomeruli from the vasculature. In another embodiment, the altered polypeptides of the invention exhibit reduced transport across the blood brain barrier (BBB) from the brain.

In another embodiment, an altered polypeptide of the invention comprises at least one amino acid mutation in the Fc region that results in reduced FcRn-mediated binding of aggregated IgG to glomerular epithelial cells and less membranous nephropathy than a starting antibody lacking the mutation. (Hayman et al. 2004. Nephron Exp. Nephrol. 90:e13-e21)

Enhancement or diminishment of tissue localization of the Fc (or Fc-containing polypeptide) is reflected, respectively, in the increase or decrease of the Fc region affinity for FcRn (neonatal Fc receptor). Similarly, the correlation of FcRn binding affinity and tissue distribution or bioavailability of an Fc polypeptide is also consistent with the biological role of FcRn in facilitating the transport of antibody across epithelial barriers by transcytosis.

In some embodiments, the altered polypeptides of the invention will exhibit altered antigen-independent effector functions without altering antigen-dependent effector functions (e.g. ADCC or CDC). In other embodiments, the altered polypeptides will alteration in both antigen-independent effector function and antigen-dependent effector functions. In one embodiment, one or more the mutations disclosed herein may confer increased antigen-dependent effector function and decreased half-life.

In another embodiment, one or more the mutations disclosed herein may confer increased antigen-dependent effector function and increased half-life. In another embodiment, one or more the mutations disclosed herein may confer decreased antigen-dependent effector function and decreased half-life. In another embodiment, one or more the mutations disclosed herein may confer decreased antigen-dependent effector function and increased half-life.

In particular embodiments, the altered polypeptide comprises a substitution at an amino acid position corresponding to an EU amino acid position selected from the group consisting of 248, 249, 250, 251, 252, 255, 256, 257, 258, 260, 277, 279, 280, 281, 282, 283, 284, 285, 286, 287, 288, 289, 290, 304, 305, 306, 307, 309, 310, 311, 312, 313, 314, 315, 316, 317, 340, 343, 344, 345, 374, 376, 378, 383, 386, 387, 389, 426, 428, 430, 431, 432, 434, 436, or 438.

In an exemplary embodiment, the altered polypeptide comprises a substitution in an amino acid of the 15 Å FcRn contact region or "zone" (e.g. from EU position 243 to 261, from EU position 275 to EU position 280, from EU position 282 to EU position 293, from EU position 302 to EU position 319, from EU position 336 to EU position 348, EU position 367, EU position 369, from EU position 372 to EU position 389, EU position 391, EU position 393, EU position 408, and from EU position 424 to EU position 440.

In another exemplary embodiment, the altered polypeptide comprises a substitution in the FcRn contact loop comprising EU amino acid positions 280, 281, 282, 283, 284, 285, 286, 287, 288, 289, 290, 291, 292, 293, 294, 295, 296, 297, 298, and 299.

Exemplary Fc region (or FcRn binding portion thereof) sites for mutation include EU positions 280, 281, 282, 283, 285, 286, 288, 289, 290, 305, 307, 308, 309, 315, 340, 344, and 378.

In another embodiment, the altered polypeptide can include any one or any combination (and up to all) of the following mutations: a substitution at EU position 248 with aspartate; a substitution at EU position 249 with arginine or lysine; a substitution at EU position 250 with arginine or lysine; a substitution at EU position 251 with arginine, lysine, or asparagine; a substitution at EU position 252 with glutamine, asparagines, serine or threonine; a substitution at EU position 255 with methionine, aspartate, or leucine; a substitution at EU position 256 with arginine, glutamate, or lysine; a substitution at EU position 257 arginine, aspartate, glutamate, or lysine; a substitution at EU position 258 with arginine, glutamine, or lysine; a substitution at EU position 260 with lysine; a substitution at EU position 277 with arginine, aspartate, glutamine, or lysine; a substitution at EU position 279 with arginine, aspartate, glutamate, or lysine; a substitution at EU position 280 with asparagine; a substitution at EU position 281 with aspartate glutamate, or glutamine; a substitution at EU position 282 with arginine, aspartate, glutamate, or lysine; a substitution at EU position 283 with glutamine; a substitution at EU position 284 with arginine, lysine, aspartate or glutamate; a substitution at EU position 285 with arginine, aspartate, glutamate, lysine, proline, threonine, or phenylalanine; a substitution at EU position 286 with aspartate, glutamate, threonine, or methionine; a substitution at EU position 287 with aspartate, glutamate, lysine, proline, or threonine; a substitution at EU position 288 with methionine, arginine, aspartate or glutamate; a substitution at EU position 289 with proline; a substitution at EU position 290 with proline, aspartate or glutamate; a substitution at EU position 304 with aspartate or glutamate; a substitution at EU position 305 with arginine or threonine; a substitution at EU position 306 with arginine, aspartate, glutamate, or lysine; a substitution at EU position 307 with arginine, proline, aspartate, or glutamate; a substitution at EU position 308 with arginine, aspartate, glutamate, lysine, or isoleucine; a substitution at position 309 with threonine, arginine, aspartate, lysine or glutamate; a substitution at EU position 310 with arginine, leucine, lysine or asparagine; a substitution at EU position 311 with arginine or lysine; a substitution at EU position 312 with arginine, asparagine, leucine, or lysine; a substitution at EU position 313 with aspartate, arginine, or lysine; a substitution at EU position 314 with arginine, lysine, or asparagine; a substitution at EU position 315 with arginine, aspartate or glutamate; a substitution at EU position 316 with aspartate or lysine; a substitution at EU position 317 with aspartate or glutamate; a substitution at EU position 340 with arginine; a substitution at EU position 343 with glutamine or lysine; a substitution at EU position 344 with leucine; a substitution at EU position 345 with arginine, lysine, or glutamine; a substitution at EU position 374 with arginine, lysine, or leucine; a substitution at EU position 376 with asparagine, arginine, leucine, or lysine; a substitution at EU position 378 with serine; a substitution at EU position 383 with lysine; a substitution of glycine at EU position 385 with lysine; a substitution glutamine at EU position 386 with alanine or lysine; a substitution at EU position 387 with alanine; a substitution at EU position 389 with aspartate; a substitution at EU position 426 with arginine, aspartate, or glutamate; a substitution at EU position 428 with aspartate, glutamate, arginine, glutamine, or lysine; a substitution at EU position 430 with arginine, glutamine, methionine, or lysine; a substitution at EU position 431 with lysine or proline; a substitution at EU position 432 with arginine with phenylalanine; a substitution at EU position 434 with leucine, arginine, or lysine; a substitution at EU position 436 with arginine or glutamate; or a substitution at EU position 438 with glutamate.

More specifically, the altered polypeptide can include any one or any combination (and up to all) of the following mutations: a substitution of lysine at EU position 248 with aspartate; a substitution of aspartate at EU position 249 with arginine or lysine; a substitution of threonine at EU position 250 with arginine or lysine; a substitution of leucine at EU position 251 with arginine, lysine, or asparagine; a substitution of methionine at EU position of 252 with glutamine, asparagine, serine or threonine; a substitution of arginine at EU position 255 with methionine, aspartate, or leucine; a substitution of threonine at EU position 256 with arginine, glutamate, or lysine; a substitution of proline at EU position 257 arginine, aspartate, glutamate, or lysine; a substitution of glutamate at EU position 258 with arginine, glutamine, or lysine; a substitution of threonine at EU position 260 with lysine; a substitution of tryptophan at EU position 277 with arginine, aspartate, glutamate, glutamine, or lysine; a substitution of valine at EU position 279 with arginine, aspartate, glutamate, or lysine; a substitution of aspartate at EU position 280 with asparagine; a substitution of glycine at EU position 281 with aspartate, glutamate, or glutamine; a substitution of valine at EU position 282 with arginine, aspartate, glutamate, or lysine; a substitution of glutamate at EU position 283 with glutamine; a substitution of valine at EU position 284 with arginine, lysine, aspartate or glutamate; a substitution of histidine or alanine at EU position 285 with arginine, aspartate, glutamate, lysine, proline, threonine, or phenylalanine; a substitution of asparagines or lysine at EU position 286 with aspartate, glutamate, threonine, or methionine; a substitution of alanine at EU position 287 with aspartate, glutamate, lysine, proline, or threonine; a substitution of lysine at EU position 288 with methionine, arginine, aspartate or glutamate; a substitution threonine at EU position 289 with proline; a substitution lysine at EU position 290 with proline, aspartate or glutamate; a substitution of serine at EU position 304 with aspartate or glutamate; a substitution of valine at EU position 305 with arginine or threonine; a substitution of leucine or valine at EU position 306 with arginine, aspartate, glutamate, or lysine; a substitution threonine or valine at EU position 307 with arginine, proline, aspartate, or glutamate; a substitution of valine at EU position 308 with arginine, aspartate, glutamate, lysine, or isoleucine; a substitution of leucine at EU position 309 with threonine, arginine, aspartate, lysine or glutamate; a substitution of histidine at EU position 310 with arginine, leucine, lysine or asparagine; a substitution of glutamine at EU position 311 with arginine or lysine; a substitution of aspartate or leucine at EU position 312 with arginine, asparagine, leucine, or lysine; a substitution of asparagine at EU position 313 with aspartate, arginine, or lysine; a substitution of leucine at EU position 314 with arginine, lysine, or asparagine; a substitution asparagine at EU position 315 with arginine, aspartate or glutamate; a substitution of asparagine or glycine at EU position 316 with aspartate or lysine; a substitution of lysine at EU position 317 with aspartate or glutamate; a substitution of lysine at EU position 340 with arginine a substitution proline at EU position 343 with glutamine or lysine; a substitution of arginine at EU position 344 with leucine; a substitution of glutamate at EU position 345 with arginine, lysine, or glutamine; a substitution proline at EU position 374 with arginine, lysine, or leucine; a substitution of aspartate at EU position 376 with asparagine, arginine, leucine, or lysine; a substitution of alanine at EU position 378 with serine; a substitution of serine at EU position 383 with lysine; a substitution of glycine at EU position 385 with lysine; a substitution glutamine at EU position 386 with alanine or lysine; a substitution of proline at EU position 387 with alanine; a substitution of asparagine at EU position 389 with aspartate; a substitution of serine at EU position 426 with arginine, aspartate, or glutamate; a substitution of methionine at EU position 428 with aspartate, glutamate, arginine, glutamine, or lysine; a substitution of glutamate at EU position 430 with arginine, glutamine, methionine, or lysine; a substitution of leucine at EU position 431 with lysine or to proline; a substitution of histidine at EU position 432 with arginine with phenylalanine; a substitution of asparagine at EU position 434 with leucine, arginine, or lysine; a substitution of tyrosine at EU position 436 with arginine or glutamate; or a substitution of glutamine at EU position 438 with glutamate.

In another embodiment, a polypeptide of the invention may contain at least one amino acid mutation selected from the group consisting of: a substitution at EU position 281 with E, a substitution at EU position 282 with E, a substitution at EU position 283 with Q, a substitution at EU position 285 with R, a substitution at EU position 286 with T, a substitution at EU position 288 with R, a substitution at EU position 289 with P, a substitution at EU position 290 with P, a substitution at EU position 305 with T, a substitution at EU position 307 with P, a substitution at EU position 308 with I, a substitution at EU position 309 with T, a substitution at EU position 315 with R, a substitution at EU position 340 with R, a substitution at EU position 344 with L, a substitution at EU position 378 with S, a substitution at EU position 383 with K, a substitution at EU position 385 with K, a substitution at EU position 386 with A, and a substitution at EU position 389 with D, according to the EU numbering system.

More specifically, a polypeptide of the invention may contain at least one amino acid mutations selected from the group consisting of: Asp280Asn (where D indicates amino acid position to be mutated at the recited EU position (280) and where N indicates the amino acid to be substituted at that position to arrive at the altered polypeptide), Gly281Glu, Val282Glu, Glu283Gln, His285Arg, Asn286Thr, Lys288Arg, Thr289Pro, Lys290Pro, Val305Thr, Thr307Pro, Val308I1e, Leu309Thr, Asn315Arg, Lys340Arg, Arg344Leu, Ala378Ser, Ser383Lys, Glu386Lys, Pro387Ala, and Asn389Asp, according to the EU numbering system.

In a particular embodiment, the altered polypeptide comprises a substitution at an amino acid position corresponding to an EU position selected from the group consisting of 248, 249, 250, 251, 252, 256, 255, 260, 257, 277, 281, 282, 287, 284, 285, 286, 288, 290; 304, 305, 306, 307, 309, 310, 312, 313, 315, 343, 374, 426, 428, 430, 431, 432, 434, or 438.

In another embodiment, the altered polypeptide can include any one or any combination (and up to all) of the following mutations: a substitution at EU position 248 with aspartate; a substitution at EU position 249 with arginine or lysine; a substitution at EU position 250 with arginine or lysine; a substitution at EU position 251 with arginine, lysine, or asparagine; a substitution at EU position 252 with serine or threonine; a substitution at EU position 256 with arginine, glutamate, or lysine; a substitution at EU position 255 with leucine, aspartate or methionine; a substitution at EU position 260 with lysine; a substitution at EU position 257 arginine, aspartate, glutamate, or lysine; a substitution at EU position 277 with arginine, aspartate, glutamine, or lysine; a substitution at EU position 279 with glutamate; a substitution at EU position 281 with glutamine; a substitution at EU position 282 with arginine, aspartate, glutamate, or lysine; a substitution at EU position 287 with aspartate, glutamate, lysine, proline, or threonine; a substitution at EU position 284 with aspartate or glutamate; a substitution at EU position 285 with aspartate, glutamate or phenylalanine; a substitution at EU position 286 with aspartate, glutamate, or methionine; a substitution at EU position 288 with aspartate or glutamate; a substitution at EU position 290 with aspartate or glutamate; a substitution at EU position 304 with aspartate or glutamate; a substitution at EU position 305 with arginine; a substitution at EU position 306 with arginine, aspartate, glutamate, or lysine; a substitution at EU position 307 with arginine, aspartate, or glutamate; a substitution at position 309 with arginine, aspartate, lysine or glutamate; a substitution at EU position 310 with arginine, leucine, lysine or asparagine; a substitution at EU position 312 with arginine, asparagine, or lysine; a substitution at EU position 313 with aspartate, arginine, or lysine; a substitution at EU position 315 with aspartate or glutamate; a substitution at EU position 343 with glutamine or lysine; a substitution at EU position 345 with arginine or glutamine; a substitution at EU position 374 with arginine, lysine, or leucine; a substitution at EU position 376 with asparagine; a substitution at EU position 426 with arginine, aspartate, or glutamate; a substitution at EU position 428 with arginine, glutamine, or lysine; a substitution at EU position 430 with lysine; a substitution at EU position 431 with proline; a substitution at EU position 432 with arginine; a substitution at EU position 434 with lecuine or lysine; or a substitution at EU position 438 with glutamate.

In another embodiment, the substitution is introduced in the Fc region of IgG1 and is selected from one of the following mutations: K248D, D249R, D249K, T250R, T250K, L251R, L251K, L251N, M252S, M252T, M252Q, M252N, R255D, R255L, R255M, T256R, T256E, T256K, P257R, P257D, P257E, P257K, E258R. E258Q. E258K, T260K, T260R, T260K, T260Q, W277R, W277D, W277Q, W277E, W277K, V279R, V279D, V279E, V279K, D280N, G281D, G281E, G281Q, V282R, V282D, V282E, V282K, E283Q, V284R, V284D, V284E, V284K, H285R, H285D, H285E, H285K, H285P, H285T, H285F, A285D, A285E, N286D, N286E, N286T, N286M, A286M, A286E, A286D, A287D, A287E, A287K, A287P, A287T, K288D, K288E, K288M, K288R, T289P, K290D, K290E, K290P, S304D, S304E, V305T, V305R, V306D, V306E, L306R, L306D, L306E, L306K, V307E, T307R, T307D, T307P, V308R, V308D, V308E, V308K, V308I, L309R, L309D, L309E, L309K, L309T, H310R, H310N, H310L, H310K, L312K, Q311 R, Q311 K, D312R, D312N, D312L, D312K, L312K, N313R, N313K, W313D, N313K, W313K, L314R, L314N, L314K, N315R, N315D, N315E, N316D, N316K, K317D, K317E, K340R, P343Q, P343K, R344L, E345R, E345Q, E345R, P374R, P374L, P374K, D376R, D376L, D376K, D376N, A378S, S383K, G385K, Q386A, Q386K, P387A, N389D, S426R, S426D, S426E, M428R, M428D, M428E, E430R, E430Q, E430K, E430M, A431P, L431K, H432F, L432R, N434R, N434K, N434L, Y436R, Y436E, or Q438E.

As set forth above it will be understood that the subject compositions may comprise one or more of the mutations set forth herein. In one embodiment, the altered polypeptides of the invention comprise only one of the mutations listed herein. In one embodiment, the altered polypeptides of the invention comprise only two of the mutations listed herein. In one embodiment, the altered polypeptides of the invention comprise only three of the mutations listed herein. In one embodiment, the altered polypeptides of the invention comprise only four of the mutations listed herein.

A. Altered Polypeptides with Enhanced FcRn Binding Affinity

In one embodiment, the present invention provides altered polypeptides with an enhanced affinity for a neonatal Fc receptor as compared to their corresponding starting polypeptides. Preferably the altered polypeptides exhibit a circulatory half-life than is longer than a comparable polypeptide that does not contain the mutation.

In one embodiment, altered polypeptide with enhanced FcRn binding affinity may comprise at least one amino acid substitution at one of the following EU positions: 284, 285, 286, 288, 290, and 304.

In another embodiment, the altered polypeptide with enhanced FcRn binding affinity may comprise at least one of the following amino acid substitutions: a substitution at EU position 284 with glutamate; a substitution at EU position 285 with glutamate; a substitution at EU position 286 with aspartate; a substitution at EU position 288 with glutamate; and a substitution at EU position 290 with glutamate.

In one exemplary embodiment, said altered polypeptide comprises an Fc region of an IgG1 molecule. Preferably the molecule contains at least one of the following mutations: V282E, V284E, H285E, N286D, N286E, K288E, K290E, and S304D.

In a preferred embodiment of the present invention, the binding affinity for FcRn of the modified polypeptide is increased by at least about 30%, 50%, 80%, 2-fold, 3-fold, 4-fold, 5-fold, 10-fold, 15-fold, 20-fold, 25-fold, 30-fold, 40-fold, 50-fold, 60-fold, 70-fold, 80-fold, 90-fold, or 100-fold over the starting polypeptide.

When administered to a patient, the altered polypeptides of the invention may have a circulatory half-life in a patient of greater than 1 hours, 2 hours, 3 hours, 4 hours, 5 hours, 10 hours, 12 hours, 24 hours, 2 days, 3 days, 4 days, 5 days, 10 days, 12 days, 2 weeks, 3 weeks, or 1 month. In an exemplary embodiment, the altered polypeptides of the invention have a circulatory half-life in a patient of greater than 21 days.

In one embodiment, the altered binding molecule may have enhanced localization to, or bioavailability in, a particular target tissue, for example a diseased tissue. Exemplary diseased tissues include neoplastic tissues or tumors or other tissues or organs characterized by pathology of any of the disorder described herein, including including the brain or CNS, lungs, heart, pancreas, liver, kidney, bladder, stomach, large or small intestine, respiratory tract, lymph nodes, muscle, epidermis, bone, cartilage, joints, blood vessels, bone marrow, prostate, ovary, or uterus.

B. Altered polypeptides with Reduced FcRn Binding Affinity

In another embodiment, the present invention provides altered polypeptides with reduced affinity for a neonatal Fc receptor as compared to their corresponding starting polypeptides. Preferably the altered polypeptides exhibit a circulatory half-life than is shorter than a comparable polypeptide that does not contain the mutation.

The altered polypeptide with reduced FcRn binding affinity may comprise at least one amino acid substitution at an EU position, wherein the EU position is selected from within one of the following regions: a) from position 248 to position 260; b) from position 277 to position 315; c) from position 343 to position 374; and d) from position 426 to position 438.

In one embodiment, altered polypeptide with reduced FcRn binding affinity may comprise at least one amino acid substitution at one of the following EU positions: 248, 249, 250, 251, 252, 256, 255, 260, 257, 277, 281, 282, 287, 284, 285, 286, 288, 290; 304, 305, 306, 307, 309, 310, 312, 313, 315, 343, 374, 426, 428, 430, 431, 432, 434, or 438.

In another embodiment, altered Fc polypeptide with reduced FcRn binding affinity may comprise at least one of the following amino acid substitutions: a substitution at EU position 248 with aspartate; a substitution at EU position 249 with arginine or lysine; a substitution at EU position 250 with arginine or lysine; a substitution at EU position 251 with arginine, lysine, or asparagine; a substitution at EU position 252 with serine or threonine; a substitution at EU position 256 with arginine, glutamate, or lysine; a substitution at EU position 255 with leucine, aspartate or methionine; a substitution at EU position 260 with lysine; a substitution at EU position 257 arginine, aspartate, glutamate, or lysine; a substitution at EU position 277 with arginine, aspartate, glutamine, or lysine; a substitution at EU position 279 with glutamate; a substitution at EU position 281 with glutamine; a substitution at EU position 282 with arginine, aspartate, glutamate, or lysine; a substitution at EU position 287 with aspartate, glutamate, lysine, proline, or threonine; a substitution at EU position 284 with aspartate; a substitution at EU position 285 with aspartate or phenylalanine; a substitution at EU position 286 with glutamate or methionine; a substitution at EU position 288 with aspartate; a substitution at EU position 290 with aspartate or glutamate; a substitution at EU position 304 with aspartate or glutamate; a substitution at EU position 305 with arginine; a substitution at EU position 306 with arginine, aspartate, glutamate, or lysine; a substitution at EU position 307 with arginine, aspartate, or glutamate; a substitution at position 309 with arginine, aspartate, lysine or glutamate; a substitution at EU position 310 with arginine, leucine, lysine or asparagine; a substitution at EU position 312 with arginine, asparagine, or lysine; a substitution at EU position 313 with aspartate, arginine, or lysine; a substitution at EU position 315 with aspartate or glutamate; a substitution at EU position 343 with glutamine or lysine; a substitution at EU position 345 with arginine or glutamine; a substitution at EU position 374 with arginine, lysine, or leucine; a substitution at EU position 376 with asparagine; a substitution at EU position 426 with arginine, aspartate, or glutamate; a substitution at EU position 428 with arginine, glutamine, or lysine; a substitution at EU position 430 with lysine; a substitution at EU position 431 with proline; a substitution at EU position 432 with arginine; a substitution at EU position 434 with lecuine or lysine; or a substitution at EU position 438 with glutamate.

In another embodiment, the altered polypeptide can include any one or any combination (and up to all) of the following mutations: K248D, D249R, D249K, T250R, T250K, L251R, L251K, L251N, M255S, M255T, T256R, T256E, T256K, R255D, R255L, R255M, T260K, T260R, T260K, T260Q, P257R, P257D, P257E, P257K, W277R, W277D, W277Q, W277K, V279E, G281Q, V282R, V282D, V282E, V282K, V282E, A287D, A285E, A287K, A287P, A287T, V284D, H285D, H285F, N286E, N286M, K288D, K290D, K290E, S304D, S304E, V305R, V306E, L306R, L306D, L306E, L306K, V307E, T307R, T307D, L309R, L309D, L309E, L309K, H310R, H310N, H310L, H310K, L312K, D312R, D312N, D312K, N313R, W313D, N313K, W313K, N315D, N315E, P343Q, P343K, E345R, P374R, P374L, P374K, D376N, S426R, S426D, S426E, E430K, A431P, L432R, N434K, N434L, or Q438E.

In certain preferred embodiments, the altered Fc with reduced FcRn binding affinity may comprise at least one mutations: M252S, M252T, V282E, K288E; V308E, V308D, L314K, N434L, or Q438E. In more preferred embodiments, the altered polypeptide with reduced FcRn binding affinity may comprise at least one mutations: M252S, M252T, N434L, or Q438E. In a still more preferred embodiment, the altered Fc polypeptide with reduced FcRn binding comprises the mutation N434L or Q438 In another embodiment, the altered polypeptide with reduced FcRn binding affinity may comprise at least one of the following amino acid substitutions:

a substitution at EU position 252 with threonine; a substitution at EU position 255 with aspartate; a substitution at EU position 282 with arginine, aspartate, glutamate, or lysine; a substitution at position 309 with arginine, aspartate, lysine or glutamate; and a substitution at position 434 with leucine.

In one exemplary embodiment, the altered polypeptide comprises an Fc region of an IgG1 molecule. Preferably the molecule contains at least one of the following mutations M252T, R255D, V282R, V282D, V282E, V282K, L309R, L309D, L309K, L309E, or N434L In a preferred embodiment of the present invention, the binding affinity for FcRn of the modified polypeptide is reduced by at least about 30%, 40%, 50%, 60%, 70%, 80%, 85%, 90%, 95%, 97%, 98%, or 99% when compared with the starting polypeptide.

When administered to a patient, the altered polypeptides of the invention may have a circulatory half-life in a patient that is less than 1 hour, 2 hours, 3 hours, 4 hours, 5 hours, 10 hours, 12 hours, 24 hours, 2 days, 3 days, 4 days, 5 days, 10 days, 12 days, 2 weeks, 3 weeks, or 1 month. In an exemplary embodiment, the altered polypeptides of the invention have a circulatory half-life in a patient of less than about 21 days.

In one embodiment, the altered polypeptide may, have reduced localization to, or bioavailability in, a particular tissue, for example a tissue that is vulnerable to the toxicity from the unaltered binding molecule. Exemplary tissues which are typically vulnerable to the toxic effects of therapeutic agents include the brain or CNS, heart, liver, and kidneys. In another embodiment, the altered polypeptide may have reduced localization or placental transfer to a fetus. In another embodiment, the altered polypeptide may have reduced localization to the circulatory system of a neonate when ingested in the milk or colostrum.

V. Expression of Altered Polypeptides

The polypeptides of the invention, e.g., starting polypeptides and modified polypeptides be produced by recombinant methods.

For example, a polynucleotide sequence encoding a polypeptide can be inserted in a suitable expression vector for recombinant expression. Where the polypeptide is an antibody, polynucleotides encoding additional light and heavy chain variable regions, optionally linked to constant regions, may be inserted into the same or different expression vector. An affinity tag sequence (e.g. a His(6) tag) may optionally be attached or included within the starting polypeptide sequence to facilitate downstream purification. The DNA segments encoding immunoglobulin chains are the operably linked to control sequences in the expression vector(s) that ensure the expression of in polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the polypeptide.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The subject polypeptide can also be incorporated in transgenes for introduction into the genome of a transgenic animal and subsequent expression, e.g., in the milk of a transgenic animal (see, e.g., Deboer et al. 5,741,957; Rosen 5,304,489; and Meade 5,849,992. Suitable transgenes include coding sequences for light and/or heavy chains in operable linkage with a promoter and enhancer from a mammary gland specific gene, such as casein or beta lactoglobulin.

Altered polypeptides (e.g., polypeptides) can be expressed using a single vector or two vectors. For example, antibody heavy and light chains may be cloned on separate expression vectors and co-transfected into cells.

In one embodiment, signal sequences may be used to facilitate expression of polypeptides of the invention.

Once expressed, the polypeptides can be purified according to standard procedures of the art, including ammonium sulfate precipitation, affinity columns (e.g., protein A or protein G), column chromatography, HPLC purification, gel electrophoresis and the like (see generally Scopes, Protein Purification (Springer-Verlag, N.Y., (1982)). In a preferred embodiment, the purification procedure may employ the use of a multimeric Fc receptor of the invention as described below.

VI. Analysis of Binding Affinity

Binding affinity can be measured in a variety of ways. Generally, and regardless of the precise manner in which affinity is defined or measured, the methods of the invention modulate binding affinity to FcRn when they generate a polypeptide that is superior in any aspect of its clinical application to the starting polypeptide from which it was made (for example, the methods of the invention are considered effective or successful when a modified polypeptide can be administered at a lower dose or less frequently or by a more convenient route of administration or has reduced side effects or altered biodistribution.

An alteration in the effector function of an altered polypeptide can be determined by measuring its binding affinity for a particular Fc receptor. In one embodiment, an alteration of antigen-dependent effector function can be determined by measuring the binding affinity of the altered polypeptide for an Fc gamma receptor. In another embodiment, the antigen-independent effector functions (e.g. half-life or biodistribution) can be determined by measuring binding affinity to other Fc receptors, in particular a neonatal Fc receptor (e.g., human FcRn).

An alteration in the binding affinity of an altered polypeptide of the invention may be determined by comparing the binding affinity of the altered polypeptide with a suitable control polypeptide (e.g. the corresponding starting polypeptide). In one embodiment, an alteration of binding affinity may be determined by comparing the binding affinity of the altered polypeptide in first assay with the binding affinity of the control polypeptide in a second binding assay. In alternative embodiments, an alteration of binding affinity may be determined by comparing the binding affinity of the altered polypeptide and the control polypeptide in the same assay. For example, the assay may be performed as a competitive binding assay where the binding affinity of the altered polypeptide is evaluated with increasing concentrations of the control polypeptide. In a particular embodiment, the binding affinity for an Fc receptor (e.g. FcRn) can be determined at a first pH (e.g. an acidic pH) and a second pH (e.g. a basic pH).

More specifically, the affinity between a polypeptide and a receptor to which it binds can be measured by various assays, including, for example, surface plasmon resonance (e.g., a BiaCore assay), analytical ultracentrifugation, gel filtration, FRET, and ELISAI or the KinExA™ 3000 assay (available from Sapidyne Instruments (Boise, Id.)). Exemplary assays are described in more detail below.

i) Cell-Free Assays

Several in vitro, cell-free assays for testing the effector functions (e.g. FcR binding affinity) of altered polypeptides have been described in the art. Preferably, the cell-based assay is capable of evaluating binding of altered antibodies to soluble forms Fc receptors, e.g. monomeric Fc receptors or the multimeric Fc receptors of the invention. Automation and HTS technologies may be utilized in the screening procedures. Screening may employ the use of labels (e.g. isotopic labels, chromophores, fluorophore, lumiphores, or epitopes) that enable detection. The labels may be attached to the multimeric Fc receptor or the Fc-containing polypeptide that is assayed.

Exemplary cell-free assays include, but are not limited to, FRET (fluorescence resonance energy transfer), BRET (bioluminescence resonance energy transfer), Alphascreen (Amplied Luminescent Proximity Homogeneous)-based assays, scintillation proximity assays, ELISA (enzyme-linked immunosorbent assays), SPR (surface plasmon resonance, such as BIACORE®), isothermal titration calorimetry, differential scanning calorimetry, gel electrophoresis, analytical ultracentrifugation, and chromatography, including gel-filtration chromatography.

ii) Cell-Based Assays

Several in vitro, cell-based assays for testing the effector functions (e.g. FcR binding affinity) of altered polypeptides have been described in the art. Preferably, the cell-based assay is capable of evaluating binding of altered antibodies to surface forms of the Fc receptors. Exemplary cell-based assays include bridging assays and flow cytometry.

In an exemplary embodiment, the FcR binding affinity of an altered antibody can be measured using an FcR bridging assay. FcR (e.g. FcRn or FcγR) binding affinities can be measured with assays based on the ability of the antibody to form a "bridge" between antigen and a FcR bearing cell.

iii) Model Animal Assays

The altered polypeptides of the invention may also be administered to a model animal to test its potential for use in therapy, either for veterinary purposes or as an animal model of human disease, e.g., an immune disease or condition stated above, e.g., by testing the half-life or biodistribution of the antibody. Regarding the latter, such animal models may be useful for evaluating the therapeutic efficacy of antibodies of the invention (e.g., testing of effector function, dosages, and time courses of administration).

In one embodiment, altered polypeptides of the invention can be tested for improvements in circulating half-life. Altered polypeptides with enhanced half-life can, when administered to a model animal, are expected to remain within the circulation longer than a comparable polypeptide that does not contain the mutation (e.g., an antibody of the same type (e.g., an IgG such as IgG1) that does not contain a mutation at the position(s) where the altered antibody contains a mutation). For example, as 21 days is a typical beta phase half-life for a human antibody, the altered antibodies of the invention can be those that circulate longer than 21 days. In another embodiment, the altered polypeptide has a reduced half-life relative to the target antibody. For example, altered antibodies with a reduced half-life (e.g. less that 21 days) relative to a target antibody may be selected.

Examples of animal models which can be used for evaluating the therapeutic efficacy of altered polypeptides of the invention for preventing or treating tumor formation include tumor xenograft models.

Examples of animal models which can be used for evaluating the therapeutic efficacy of altered polypeptides of the invention for preventing or treating rheumatoid arthritis (RA) include adjuvant-induced RA, collagen-induced RA, and collagen mAb-induced RA (Holmdahl et al., *Immunol. Rev.* 184: 184, 2001; Holmdahl et al., *Ageing Res. Rev.* 1:135, 2002; Van den Berg, *Curr. Rheumatol. Rep.* 4:232, 2002).

Examples of animal models which can be used for evaluating the therapeutic efficacy of altered polypeptides of the invention for preventing or treating inflammatory bowel disease (IBD) include TNBS-induced IBD, DSS-induced IBD, and (Padol et al., *Eur. J. Gastrolenterol. Hepatol.* 12:257, 2000; Murthy et al., *Dig. Dis. Sci.* 38:1722, 1993).

Examples of animal models which can be used for evaluating the therapeutic efficacy of altered polypeptides of the invention for preventing or treating glomerulonephritis include anti-GBM-induced glomerulonephritis (Wada et al., *Kidney Int.* 49:761-767, 1996) and anti-thy1-induced glomerulonephritis (Schneider et al., *Kidney Int.* 56:135-144, 1999).

Examples of animal models which can be used for evaluating the therapeutic efficacy of antibodies or antigen-binding fragments of the invention for preventing or treating multiple sclerosis include experimental autoimmune encephalomyelitis (EAE) (Link and Xiao, *Immunol. Rev.* 184:117-128, 2001).

VII. FcRn Fusion Proteins

In another aspect, the invention provides novel reagents, e.g., for use in purification, for determining the binding affinity of an altered Fc-containing polypeptides of the invention, or for panning for additional Fc mutations that affect binding to FcRn.

The reagents of the invention are multimeric Fc binding proteins comprising a first polypeptide and at least one additional polypeptide wherein the first and additional polypeptides each comprise a least one Fc region or portion thereof operably linked to at least one monomeric Fc binding domain.

In one embodiment, the Fc regions or portion thereof and the Fc binding domain or portion thereof of each polypeptide is genetically fused using techniques that are readily available in the art. In certain embodiments, a multimer is formed by noncovalent bonding between the first and additional polypeptides. In another embodiment, multimer is formed by covalent bonding (e.g. disulfide bonding) between the first and additional polypeptides. Preferably, the first and second polypeptides are covalently bonded at their respective Fc regions (e.g. by disulfide bonds) to form a "dimeric" (or bidendate) Fc binding domain. In one embodiment, the Fc regions may be altered (e.g. mutated) so that their effector functions, particularly binding to Fc receptors, have been abrogated or inactivated. Said Fc regions and Fc binding domains may be derived from any organism that expresses the respective domains. Preferred species include human, monkey, mouse, rat, and rabbit. The mutimeric Fc receptors may be chimeric, for example, the Fc region may be derived from a rodent (e.g. a mouse or rat), while the Fc binding domain is derived from a primate (e.g. a human or monkey).

In certain preferred embodiments, the reagents may comprise an Fc binding domain derived from an Fc receptor (e.g. an Fc neonatal receptor) or the extracellular portion thereof. In one embodiment, an FcRn:Fc molecules of the invention is a dimeric molecules; each monomer making up the dimer comprising a first polypeptide comprising the extracellular domain of the alpha chain of a neonatal receptor (e.g. the $\alpha 1$ and $\alpha 2$ domains of the receptor) and an Fc region or portion thereof and a second beta-microglobulin ($\beta_2$m) polypeptide. In one embodiment, the Fc region is derived from IgG1. The DNA sequence of a preferred human FcRn alpha-Fc fusion is shown in SEQ ID NO:9 and the predicted amino acid sequence is shown in SEQ ID NO:10. The Fc region preferably contains at least one mutation which reduces its binding to a monomeric or multimeric Fc receptor. For example, mutations can be made at amino acid positions 310, 311, 433, and 434 (EU numbering), e.g., as described in Example 4.

Surprisingly, multimeric Fc receptors may be expressed at much higher levels than monomeric Fc receptors. For example, yields of up to 100 mg/L may be obtained following stable transfection of mammalian cell lines (e.g. CHO) with expression vectors that encode FcRn:Fc fusion proteins and $\beta_2$m, either together on the same vector or on separate vectors.

The reagents of the invention provide many advantages over existing reagents. The inventors have made the surprising and unexpected discovery that multimeric Fc receptors of the invention have greatly enhanced binding interaction with Fc-containing polypeptides Measurements of the binding affinities by Biacore for hFcRnFc to immobilized hIgG show a binding affinity of 25 nanomolar versus 2,000 nanomolar for monomeric hFcRn. For example, the reagents are capable of binding at least two separate FcR binding sites of an Fc-containing polypeptide (e.g. the Fc region of an antibody). In particular, the reagents of the invention are capable of binding FcR binding sites on both heavy chains of an Fc region of Fc polypeptide (e.g. an antibody). These properties impart enhanced binding interactions with Fc-containing polypeptides. In particular the reagents of the invention are capable of binding Fc-containing polypeptides with enhanced stability and/or avidity. Existing reagents typically comprise monomeric soluble Fc receptors or fragments thereof that suffer from a number of deficiencies. For example, monomeric Fc receptors, in particular human monomeric FcRn, cannot be used in many high-throughput screening (HTS) assay formats (e.g. HTS ELISAs) due to their poor affinity and instability when coated, labeled, or immobilized on solid (e.g. plastic) surfaces. Furthermore, binding of an Fc-polypeptide to a monomeric Fc receptor is relatively weak, making measurement of the binding signal difficult. In comparison to monomeric Fc receptor, the multimeric Fc receptors of the invention provide for a more robust assay due to their enhanced stability, and improved (e.g. >100-fold) binding affinity to a particular Fc-containing polypeptide.

Accordingly, the multimeric Fc receptors of the invention may be employed in a wide range of screening procedures to test alterations in the FcR binding affinity of any Fc-containing polypeptide. The mutimeric Fc receptors of the invention may be utilized in any cell-free binding assay known in the art that is capable of evaluating the binding of an Fc-containing polypeptide (e.g. an antibody) to the multimeric Fc receptor. Depending on the requirements of the assay, the mutimeric Fc receptors of the invention may be immobilized on a solid substrate or they may float free in solution. Suitable cell-free binding assays are recited herein. In one embodiment, the multimeric Fc receptors of the invention may be employed to test alterations in effector function of an altered polypeptide of the invention.

In another embodiment, the multimeric Fc receptors of the invention may be employed in the purification of Fc-containing polypeptides. For example, multimeric Fc receptors of the invention may be immobilized on a column, so that Fc-containing polypeptides may be purified from a mixture based on their greater affinity to the mutimeric Fc receptor. These methods provide certain advantages over existing affinity purification methods that require labelling the protein with tags that facilitate purification (e.g. with a H is or epitope tag). Such tags can interfere with the intended use of the purified protein (e.g. administration as a therapeutic) and, if removed, the methods for removing them require extensive repurification steps that result in extensive loss of product yield.

In an exemplary embodiment, a multimeric neonatal Fc receptor of the invention can facilitate binding of the Fc-containing polypeptide to the column at a first pH (e.g. an acidic pH) and elution from the column at a second pH (e.g. a neutral pH). Such a purification method provides additional advantages over existing methods for purification of Fc-containing polypeptides. For example, protein A affinity columns are commonly used for purification of antibodies and other Fc-containing polypeptides. However, elution of the polypeptide from the column requires relatively harsh treatments (e.g. low pH) that may destroy the polypeptide, resulting in extensive loss of product yield. In contrast, elution of an Fc-containing polypeptide from a multimeric neonatal Fc receptor affinity requires only a small rise from the first pH (e.g. pH5.8-6.5) to the second pH (e.g. pH 7.0-7.5).

In another embodiment, the multimeric Fc receptors (e.g. Furthermore, the reagents of the invention may be utilized for testing the safety of any Fc-containing protein based therapeutic, in particular monoclonal antibody therapeutics. For example, certain Fc-containing polypeptides (e.g. oxidized Fc-containing polypeptides), when administered to a patient, may exhibit undesirable transcytosis to a vulnerable tissue (e.g. placental transfer from a mother to a fetus). Such Fc-containing polypeptides are expected to bind a multimeric Fc receptor with lower affinity and will elute before unoxidized polypeptides. Methionine (e.g., EU position 253 and 429) residues are particularly vulnerable to oxidation. Therefore, an Fc polypeptide can be screened for binding to a multimeric Fc receptor and may be selected for therapeutic use if the binding affinity for a multimeric Fc receptor occurs at an acceptable threshold. For example, in one embodiment, binding to multimeric Fc receptors can be used to determine batch consistency or perform quality control tests among preparations of polypeptides.

The multimeric Fc receptors of the invention can be produced using any of the methods described herein.

VIII. Further Modification of Altered Fc-Containing Polypeptides

Altered Fc-containing polypeptide may be further modified to provide a desired effect. For example, in certain embodiments, the altered polypeptides may be modified (e.g. by chemical or genetic means) by conjugated (ie. physically linked) to an additional moiety to an additional moiety, i.e., a functional moiety such as, for example, a PEGylation moiety, a blocking moiety, a detectable moiety, a diagnostic moiety, and/or a therapeutic moiety, that serves to improve the desired function (e.g. therapeutic efficacy) of the polypeptide. Chemical conjugation may be performed by randomly or by site-specific modification of particular residues within the altered polypeptide. Exemplary functional moieties are first described below followed by useful chemistries for linking such functional moieties to different amino acid side chain chemistries of an altered polypeptide.

a) Functional Moieties

Examples of useful functional moieties include, but are not limited to, a PEGylation moiety, a blocking moiety, detectable moiety, a diagnostic moiety, and a therapeutic moiety.

Exemplary PEGylation moieties include moieties of polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA) and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic.

Preferably PEGylation moieties are attached to altered Fc-containing polypeptides of the invention that have enhanced-life. A PEGylation moiety can serve to further enhance the half-life of the altered polypeptide by increasing the molecule's apparent molecular weight. The increased apparent molecular weight reduces the rate of clearance from the body following subcutaneous or systemic administration. In many cases, a PEGylation also serve to decrease antigenicity and immunogenicity. In addition, PEGylation can increase the solubility of the altered polypeptide.

Exemplary blocking moieties include include cysteine adducts, cystine, mixed disulfide adducts, or other compounds of sufficient steric bulk and/or charge such that antigen-dependent effector function is reduced, for example, by inhibiting the ability of the Fc region to bind an Fc receptor or complement protein. Preferably, said blocking moieties are conjugated to altered polypeptides of the invention with reduced effector function such that effector function is further reduced.

Exemplary detectable moieties which may be useful for conjugation to the altered polypeptides of the invention include fluorescent moieties, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like). Other useful moieties are known in the art.

Examples of diagnostic moieties which may be useful for conjugation to the altered polypeptides of the invention include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties which may be useful for conjugation to the altered polypeptides of the invention include, for example, anti-inflammatory agents, anti-cancer agents, anti-neurodegenerative agents, and anti-infective agents. The functional moiety may also have one or more of the above-mentioned functions.

Exemplary therapeutics include radionuclides with high-energy ionizing radiation that are capable of causing multiple strand breaks in nuclear DNA, and therefore suitable for inducing cell death (e.g., of a cancer). Exemplary high-energy radionuclides include: $^{90}Y$, $^{125}I$, $^{131}I$, $^{123}I$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutics also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutics also include alkylating agents such as the anthracycline family of drugs (e.g. adriamycin, caminomycin, cyclosporin-A, chloroquine, methopterin, mithramycin, porfiromycin, streptonigrin, porfiromycin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum(II) dichloride (cisplatin), melphalan, mitoxantrone, and oxaliplatin.

Exemplary therapeutics also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone EO9, diaziridinyl-benzoquinone methyl DZQ, triethylenephosphoramide, and nitrosourea compounds (e.g. carmustine, lomustine, semustine).

Exemplary therapeutics also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (±)-thalidomide.

Exemplary therapeutics also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutics also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary therapeutics also include gene regulators such as 5-aza-2'-deoxycytidine, 5-azacytidine, cholecalciferol (vitamin $D_3$), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutics also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Other types of functional moieties are known in the art and can be readily used in the methods and compositions of the present invention based on the teachings contained herein.

b) Chemistries for Linking Functional Moieties to Amino Acid Side Chains

Chemistries for linking the foregoing functional moieties be they small molecules, nucleic acids, polymers, peptides, proteins, chemotherapeutics, or other types of molecules to particular amino acid side chains are known in the art (for a detailed review of specific linkers see, for example, Hermanson, G. T., *Bioconjugate Techniques*, Academic Press (1996)).

Exemplary art recognized linking groups for sulfhydryl moieties (e.g., cysteine, or thiol side chain chemistries) include, but are not limited to, activated acyl groups (e.g., alpha-haloacetates, chloroacetic acid, or chloroacetamide), activated alkyl groups, Michael acceptors such as maleimide or acrylic groups, groups which react with sulfhydryl moieties via redox reactions, and activated di-sulfide groups. The sulfhydryl moieties may also be linked by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

In a preferred embodiment, a cysteine or other amino acid with thiol side chain chemistry is linked during or subsequent to the production of an Fc containing polypeptide. For example, when producing the modified Fc containing polypeptide using cell culture, conditions are provided such that a free cysteine in solution can form a cysteine adduct with the thiol side chain of the Fc containing polypeptide. The so formed adduct may be used to inhibit glycosylation and/or effector function, or, subsequently subjected to reducing conditions to remove the adduct and thereby allow for the use of one of the aforementioned sulfhydryl chemistries.

Exemplary art recognized linking groups for hydroxyl moieties (e.g., serine, threonine, or tyrosine side chain chemistries) include those described above for sulfhydryl moieties including activated acyl groups, activated alkyl groups, and Michael acceptors.

Exemplary art recognized linking groups for amine moieties (e.g., asparagine or arginine side chain chemistries) include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, 3-carboxy-4-nitrophenyl, imidoesters (e.g., methyl picolinimidate), pyridoxal phosphate, pyridoxal, chloroborohydride, trinitrobenzenesulfonic acid, O-methyliosurea, and 2,4-pentanedione.

Exemplary art recognized linking groups for acidic moieties (e.g., aspartic acid or glutamic side chain chemistries) include activated esters and activated carbonyls. Acidic moieties can also be selectively modified by reaction with carbodiimides (R'N—C—N—R') such as 1-cyclohexyl-3-[2-morpholinyl-(4-ethyl)]carbodiimide or 1-ethyl-3-(4-azonia-4,4-dimethylpentyl)carbodiimide.

Where the functional moiety desired is a PEGylation moiety, PEGylation reactions which are well known in the art may be employed. For example, in one method, the PEGylation is carried out via an acylation reaction or an alkylation reaction with a reactive polyethylene glycol molecule (or an analogous reactive water-soluble polymer). A water-soluble polymer for pegylation of the antibodies and antibody fragments of the invention is polyethylene glycol (PEG). In another embodiment, the polymer for pegylation is polyethylene glycol-maleimide (i.e., PEG-maleimide).

Methods for preparing pegylated antibodies and antibody fragments of the invention will generally comprise the steps of a) reacting the antibody or antibody fragment with polyethylene glycol, such as a reactive ester or aldehyde derivative of PEG, under conditions whereby the antibody or antibody fragment becomes attached to one or more PEG groups, and b) obtaining the reaction products. It will be apparent to one of ordinary skill in the art to select the optimal reaction conditions or the acylation reactions based on known parameters and the desired result. In one embodiment, a particular amino acid reside can be targeted, for example, the first amino acid residue altered in order to inhibit glycosylation of a second amino acid residue, and preferably where the first amino acid is a cysteine or has a thiol chemistry.

IX. Prophylactic, Diagnostic, and Therapeutic Methods

The present invention has general utility when the altered polypeptide (e.g., an antibody or fusion protein) binds a cell-surface antigen, where the binding provokes a required effector response. One example of an effector-mediated response is the reduction in the root cause of a disorder (e.g., elimination of tumor cells or of antigen-bearing cells that are involved in immune or inflammatory responses). In another embodiment, one or more symptom(s) of a disorder can be reduced. In another embodiment, the compositions described herein can be used to alter an effector-mediated response in a diagnostic reagent (e.g., an antibody used for imaging tumors). The methods described herein can be used to treat a subject at risk of developing a disorder or a subject currently exhibiting symptoms of a disorder.

A. Anti-Tumor Therapy

Accordingly, in certain embodiments, the altered polypeptides of the present invention are useful in the prevention or treatment of cancer. In one embodiment, an altered polypeptide blocks autocrine or paracrine growth (e.g., by binding to a receptor without transducing a signal, or by binding to a growth factor). In preferred embodiments, the altered polypeptide is capable of binding to a tumor-associated antigen.

In one embodiment, the altered polypeptides may reduce tumor size, inhibit tumor growth and/or prolong the survival time of tumor-bearing animals. In general, the disclosed invention may be used to prophylactically or therapeutically treat any neoplasm comprising an antigenic marker that allows for the targeting of the cancerous cells by the modified antibody. Exemplary cancers or neoplasias that may be prevented or treated include, but are not limited to bladder cancer, breast cancer, head and neck cancer, prostate cancer, colo-rectal cancer, melanoma or skin cancer, breast cancer, ovarian cancer, cervical cancer, endometrial cancer, kidney cancer, lung cancer (e.g. small cell and non-squamos cell cancers), pancreatic cancer, and multiple myeloma. More particularly, the modified antibodies of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate starting polypeptides may be derived for tumor associated antigens related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the altered polypeptides and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

B. Immune Disorder Therapies

Besides neoplastic disorders, the altered polypeptides of the instant invention are particularly effective in the treatment of autoimmune disorders or abnormal immune responses. In this regard, it will be appreciated that the altered polypeptide of the present invention may be used to control, suppress, modulate or eliminate unwanted immune responses to both external antigens and autoantigens. For example, in one embodiment, the antigen is an autoantigen. In another embodiment, the antigen is an allergan. In yet other embodiments, the antigen is an alloantigen or xenoantigen. Use of the disclosed modified polypeptides to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the altered polypeptides of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic demiatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cirrhosis; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-trans-plantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; lupus nephritis; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polyrnyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Scleroderma, Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

C Anti-inflammatory Therapy

In yet other embodiments, the altered polypeptides of the present invention may be used to treat inflammatory disorders that are caused, at least in part, or exacerbated by inflammation, e.g., increased blood flow, edema, activation of immune cells (e.g., proliferation, cytokine production, or enhanced phagocytosis). Exemplary inflammatory disorders include those in which inflammation or inflammatory factors (e.g., matrix metalloproteinases (MNIPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in a given area or tissue in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, Alzheimer's; severe asthma, atherosclerosis, cachexia, CHF-ischemia, and coronary restenosis; osteoarthritis, rheumatoid arthritis, fibrosis/radiation-induced or juvenile arthritis; acute and chronic infections (bacterial, viral and fungal); acute and chronic bronchitis, sinusitis, and other respiratory infections, including the common cold; acute and chronic gastroenteritis and colitis and Crohn's disease; acute and chronic cystitis and urethritis; acute respiratory distress syndrome; cystic fibrosis; acute and chronic dermatitis; psoriasis; acute and chronic conjunctivitis; acute and chronic serositis (pericarditis, peritonitis, synovitis, pleuritis and tendinitis); uremic pericarditis; acute and chronic cholecystis; acute and chronic vaginitis; stroke, inflammation of the brain or central nervous system caused by trauma, and ulcerative colitis; acute and chronic uveitis; drug reactions; diabetic nephropathy, and burns (thermal, chemical, and electrical). Other inflammatory disorders or conditions that can be prevented or treated with the antibodies or antigen-binding fragments of the invention include inflammation due to corneal transplantation, chronic obstructive pulmonary disease, hepatitis C, lymphoma, multiple myeloma, and osteoarthritis.

In another embodiment, the polypeptides of the invention can be used to prevent or treat neurodegenerative disorders, including, but not limited to Alzheimer's, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease. In preferred embodiments, altered polypeptides having reduced binding affinity to FcRn are used to treat nervous system disorders, as they do not cross the blood brain barrier as efficiently as those with higher FcRn binding affinity. For example, in one embodiment, an altered polypeptide of the invention is injected into the spinal fluid to treat a neurodegenerative disorder.

In prophylactic applications, pharmaceutical compositions comprising a polypeptide of the invention or medicaments are administered to a subject at risk for (or having and not yet exhibiting symptoms of) a disorder treatable with a polypeptide having an Fc region, for example, an immune system disorder, in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder.

In therapeutic applications, compositions or medicaments are administered to a subject already suffering from such a disorder in an amount sufficient to cure, or at least partially arrest, the symptoms of the disorder (biochemical, histologic and/or behavioral), including its complications and intermediate pathological phenotypes in development of the disorder. The polypeptides of the invention are particularly useful for modulating the biological activity of a cell surface antigen that resides in the blood, where the disease being treated or prevented is caused at least in part by abnormally high or low biological activity of the antigen.

In some methods, administration of agent reduces or eliminates the immune disorder, for example, inflammation. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved.

It will be understood that the modified polypeptides of the invention can be used to treat a number of disorders not explicitly mentioned herein based on selection of the target molecule to which the polypeptide binds. It will be further recognized that any art recognized antibody or fusion protein may be modified according to the methods of the invention and used to treat a disorder for which it is indicated.

D. Methods of Administration

Altered polypeptides of the invention can be administered by startingeral, topical, intravenous, oral, intraarterial, intracranial, intraperitoneal, or intranasal means for prophylactic and/or therapeutic treatment. The term startingeral as used herein includes intravenous, intraarterial, intraperitoneal, intramuscular, subcutaneous, rectal or vaginal administration. The most typical route of administration of a protein drug is intravascular, subcutaneous, or intramuscular, although other routes can be effective. In some methods, agents are injected directly into a particular tissue where deposits have accumulated, for example intracranial injection. In some methods, antibodies are administered as a sustained release composition or device, such as a Medipad™ device. The protein drug can also be administered via the respiratory tract, e.g., using a dry powder inhalation device.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

For passive immunization with an antibody, the dosage ranges from about 0.0001 to 100 mg/kg, and more usually 0.01 to 20 mg/kg, of the host body weight. For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two polypeptides with different binding specificities are administered simultaneously, in which case the dosage of each polypeptide administered falls within the ranges indicated.

Polypeptides are usually administered on multiple occasions. Intervals between single dosages can be weekly, monthly or yearly. In some methods, dosage is adjusted to achieve a plasma antibody concentration of 1-1000 µg/ml and in some methods 25-300 µg/ml. Alternatively, polypeptides can be administered as a sustained release formulation, in which case less-frequent administration is required. Dosage and frequency vary depending on the half-life of the polypeptide in the subject. In general, human antibodies show the longest half-life, followed by humanized antibodies, chimeric antibodies, and nonhuman antibodies. As discussed herein, the half-life also depends upon the particular mutation(s) present in the altered polypeptide.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the subject shows partial or complete amelioration of symptoms of disease. Thereafter, the patent can be administered a prophylactic regime.

Doses for nucleic acids encoding antibodies range from about 10 ng to 1 g, 100 ng to 100 mg, 1 µg to 10 mg, or 30-300 µg DNA per subject. Doses for infectious viral vectors vary from 10-100, or more, virions per dose.

One skilled in the art would be able, by routine experimentation, to determine what an effective, non-toxic amount of altered polypeptide would be for the purpose of treating a disorder. For example, a therapeutically active amount of a modified polypeptide may vary according to factors such as the disease stage (e.g., stage I versus stage IV tumor), age, sex, medical complications (e.g., immunosuppressed conditions or diseases) and weight of the subject, and the ability of the modified polypeptide to elicit a desired response in the subject. The dosage regimen may be adjusted to provide the optimum therapeutic response. For example, several divided doses may be administered daily, or the dose may be proportionally reduced as indicated by the exigencies of the therapeutic situation.

E. Monitoring of Treatment

Treatment of a subject suffering from a disease or disorder can be monitored using standard methods. Some methods entail determining a baseline value, for example, of an antibody level or profile in a subject, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a subject after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a subject are compared with the control value. If the measured level in a subject is not significantly different (e.g., more than one standard deviation) from the control value, treatment can be discontinued. If the level in a subject is significantly below the control value, continued administration of agent is warranted. If the level in the subject persists below the control value, then a change in treatment may be indicated.

In other methods, a subject who is not presently receiving treatment but has undergone a previous course of treatment is monitored for polypeptide levels or profiles to determine whether a resumption of treatment is required. The measured level or profile in the subject can be compared with a value previously achieved in the subject after a previous course of treatment. A significant decrease relative to the previous measurement (i.e., greater than a typical margin of error in repeat measurements of the same sample) is an indication that treatment can be resumed. Alternatively, the value measured in a subject can be compared with a control value (mean plus standard deviation) determined in a population of subjects after undergoing a course of treatment. Alternatively, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level (i.e., more than a standard deviation) is an indicator that treatment should be resumed in a subject.

The polypeptide profile following administration typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of polypeptide to a given antigen in the subject is made before administration, a second measurement is made soon thereafter to determine the peak polypeptide level, and one or more further measurements are made at intervals to monitor decay of polypeptide levels. When the level of polypeptide has declined to baseline or a predetermined percentage of the peak less baseline (e.g., 50%, 25% or 10%), administration of a further dosage of polypeptide is administered. In some methods, peak or subsequent measured levels less background are compared with reference levels previously determined to constitute a beneficial prophylactic or therapeutic treatment regime in other subjects. If the measured polypeptide level is significantly less than a reference level (e.g., less than the mean minus one standard deviation of the reference value in population of subjects benefiting from treatment) administration of an additional dosage of polypeptide is indicated.

Additional methods include monitoring, over the course of treatment, any art-recognized physiologic symptom (e.g., physical or mental symptom) routinely relied on by researchers or physicians to diagnose or monitor disorders.

F. Combination Therapy

Altered polypeptides of the invention can optionally be administered in combination with other agents (including any agent from Section VIE supra) that are known or determined to be effective in treating the disorder or condition in need of treatment (e.g., prophylactic or therapeutic). In addition, the polypeptides of the invention can be conjugated to a moiety that adds functionality to the polyeptide, e.g., (e.g., PEG, a tag, a drug, or a label).

It will further be appreciated that the altered polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. Exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas, in* HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more modified polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), Pro-MACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, carboplatin, cisplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the modified polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9*th* ed. 1996).

While the modified polypeptides may be administered as described herein, it must be emphasized that in other embodiments modified polypeptides may be administered to otherwise healthy patients as a first line therapy. In such embodiments the modified polypeptides may be administered to patients having normal or average red marrow reserves and/or to patients that have not, and are not, undergoing. As used herein, the administration of modified polypeptides in conjunction or combination with an adjunct therapy means the sequential, simultaneous, coextensive, concurrent, concomitant or contemporaneous administration or application of the therapy and the disclosed antibodies. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated modified polypeptides could be administered intravenously followed by tumor localized external beam radiation. In yet other embodiments, the modified polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the modified polypeptide and the chemotherapeutic agent may be administered in any order and within any time frame that provides a therapeutic benefit to the patient. That is, the chemotherapeutic agent and modified polypeptide may be administered in any order or concurrently. In selected embodiments the modified polypeptides of the present invention will be administered to patients that have previously undergone chemotherapy. In yet other embodiments, the modified polypeptides and the chemotherapeutic treatment will be administered substantially simultaneously or concurrently. For example, the patient may be given the modified antibody while undergoing a course of chemotherapy. In preferred embodiments the modified antibody will be administered within 1 year of any chemotherapeutic agent or treatment. In other preferred embodiments the modified polypeptide will be administered within 10, 8, 6, 4, or 2 months of any chemotherapeutic agent or treatment. In still other preferred embodiments the modified polypeptide will be administered within 4, 3, 2 or 1 week of any chemotherapeutic agent or treatment. In yet other embodiments the modified polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

IX. Pharmaceutical Compositions

The therapeutic compositions of the invention include at least one of the modified Fc-containing polypeptides produced by a method described herein in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Polypeptides can be administered in the form of a depot injection or implant preparation, which can be formulated in such a manner as to permit a sustained release of the active ingredient. An exemplary composition comprises polypeptide at 5 mg/mL, formulated in aqueous buffer consisting of 50 mM L-histidine, 150 mM NaCl, adjusted to pH 6.0 with HCl. An exemplary generic formulation buffer is 20 mM sodium citrate, pH 6.0, 10% sucrose, 0.1% Tween 80.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249:1527, 1990 and Hanes, *Advanced Drug Delivery Reviews* 28:97, 1997).

This invention is further illustrated by the following examples which should not be construed as limiting. The contents of all references, patents, and published patent applications cited throughout this application, as well as the figures and the sequence listing, are hereby incorporated by reference.

EXAMPLES

Example I

Production of Altered Antibodies with Chimeric Fc Regions

To evaluate the binding of human rabbit IgG chimera constructs, the amino acids likely to impact binding were first defined as being within 10 Å of the interface of interaction between the two interacting proteins. Based on the crystal structure of the ratIgG2a and rat FcRn, the amino acids on the ratIgG2a Fc within 10 Å of the interface for these two molecules was defined. A homology alignment of rabbit IgG1 Fc and the rat IgG1 Fc regions then allows determination of which amino acids on the rabbit Fc region are likely to be within 10 Å of the interaction face. Correspondence of the rat and human Fc regions is then determined. A chimeric molecule is then constructed including all of the mutants within the 10 Å interface. The individual amino acids are then substituted into the hFc and assayed to determine the contribution of the individual component amino acids to binding. Combinations of the amino acid mutants are then constructed with those molecules that show enhanced binding to hFcRn. In this way only the positive contributors to the binding are identified.

The affinity of each mutant is assayed using the biacore with molecules showing a 25% or better enhancement in affinity being scored as a positive result. Assays are carried out at pH 6.

The mutant antibodies are expressed transiently in 293 cells by standard techniques to those of ordinary skill in the art. The expressed proteins contain a human F(ab) that is lambda for, and can be purified readily with, protein L. The antibody is reactive with an epitope not expressed in the animal in which the pK will be deter mined. The detection of the mAb in the blood is done by ELISA using the antigen to which the variable domains are reactive and detection with an anti-human H&L HRP (horseradish peroxidase) secondary antibody. These assays and animal models are easily established by one of ordinary skill in the art.

Kd of rabbit IgG1 to soluble monomeric hFcRn has been measured on the Biacore. The value was compared on the same chip to Kd determined for human IgG1. In these experiments, IgGs are immobilized on different quadrants of the chip and direct comparison of the Kd values can be determined. The proteins were purchased and validated for purity prior to use by SDS PAGE and analytical gel filtration.

Sequence alignments of the rabbit IgG1 and a human IgG1 were completed and the sequences within 10 Å of the interface between human and rabbit IgG, as determined from ratIgG2a/rFcRn crystal structure have been identified.

Specific amino acid substitutions within the IgG constant domain of human antibodies and IgG fusion proteins that increase the half-life of antibodies are determined. The claimed mutations are specifically derived from chimeric protein constructs between a rabbit IgG1 constant domain (rFc) and hIgG1 constant domain (hFc).

The affect of the changes are then determined by measuring the binding affinity of the hFcRn to the mutated hFc regions in comparison to the native hFc the h/rFc chimera show greater affinity for the hFcRn. In vivo half-life of the molecules are then determined in a monkey or other appropriate model such as a knock-in or transgeneic hFcRn mouse to show that the chimeric protein has enhanced half-life compared to the native hFc.

Results: Biacore data with hFcRn showing a Kd value two fold tighter for rabbit IgG binding to hFcRn then hIgG has been obtained. Exemplary residues for substitution include: EU positions 280, 281, 282, 283, 285, 286, 288, 289, 290, 305, 307, 308, 309, 315, 340, 344, and 378. More specifically, a polypeptide of the invention may contain at least one amino acid mutations selected from the group consisting of: Asp280Asn (where D indicates amino acid position to be mutated (by substitution) at the recited EU position (278) and where N indicates the amino acid to be substituted into that position to arrive at the altered polypeptide), Gly281Glu, Val282Glu, Glu283Gln, His285Arg, Asn286Thr, Lys288Arg, Thr289Pro, Lys290Pro, Val305Thr, Thr307Pro, Val30811e, Leu309Thr, Asn3153Arg, Lys340Arg, Arg344Leu, Ala378Ser, Ser383Lys, Glu386Lys, Pro387Ala, and Asn389Asp, according to the EU numbering system.

Example 2

Identification of Candidate Residues by Electrostatic Optimization

In this example, method for modifying the antibody constant domain affinity towards human FcRn is described. To obtain mutants with altered binding affinity of an Fc region to FcRn at acidic pH and neutral pH, we applied electrostatic charge optimization techniques to a homology model of human Fc bound to human FcRn. The models of human Fc/FcRn complex at acidic (6.0) pH and neutral (7.4) pH were derived from a crystal structure of rat Fc/FcRn complex (PDB code: 1I1A) using MODELLER program, (Accelrys, Inc., San Diego, Calif.) and were energy-minimized in CHARMM (Accelrys, Inc., San Diego, Calif.). In a computational optimization procedure, we used electrostatic charge optimization to determine the position(s) of the Fc residue(s) that can modulate Fc binding (Lee and Tidor, *J. Chem. Phys.* 106: 8681-8690, 1997; Kangas and Tidor, *J. Chem. Phys.* 109: 7522-7545, 1998) to FcRn at acidic pH and neutral pH. These calculations were completed at two pH values, acidic (6.0) pH and neutral pH (7.4), because the Fc is known to bind the FcRn at acidic pH in the pinocytotic vacuole and released in extracellular space at neutral pH. Enhanced binding of the Fc to FcRn at neutral pH may well be detrimental to Fc half-life. A decrease in half-life would be the expected result if the IgG is unable to release from the cell bound FcRn during the typical IgG scavenging mechanism. Therefore Fc containing proteins that have enhanced affinity to FcRn at the higher pH would be removed from the blood, resulting in a protein with a shorter half-life.

The mutation predictions can be categorized as involving (1) mutations at the interaction interface involving residues that become partially buried upon binding (interactions are improved by making hydrogen bonds across the interface); (2) mutations of polar residues on the antibody that become buried upon binding and thus pay a desolvation penalty but do not make any direct electrostatic interactions with the FcRn (improvements are usually made by mutation to a hydrophobic residue with similar shape to the wild-type residue or by adding a residue that can make favorable electrostatic interactions); and (3) mutations of surface residues on the Fc that are in regions of uncomplementary potentials. These mutations are believed to improve long-range electrostatic interactions between the Fc and FcRn without perturbing packing interactions at the binding interface and include both mutations that preserve and alter the charge of the molecules.

Charge optimizations are performed with various constraints imposed to represent natural side chain characteristics. For example, an optimization was performed for a net side chain charge of −1, 0, and +1 with the additional constraint that no atom's charge exceeded an absolute value of 0.85 electron charge units The model was prepared using standard procedures for adding hydrogens with the program CHARMM (Accelrys, Inc., San Diego, Calif.). N-acetamide and N-methylamide patches were applied to the N termini and C-termini, respectively, except for N-terminus of β2-microglobulin chain. Models for acidic pH and neutral pH values were prepared separately to account for different protonation and rotameric states of histidine residues and rotameric states of asparagines and glutamines. Using a continuum electrostatics model, we performed an electrostatic charge optimization on each side chain of the amino acids in the Fc that is within 15 Å of the FcRn (candidate residues) interface at acidic pH and neutral pH values. Based on results from a charge optimization, mutations were determined for additional computational analysis. In this process we visually inspected the optimal charge distributions and design mutations that are closer to optimal than the current residue. A charge optimization gives charges at atom centers but does not yield actual mutation. A round of charge optimizations was performed with various constraints imposed to represent natural side chain characteristics. For example, an optimization was performed for a net side chain charge of −1, 0, and +1 with the additional constraint that no atom's charge exceeded an absolute value of 0.85 electron charge units. Only position, substitutions at which ideal charge distributions can generate no less than 0.3 kcal/mole of binding difference to human FcRn between neutral pH and acidic pHs were selected. Ideal charge distribution on the existing side chains was analyzed and substitutes from a set on 20 natural amino acids were suggested.

The following example shows the optimization results obtained for valine 284, histidine 285, asparagine 286, and lysine 290 (which are examples of elected residues) of the Fc molecule. The Mut (Mutation energy) column corresponds to the binding free energy difference (in kcal/mol) in going from the native residue to a completely uncharged sidechain isostere, i.e., a residue with the same shape but no charges or partial charges on the atoms. Negative numbers indicate a predicted increase of binding affinity. The Opt-1 column corresponds to the binding free energy difference that can be obtained with an optimal charge distribution in the side chain and a net side chain charge of −1. The columns Opt0 and Opt1 correspond to the binding free energy differences with optimal charges, the net charge being 0 and +1, respectively.

For acidic pH the following results were obtained:

| Residue | Mut  | Opt-1 | Opt0 | Opt1 |
|---------|------|-------|------|------|
| V284    | 0.0  | −0.9  | −0.3 | 0.5  |
| H285    | −0.6 | −2.0  | −1.6 | −1.1 |
| N286    | 0.0  | −1.1  | −0.2 | 1.1  |
| K290    | −0.7 | −0.8  | −0.9 | −0.8 |

For neutral pH the following results were obtained:

| Residue | Mut  | Opt-1 | Opt0 | Opt1 |
|---------|------|-------|------|------|
| V284    | 0.0  | −0.2  | −0.3 | −0.3 |
| H285    | 0.1  | −0.2  | −0.1 | 0.2  |
| N286    | 0.1  | −0.3  | −0.3 | −0.3 |
| K290    | −0.2 | 0.1   | −0.3 | −0.3 |

Based on these results and visual analysis of the models changes to glutamates that could take advantage of these binding free energy improvements were suggested. Indeed, for all the positions a ΔΔG greater than 0.3 kcal/mol of binding difference to human FcRn between neutral pH and acidic pH can be obtained by mutating a wild type amino acid to glutamate.

The mutant sidechains were built by performing a rotamer dihedral scan in CHARMM, using dihedral angle increments of 30 or 60 degrees, to determine the most desirable position for each sidechain. Binding energies were then calculated for the wild type and mutant complexes using the Poisson-Boltzmann electrostatic energy and additional terms for the van der Waals energy and buried surface area. Calculations were performed at acidic pH and neutral pH with PARSE or CHARMM charge sets for amino acids. Consensus scoring scheme was used, meaning that results obtained using both charge sets should agree in sign to generate a meaningful prediction.

The following example demonstrates the use of this method for valine 284, histidine 285, asparagine 286, and lysine 288 of the Fc molecule:

| Residue | Number | Mutant | $\Delta\Delta G_{6.0\ parse}$ | $\Delta\Delta G_{7.4\ parse}$ | $\Delta\Delta G_{6.0\ charmm}$ | $\Delta\Delta G_{7.4\ charmm}$ |
|---|---|---|---|---|---|---|
| V | 284 | E | −1.7 | 0.7  | −1.4 | −0.3 |
| H | 285 | E | −2.5 | 0.4  | −2.3 | −1.2 |
| N | 286 | E | −0.4 | 1.2  | −1.5 | −0.7 |
| K | 290 | E | −0.9 | −0.4 | −1.8 | 0.7  |

At acidic pH the ΔΔG for the binding of human Fc to human FcRn relative to wild-type Fc to FcRn binding is lower than −0.3 kcal/mol for both charge sets indicating the increase in affinity relative to wild-type human Fc. At neutral pH ΔΔG are of different sign for the charge sets indicating that it is unlikely (in context of the consensus scoring scheme) that the mutants will have the higher binding affinity, to human FcRn at neutral pH relative to wild-type human Fc. Therefore, V284E, H285E, N286E, and K290E mutants (which are examples of selected mutants) are predicted to have longer FcRn-mediated half-life than a wild type molecule in an organism.

In conclusion, we have implemented the computational process described above to predict mutations that modulate FcRn binding affinity of Fc molecule differently at neutral and acidic pH values. We suggest that amino acid substitutions in human Fc that have increase in FcRn affinity at acidic pH without affecting, or decreasing the affinity of the interaction at neutral pH will result in Fc molecules that have a longer in vivo half-life. Amino acid substitutions that yield enhanced Fc/FcRn binding at neutral pH and/or diminished Fc/FcRn binding at acidic pH will demonstrate a decrease in vivo half-life.

Example 4

Construction of Altered Fc Polypeptides

Alterations predicted by the methods of the invention were introduced into a starting polypeptide encoding the heavy chain of humanized IgG1 monoclonal antibody huCBE11. FIGS. 1A and 1B display the nucleotide (SEQ ID NO. 3) and predicted amino acid sequence (SEQ ID NO. 4) of this heavy chain respectively. Mutations were introduced in the huCBE11 heavy chain carried on an expression vector called pEAG1787 using site-directed mutagenesis by standard recombinant DNA techniques. The variable domain of the antibody is residues 1-120, the human IgG1 constant domain is residues 121-449. The huIgG1's C-terminal lysine residue was genetically removed. For reference: the N-linked glycosylation site (EU residue number N297) is residue 300 in the sequence above. FIG. 2 displays the amino acids sequence of the Fc region of huCBE11 in EU numbering index.

The huCBE11 monoclonal antibody is a humanized IgG1, kappa recombinant antibody that recognizes the human lymphotoxin beta receptor. The mAb CBE11 cloning, chimerization, and humanization is described in US patent application 2004/0058394. The huCBE11 light chain was carried in an expression vector called pEAG1754. The variable domain is residues 1-107, the human kappa constant domain is residues 108-214. FIGS. 3A and 3B display the nucleotide (SEQ ID NO. 5) and predicted amino acid sequence (SEQ ID NO. 6) of this light chain respectively.

Wild-type and altered antibodies were expressed by transient co-transfection of a human embryonic kidney cell line (HEK293E) with the heavy chain vector (pEAGI787) and the light chain vector (pEAGI 754).

Example 5

Construction of an FcRn—Fc Fusion Protein Reagent

A dimeric Fc binding protein was constructed by genetically fusing the extracellular domain of a neonatal Fc receptor with the Fc region of an IgG1 antibody.

Briefly, human beta-2-microglobulin cDNA was cloned by RT-PCR from human placental polyA+ RNA. The nucleotide sequence (SEQ ID NO. 7) and predicted amino acid sequence (SEQ ID NO:8) of human beta-2-microglobulin cDNA is shown in FIGS. 4A and 4B respectively. cDNA corresponding to the α-chain of human FcRn was cloned by RT-PCR from human placental polyA+ RNA and sequenced. The extracellular domain (ECD) of the human FcRn α-chain (residues 1-297) was subcloned for fusion to a human Fc region derived from an IgG1 antibody.

An Fc region (residues 398-535) was derived from a previously described human IgG1 antibody (see U.S. Pat. No. 5,928,643). The IgG1 Fc region contained a truncated hinge but retained the CH2 and CH3 domains of the antibody, except that the C-terminal lysine residue of the CH3 domain was genetically removed. The nucleotide sequence (SEQ ID NO. 3) and predicted amino acid sequence (SEQ ID NO. 4) of the heavy chain of the IgG1 antibody cDNA is shown in FIGS. 1A and 1B.

To eliminate the likelihood of the fusion protein binding to FcRns, the Fc region was mutated by site-directed mutagenesis from its wild type sequence at four positions, shown at residues 388, 389, 511, and 512 underlined in the sequence shown FIG. 5B, to make the human equivalent ("huM4Fc") of the H310A/Q311N/H433A/N434Q mutant (EU numbering) previously demonstrated to significantly reduce FcRn binding affinity to FcRn and serum half-life (Kim et al., 1994, Eur. J. Immunol. 24:542-548; and Popov et al., 1996, Mol. Immunol. 33: 521-530).

The Fc region was fused to the C-terminus of the FcRn ECD using standard recombinant DNA techniques to form an FcRn—Fc fusion protein cDNA. The beta-2-microglobulin and FcRn—Fc fusion protein cDNAs were inserted in an expression vector (pEAG1761) which carries both cDNAs in tandem transcription units driven by the cytomegalovirus immediate early promoter. pEAG1761 was transfected into CHO cells to produce a stable cell line secreting a soluble dimer (heterotetrameric FcRn—Fc fusion protein consisting of two beta-2-microglobulin and two FcRn alpha-Fc fusion chains). The nucleotide sequence (SEQ ID NO. 9) and predicted amino acid sequence (SEQ ID NO. 10) of the human FcRn alpha-Fc fusion cDNA encoded by pEAG1761 are shown in FIGS. 5A and 5B respectively.

Conditioned medium (from CHO or 293E cells) containing secreted FcRn-huM4Fc (α-chain and β2 microglobulin) fusion protein was concentrated approximately 6-fold to 150 ml in an Amicon stirred cell unit using a 10,000 MWCO polyethersulfone membrane. The concentrated material was dialyzed overnight against 40 volumes of 20 mM MES (pH 5.8), 150 mM NaCl and subsequently centrifuged at 2060×g for 10 minutes at 4° C. to pellet cell debris. The applied to a 6 ml human IgG-Sepharose 6 Fast Flow (Amersham Biosciences) column pre-equilibrated in 20 mM MES (pH 5.8), 150 mM NaCl. Bound FcRnFc was eluted with a single step change of buffer pH 8 in 20 mM Tris, 150 mM NaCl. The hIgG-Sepharose column has been successfully used to capture rat, mouse and human FcRn-huM4Fc proteins.

Eluted fractions were analyzed by non-reducing SDS-PAGE (4%-20% gradient gels) and FcRn-huM4Fc containing fractions were pooled for further purification by anion exchange chromatography. Protein concentration was determined spectrophotometrically by using $A_{280}$ values of 1.80 for a 1 mg/ml solution of the human or rat protein, and 1.84 for the mouse protein. Approximately 70 mg of hFcRn-M4Fc was eluted from the IgG-Sepharose column. This pool was dialyzed against 20 mM Tris pH8 prior to being loaded on a 5 ml DEAE column. Bound protein was eluted from the DEAE column using a linear gradient (20 column volumes) of increasing salt up to a final concentration of 0.5M NaCl. FcRn-huM4Fc proteins eluted at approximately 150 mM-175 mM NaCl (30%-35% 0.5M NaCl Buffer). DEAE fractions were analyzed for purity by SDS-PAGE as above and FcRn-huM4Fc containing fractions were pooled to yield a 48 mg homogenous pool of FcRnFc.

The DEAE pools were concentrated and buffer exchanged by centrifugation through Vivaspin concentrator units (10, 000 MWCO) into 20 mM MES (pH 5.8), 150 mM NaCl buffer for storage at −80° C., or for size exclusion chromatography (Superdex200 16/60, Amersham Biosciences) as a final purification step to remove a small amount of aggregates.

Example 6

Assaying FcRn Binding Affinity of Altered Polypeptides

Altered human monoclonal antibodies of the invention were characterized by their ability to bind biotinylated FcRn using a variety of cell-free assays.

a) Purification of Altered Fc Polypeptides

Human monoclonal antibodies containing altered Fc regions were purified using the FcRn-huM4Fc fusion protein of Example 4. To facilitate purification, FcRn-huM4Fc fusion protein was immobilized on Sepharose 4 Fast Flow Media. A 2 ml hFcRnFc column was prepared by coupling approximately 20 mg of hFcRn to NHS-activated Sepharose 4 Fast Flow media (Amersham Biosciences) in PBS (pH 7.2) with rocking at 4° C. overnight. The column was washed with PBS prior to use for purification. 1 mg of each human FcRnFc column.

1 mg each of an altered human IgG1 mAb was applied to the column in loading buffer, 20 mM MES (pH 5.8), 150 mM NaCl. The column was then washed with 10 column volumes of the loading buffer and the bound mAbs were eluted with a pH step gradient raising the pH to 8.0 (20 mM Tris, 150 mM NaCl).

b) Biotinylation of FcRn-huM4Fc (bhFcRnFc):

BiotinXXsulfosuccinimidyl ester (XX=two aminohexanoyl chains) was used to biotinylate FcRn-huM4Fc for use in competitive, bead-based, FRET and AlphaScreen assays described below. The reagent is available in the Mini-Biotin-XX protein labeling kit F6347 from Molecular Probes. FcRnFC was dialyzed in PBS150 mM Na/K phosphate, pH 7.0 and 150 mM NaCl. To 0.72 mg/ml of hFcRnFcIgG (500 ul) was added a $1/10^{th}$ volume of the 1M Na bicarbonate (50 uL) carbonate (NaHCO$_3$) stock solution. Next was added 10 ul of biotin-XX reagent, dissolved in water immediately prior to use as described by Molecular Probes. The reaction was incubated 1 h at room temperature and then exhaustively dialyzed at 4° C. versus PBS. The biotinylated fusion protein (bhFcRnFc) was stable when frozen at −80° C.

c) Direct Binding Assays:

The direct binding of unlabelled hFcRn—Fc to the altered Fc polypeptides of the invention was evaluated using an ELISA format.

Figure 10:
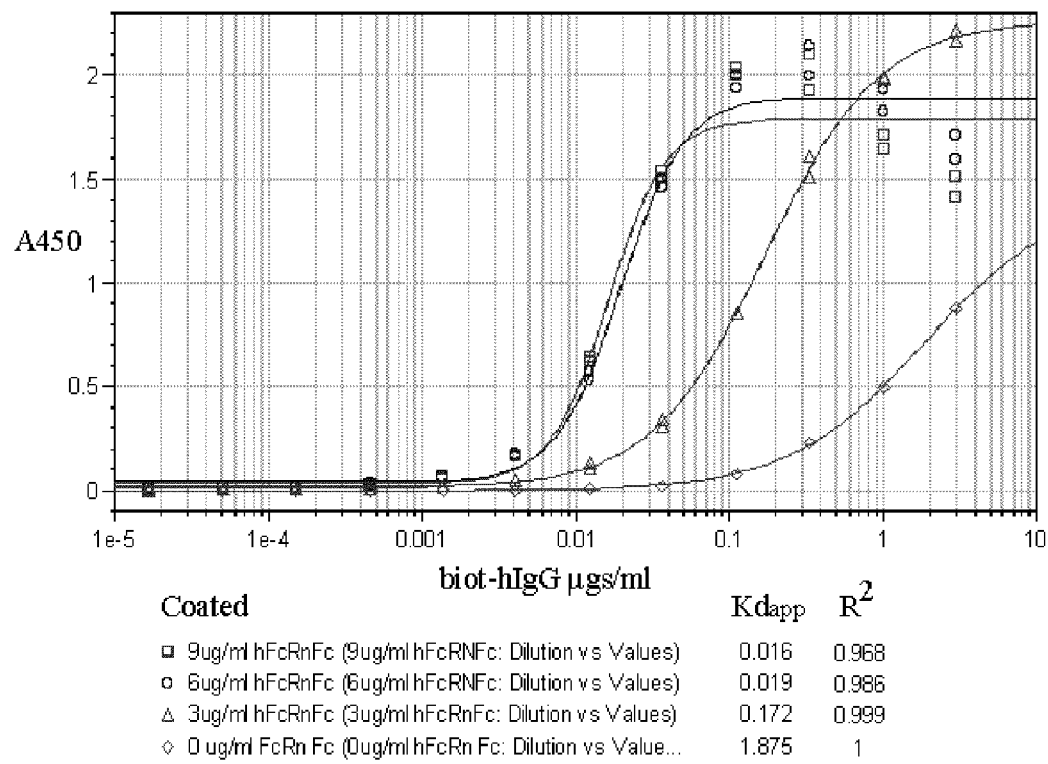
FIG. 10 shows the binding of biotinylated hIgG to hFcRnFc coated on to ELISA plates at varied concentrations of 3, 6 and 9 µg/ml. The biotinylated hIgG concentration was varied as indicated and a HPR-streptavidin was used at a concentration of 1:20,000 and developed with standard protocols. After stopping the reaction the Absorbance was read at 450 nm. The hFcRnFc at 9 µg/ml (□) and 6 µg/ml (O) show no change in the binding curve, where as 3 µg/ml (Δ) hFcRnFc shows decreased binding to coated hIgG. The negative control (◇) shows the background binding of the streptavidinHRP in the absence of hFcRnFc.

All washes and dilutions are done in pH 6.0 PBS unless otherwise indicated. Plates were coated overnight at 4° C. with altered IgG antibodies at 5 ug/ml at 100 uL per well. Plates were washed 3 times and then coated with 1% BSA in for 2 h. The plates are then washed three times, and 100 uL of appropriate serially diluted FcRnFc was incubated for 90 min. The plate was again washed 3 times and 100 uL of the appropriate secondary mAb-HRP or streptavidin HRP was added, incubated for 90 min, and the plates were washed again and developed as appropriately for the chosen secondary mAb and the absorbance read. The apparent dissociation constant (Kd) was determined using a four parameter fit of the binding data as shown in FIG. 10.

d) Competitive Binding Assays:

The relative binding affinities of the variant antibodies for a labeled dimeric FcRn construct (bhFcRnFc) was determined using two proximity assays (FRET and AlphaScreen) in which the competition binding between a fluorescently labeled control antibody (5C8) and the altered antibodies of Example 4 was evaluated.

i) FRET Binding Assay:

FRET assays were carried out in black half-well ELISA plates with a total reaction volume of 30 uL. Each reaction mix contained the following: a) 1 nM of the control antibody (h5C8) labelled with Europium (EU); b) 250 nM of streptavidin labeled with a second fluorophore (APC); c) the appropriate competitor mAb from Example 4 (0-5 uMolar; 0-0.75 mg/ml); and d) 200 nM of bhFcRnFc; in a pH 5.8 buffer with 100 mM NaCl and 0.005% P20 detergent (Biacore, Tween-20). The bhFcRnFc was added last to the reaction mix.

Reactions were incubated for 30 minutes at room temperature and then read on an LJL Analyst (Molecular Devices) with an excitation wave length of 615 and a fluorescence emission wavelength of 665. The settings for LJL Analyst were 50 us time delay and 400 µs read. The signal ratio (ΔF) of APC and Eu (665 nm/615 nm) was plotted versus the concentration of competitor mAb to determine the IC50 (βg/ml). The negative control reaction lacked the Europium labeled hAb and competitor IgG, the positive control contained no competitor IgG.

Relative IC$_{50}$ values (mutant IC50/w.t. control IC50) were determined for each altered antibody and are plotted in FIG. 6. FIG. 6 demonstrates that the antibodies comprising mutations at EU positions 285, 286, 290, and 304 in particular the mutations H285E, N286D, K290E, and S304D, resulted in enhanced relative binding affinity (Relative IC$_{50}$<1) for the dimeric FcRn/Fc fusion protein. In contrast, many of the altered antibodies (ie. those containing mutations at EU positions 252, 255, 279, 282, 284, 285, 287, 288, 290, 304, 306, 309, 376, 434, and 438) exhibited a reduced apparent binding affinity (Relative IC$_{50}$>1) for the dimeric FcRn/Fc fusion protein. In particular, mutations at EU positions 282 (V282E), 290 (K290D), 438 (Q438E), and 434 (N434L) exhibited a pronounced decrease in binding affinity for FcRn. For example, the mutation N434L, resulted in an FcRn binding affinity that was ~4000× lower than the control antibody.

ii) ALPHA Screen Binding Assay:

AlphaScreen is a bead-based assay, which uses donor and acceptor beads that are separately conjugated to binding partners (ie. the dimer Fc binding protein and the altered Fc polypeptide). The donor beads are coated with a photosensitizer, which upon laser excitation (e.g. at 680 nm) produces singlet oxygen. The chemiluminescent-coated acceptor beads react with the singlet oxygen to emit light at 520-620 nm. Due to the very short half-life of the singlet oxygen in solution the acceptor bead chemiluminescence is proportional to the proximity of the donor bead. Therefore binding of donor and acceptor beads results in a greatly enhanced chemiluminescent signal.

The biotinylated Fc/FcRn fusion protein (bhFcRnFc) was added (2 µg/ml final concentration) onto duplicate serial dilutions of the altered antibodies of Example 4 in 384 well white Costar plates (Corning, Acton, Mass.). After 30 minute incubation at room temperature, human IgG$_1$ conjugated acceptor beads (conjugated by PerkinElmer Biosignal Inc., Montreal, Canada) and streptavidin conjugated donor beads (PerkinElmer Biosignal Inc., Montreal, Canada) were added at 20 µg/ml (final concentration) in 25 µl final reaction volume. This arrangement, resulted in reaction mixtures containing the streptavidin-conjugated donor bead bound the Fc/FcRn fusion protein and the IgG1-conjugated accetor beads bound to the altered antibodies.

Reaction mixtures were incubated at room temperature for 1 hour and read on Fusion-Alpha reader (PerkinElmer Biosignal Inc., Montreal, Canada). PBS, 0.1% bovine serum albumin and 0.01% Tween-20 at pH 6.0 was used as assay buffer. A human IgG$_1$ was used as positive control. Assay buffer at pH 7.0 was used as a negative control to confirm non-binding of human IgG1 to human FcRnFc. Results were analyzed using GraphPad Prism software.

Figure 7:
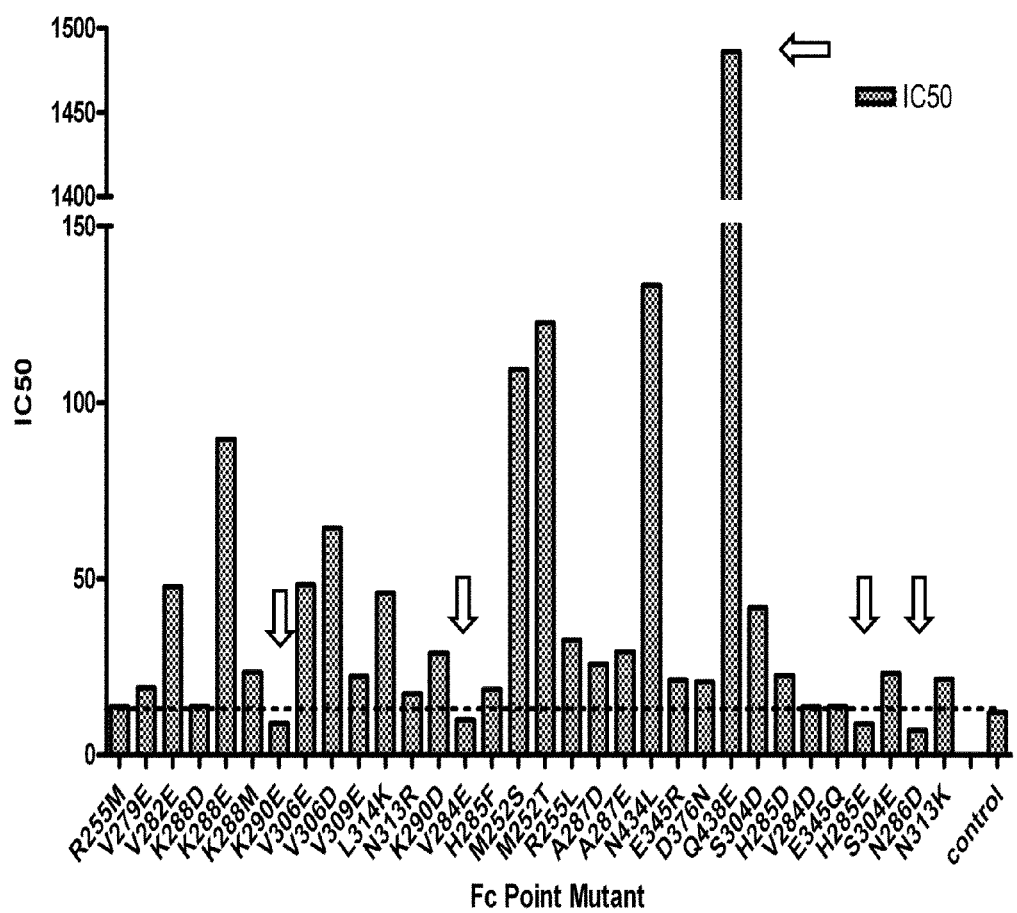
FIG. 7 shows the results obtained using an AlphaScreen assay for evaluation of the FcRn binding affinity of the altered polypeptides of the invention. Mutations with a measurable increase in binding affinity (V284E, H285E, N286D, and K290E) are indicated with downward pointing arrows. A mutation (Q438E) with a pronounced decrease in binding affinity is indicated by a leftward pointing arrow.
Figure 8:
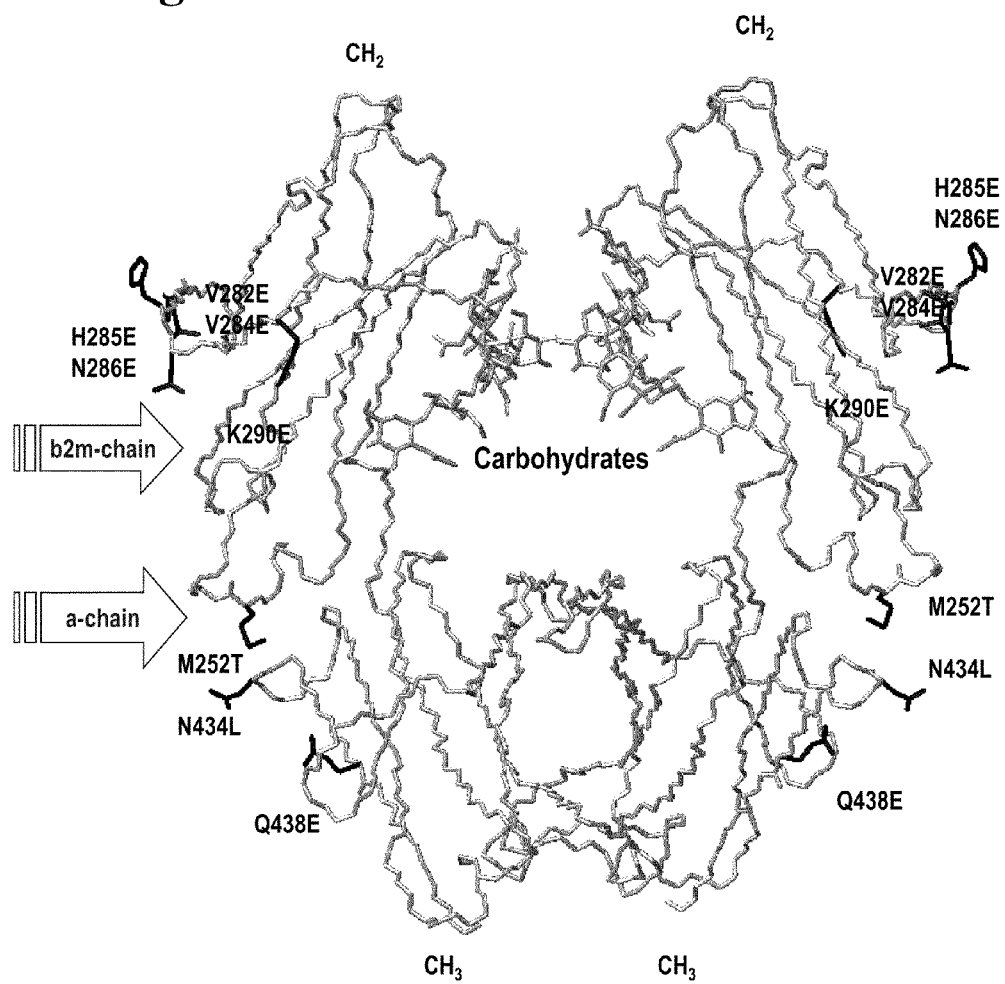
FIG. 8 shows the structural model of the Fc region of huCBE11 heavy chain used in the methods of the invention. The location of particular "up mutants" (V284E, H285E, N286E, K290E) with enhanced affinity for FcRn and particular "down mutants" (V282E, M252T, N434L, Q438L) with reduced affinity for FcRn are indicated in relation to other domains of the FcRn.

IC$_{50}$ values (µg/ml) determined for each altered antibody are summarized in FIG. 7. FIG. 7 demonstrates that the antibodies comprising mutations at EU positions 284, 285, 286, and 288, in particular the mutations V284E, H285E, N286D, K290E, resulted in a enhanced apparent binding affinity (IC$_{50}$<1) for the dimeric FcRn/Fc fusion protein, relative to control antibody. In contrast, many of the altered antibodies (ie. those containing mutation at EU positions 252, 255, 279, 282, 284, 285, 286, 290, 304, 306, 309, 314, 313, 345, 376, 434, and 438) exhibited a reduced apparent binding affinity (IC$_{50}$>1) for the dimeric FcRn/Fc fusion protein, relative to control antibody. In particular, mutations at EU positions 252 (M252S and M252T), 434 (N434L), and 438 (Q438E) exhibited pronounced decreased in binding affinity for FcRn. For example, the mutation Q438E, resulted in an FcRn binding affinity that was ~1500× lower than the control antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. An IgG Fc-containing polypeptide comprising an altered Fc region, wherein said Fc-containing polypeptide comprises at least one mutation within the Fc region as compared to a starting Fc-containing polypeptide and wherein the at least one mutation is a substitution at EU amino acid position 304 with aspartate or glutamate in combination with a second mutation selected from the group consisting of:
   a substitution at EU amino acid position 284 with aspartate or glutamate;
   a substitution at EU amino acid position 285 with aspartate or glutamate;

a substitution at EU amino acid position 286 with aspartate or glutamate;

a substitution at EU amino acid position 288 with a aspartate or glutamate;

a substitution at EU amino acid position 290 with aspartate or glutamate; and a substitution at EU amino acid position 305 with aspartate or glutamate, wherein the IgG Fc-containing polypeptide binds FcRn with different binding affinity compared to the starting polypeptide that does not contain the mutations.

2. The IgG Fc-containing polypeptide of claim 1, wherein the polypeptide is an antibody or fragment thereof, the an antibody or fragment thereof comprising VL and VH domains, said VL and VH domains comprising complementarity determining regions (CDRs) which confer binding specificity on the antibody or fragment thereof.

3. The IgG Fc-containing polypeptide of claim 1, wherein the polypeptide is a fusion protein.

4. The IgG Fc-containing polypeptide of claim 1, wherein the Fc region is from a human IgG antibody.

5. The IgG Fc-containing polypeptide of claim 1, wherein the starting polypeptide comprises the amino acid sequence of SEQ ID NO:2.

6. The IgG Fc-containing polypeptide of claim 2, wherein the polypeptide comprises one or more non-human amino acids residues in a complementarity determining region (CDR) of said VL or VH domain.

7. The IgG Fc-containing polypeptide of claim 2, wherein the polypeptide binds (a) an antigen and (b) an FcR.

8. The IgG Fc-containing polypeptide of claim 3, wherein the polypeptide binds (a) a ligand and (b) an FcR.

9. The IgG Fc-containing polypeptide of claim 1, wherein the altered polypeptide exhibits one binding affinity for the FcR at a first pH, and exhibits a different binding affinity for the FcR at a second pH.

10. The IgG Fc-containing polypeptide of claim 1, wherein the altered polypeptide binds to Protein A or G.

11. A composition comprising the IgG Fc-containing polypeptide of claim 1 and a pharmaceutically-acceptable carrier.

12. The IgG Fc-containing polypeptide of claim 9 that exhibits an affinity for an FcRn at a first pH, and exhibits a different affinity for an FcRn at a second pH.

13. A composition comprising the polypeptide of claim 12 and a pharmaceutically acceptable carrier.

14. The IgG Fc-containing polypeptide of claim 2, wherein the Fc region is from a human IgG antibody.

15. The IgG Fc-containing polypeptide of claim 3, wherein the Fc region is from a human IgG antibody.

16. The IgG Fc-containing polypeptide of claim 2, wherein the starting polypeptide comprises the amino acid sequence of SEQ ID NO:2.

17. The IgG Fc-containing polypeptide of claim 3, wherein the starting polypeptide comprises the amino acid sequence of SEQ ID NO:2.

* * * * *

SEQUENCE LISTING

<160> NUMBER OF SEQ ID NOS: 12

<210> SEQ ID NO 1
<211> LENGTH: 110
<212> TYPE: PRT
<213> ORGANISM: Homo sapiens

<400> SEQUENCE: 1

```
Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 2
<211> LENGTH: 106
<212> TYPE: PRT
<213> ORGANISM: Homo sapiens

<400> SEQUENCE: 2

```
Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 3
<211> LENGTH: 1350
<212> TYPE: DNA
<213> ORGANISM: Homo sapiens

<400> SEQUENCE: 3

-continued

```
gaggtacaac tggtggagtc tgggggaggc ttagtgaagc ctggagggtc cctgaggctc      60
tcctgtgcag cctctggatt cactttcagt gactattaca tgtattggtt cgccaggcc     120
ccgggaaagg gctggagtg gtcgcaacc attagtgatg gtggtagtta cacctactat      180
ccagacagtg tgaaggggcg attcaccatc tccagagaca tgccaagaa cagcctctac     240
ctgcagatga gcagcctgag ggctgaggac acagctgtgt attactgcgc aagagaggag    300
aatggtaact tttactactt tgactactgg ggccaaggga ccacggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaagactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ttggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tcccggttga                                    1350
```

<210> SEQ ID NO 4
<211> LENGTH: 449
<212> TYPE: PRT
<213> ORGANISM: Homo sapiens

<400> SEQUENCE: 4

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Tyr Trp Phe Arg Gln Ala Pro Gly Lys Gly Leu Glu Trp Val
         35                  40                  45

Ala Thr Ile Ser Asp Gly Gly Ser Tyr Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Ser Ser Leu Arg Ala Glu Asp Thr Ala Val Tyr Tyr Cys
                 85                  90                  95

Ala Arg Glu Glu Asn Gly Asn Phe Tyr Tyr Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 5
<211> LENGTH: 645
<212> TYPE: DNA
<213> ORGANISM: Homo sapiens

<400> SEQUENCE: 5
gatatccaga tgacccagtc tccatcatcc ttgtctgcat cggtgggaga cagggtcact      60
atcacttgca aggcgggtca ggacattaaa agctatttaa gctggtacca gcagaaacca     120
gggaaagcgc ctaagcttct gatctattat gcaacaaggt tggcagatgg ggtcccatca     180
agattcagtg gcagtggatc tgggacagat tatactctaa ccatcagcag cctgcagcct     240
gaggatttcg caacttatta ctgtctacag catggtgaga gccgtggac gttcggtgga     300 ggcaccaagc tggagatcaa acgaactgtg gctgcaccat ctgtcttcat cttcccgcca     360

```
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag cacccctgacg    540 ctgagcaaag cagactacga gaaacacaaa gtctacgcct gcgaagtcac ccatcagggc      600
ctgagctcgc ccgtcacaaa gagcttcaac aggggagagt gttag                     645
```

<210> SEQ ID NO 6
<211> LENGTH: 214
<212> TYPE: PRT
<213> ORGANISM: Homo sapiens

<400> SEQUENCE: 6

```
Asp Ile Gln Met Thr Gln Ser Pro Ser Ser Leu Ser Ala Ser Val Gly
 1               5                  10                  15

Asp Arg Val Thr Ile Thr Cys Lys Ala Gly Gln Asp Ile Lys Ser Tyr
            20                  25                  30

Leu Ser Trp Tyr Gln Gln Lys Pro Gly Lys Ala Pro Lys Leu Leu Ile
        35                  40                  45

Tyr Tyr Ala Thr Arg Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gly Gly Thr Lys Leu Glu Ile Lys Arg Thr Val Ala Ala
           100                 105                 110

Pro Ser Val Phe Ile Phe Pro Pro Ser Asp Glu Gln Leu Lys Ser Gly
       115                 120                 125

Thr Ala Ser Val Val Cys Leu Leu Asn Asn Phe Tyr Pro Arg Glu Ala
   130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 360
<212> TYPE: DNA
<213> ORGANISM: Homo sapiens

<400> SEQUENCE: 7

```
atgtctcgct ccgtggcctt agctgtgctc gcgctactct ctctttctgg cctggaggct       60
atccagcgta ctccaaagat tcaggtttac tcacgtcatc agcagagaa tggaaagtca      120 aatttcctga attgctatgt gtctgggttt catccatccg acattgaagt tgacttactg      180
aagaatggag agagaattga aaagtggag cattcagact tgtctttcag caaggactgg      240
tctttctatc tcttgtacta cactgaattc acccccactg aaaaagatga gtatgcctgc      300
cgtgtgaacc atgtgacttt gtcacagccc aagatagtta gtgggatcg agacatgtaa      360
```

<210> SEQ ID NO 8
<211> LENGTH: 119
<212> TYPE: PRT
<213> ORGANISM: Homo sapiens

<400> SEQUENCE: 8

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 9
<211> LENGTH: 1575
<212> TYPE: DNA
<213> ORGANISM: Homo sapiens

<400> SEQUENCE: 9

```
atgggggtcc cgcggcctca gccctgggcg ctggggctcc tgctctttct ccttcctggg      60
agcctgggcg cagaaagcca cctctcccte ctgtaccacc ttaccgcggt gtcctcgcct     120
gccccgggga ctcctgcctt ctgggtgtcc ggctggctgg cccgcagca gtacctgagc      180
tacaatagcc tgcgggggcga ggcggagccc tgtggagctt gggtctggga aaaccaggtg    240
tcctggtatt gggagaaaga gaccacagat ctgaggatca aggagaagct ctttctggaa     300
gcttcaaag cttttggggg aaaaggtccc tacactctgc agggcctgct gggctgtgaa      360
ctgggccctg acaacaccte ggtgcccacc gccaagttcg ccctgaacgg cgaggagttc     420
atgaatttcg acctcaagca gggcacctgg ggtggggact ggccgaggc cctggctatc     480
agtcagcggt ggcagcagca ggacaaggcg ccaacaagg agctcacctt cctgctattc     540
tcctgcccgc accgcctgcg ggagcacctg agaggggcc gcggaaacct ggagtggaag     600
gagcccccct ccatgcgcct gaaggcccga cccagcagcc ctggcttttc cgtgcttacc    660
tgcagcgcct ctcccttcta ccctccggag ctgcaacttc ggttcctgcg aatgggctg     720
gccgctggca ccggccaggg tgacttcggc cccaacagtg acggatcctt ccacgcctcg    780
tcgtcactaa cagtcaaaag tggcgatgag caccactact gctgcattgt gcagcacgcg    840
gggctggcgc agccctcag gtggagctg aatctccag ccaagtcctc cgtcgacaaa       900
actcacacat gcccaccgtg cccagcacct gaactcctgg ggggaccgtc agtcttcctc    960
ttccccccaa aacccaagga caccctcatg atctcccgga cccctgaggt cacatgcgtg   1020
gtggtggacg tgagccacga agaccctgag gtcaagttca actggtacgt ggacggcgtg   1080
gaggtgcata atgccaagac aaagccgcgg gaggagcagt acaacagcac gtaccgtgtg   1140
gtcagcgtcc tcaccgtcct gcactaacgac tggctgaatg gcaaggagta caagtgcaag   1200
```

```
gtctccaaca aagccctccc agcccccatc gagaaaacca tctccaaagc caagggcag      1260 ccccgagaac cacaggtgta caccctgccc ccatcccggg atgagctgac caagaaccag     1320
gtcagcctga cctgcctggt caaaggcttc tatcccagcg acatcgccgt ggagtgggag     1380
agcaatgggc agccggagaa caactacaag accacgcctc ccgtgttgga ctccgacggc     1440
tccttcttcc tctacagcaa gctcaccgtg gacaagagca ggtggcagca ggggaacgtc     1500
ttctcatgct ccgtgatgca tgaggctctg cacaaccact acacgcagaa gagcctctcc     1560
ctgtctccgg gttga                                                      1575
```

<210> SEQ ID NO 10
<211> LENGTH: 524
<212> TYPE: PRT
<213> ORGANISM: Homo sapiens

<400> SEQUENCE: 10

```
Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Asp Lys Thr His Thr Cys
    290                 295                 300

Pro Pro Cys Pro Ala Pro Glu Leu Leu Gly Gly Pro Ser Val Phe Leu
```

```
                305                 310                 315                 320
Phe Pro Pro Lys Pro Lys Asp Thr Leu Met Ile Ser Arg Thr Pro Glu
                325                 330                 335
Val Thr Cys Val Val Val Asp Val Ser His Glu Asp Pro Glu Val Lys
                340                 345                 350
Phe Asn Trp Tyr Val Asp Gly Val Glu Val His Asn Ala Lys Thr Lys
                355                 360                 365
Pro Arg Glu Glu Gln Tyr Asn Ser Thr Tyr Arg Val Val Ser Val Leu
                370                 375                 380
Thr Val Leu Ala Asn Asp Trp Leu Asn Gly Lys Glu Tyr Lys Cys Lys
385                 390                 395                 400
Val Ser Asn Lys Ala Leu Pro Ala Pro Ile Glu Lys Thr Ile Ser Lys
                405                 410                 415
Ala Lys Gly Gln Pro Arg Glu Pro Gln Val Tyr Thr Leu Pro Pro Ser
                420                 425                 430
Arg Asp Glu Leu Thr Lys Asn Gln Val Ser Leu Thr Cys Leu Val Lys
                435                 440                 445
Gly Phe Tyr Pro Ser Asp Ile Ala Val Glu Trp Glu Ser Asn Gly Gln
                450                 455                 460
Pro Glu Asn Asn Tyr Lys Thr Thr Pro Pro Val Leu Asp Ser Asp Gly
465                 470                 475                 480
Ser Phe Phe Leu Tyr Ser Lys Leu Thr Val Asp Lys Ser Arg Trp Gln
                485                 490                 495
Gln Gly Asn Val Phe Ser Cys Ser Val Met His Glu Ala Leu Ala Gln
                500                 505                 510
His Tyr Thr Gln Lys Ser Leu Ser Leu Ser Pro Gly
                515                 520

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Gly Gly Gly Ser Ser Gly Gly Gly Ser Gly Gly
1               5                   10

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Gly Gly Gly Gly Ser Gly Gly Gly Gly Ser Gly Gly Gly Gly Ser Gly
1               5                   10                  15
Gly Gly Ser Gly Gly Gly Ala Ser
                20                  25
```